US012344696B2

(12) United States Patent
Canich et al.

(10) Patent No.: US 12,344,696 B2
(45) Date of Patent: Jul. 1, 2025

(54) PROCESS TO PRODUCE LOW VISCOSITY POLYALPHAOLEFINS USING NON-AROMATIC-HYDROCARBON SOLUBLE ACTIVATORS

(71) Applicant: ExxonMobil Chemical Patents Inc., Baytown, TX (US)

(72) Inventors: Jo Ann M. Canich, Houston, TX (US); Jian Yang, Houston, TX (US); Jennifer L. Rapp, Houston, TX (US); Catherine A. Faler, Houston, TX (US); Margaret T. Whalley, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 599 days.

(21) Appl. No.: 17/633,910

(22) PCT Filed: Jul. 28, 2020

(86) PCT No.: PCT/US2020/043862
§ 371 (c)(1),
(2) Date: Feb. 8, 2022

(87) PCT Pub. No.: WO2021/030045
PCT Pub. Date: Feb. 18, 2021

(65) Prior Publication Data
US 2022/0298273 A1    Sep. 22, 2022

Related U.S. Application Data

(60) Provisional application No. 62/885,103, filed on Aug. 9, 2019.

(51) Int. Cl.
| C07C 2/30 | (2006.01) |
| C07C 2/32 | (2006.01) |
| C08F 4/6592 | (2006.01) |
| C08F 110/14 | (2006.01) |

(52) U.S. Cl.
CPC ............ C08F 4/65925 (2013.01); C07C 2/30 (2013.01); C07C 2/32 (2013.01); C08F 110/14 (2013.01)

(58) Field of Classification Search
CPC ............ C07C 2/30; C07C 2/32; C08F 4/6592
See application file for complete search history.

(56) References Cited

U.S. PATENT DOCUMENTS

| 3,367,987 A | 2/1968 | Walsh |
| 5,573,657 A | 11/1996 | Degnan et al. |
| 5,696,213 A | 12/1997 | Schiffino et al. |
| 5,705,577 A | 1/1998 | Rossi et al. |
| 5,919,983 A | 7/1999 | Rosen et al. |
| 6,022,929 A | 2/2000 | Chen et al. |
| 6,121,185 A | 9/2000 | Rosen et al. |
| 6,403,732 B2 | 6/2002 | Marks et al. |
| 6,818,585 B2 | 11/2004 | Crowther et al. |
| 6,846,778 B2 | 1/2005 | Johnson et al. |
| 7,053,254 B2 | 5/2006 | Miller |
| 7,087,602 B2 | 8/2006 | Thomas et al. |
| 7,101,940 B2 | 9/2006 | Schottek et al. |
| 7,199,072 B2 | 4/2007 | Crowther et al. |
| 7,214,745 B2 | 5/2007 | Arai et al. |
| 7,241,375 B2 | 7/2007 | Johnson et al. |
| 7,344,631 B2 | 3/2008 | Bishop et al. |
| 7,799,879 B2 | 9/2010 | Crowther et al. |
| 7,985,816 B2 | 7/2011 | Crowther et al. |
| 8,318,998 B2 | 11/2012 | Crowther et al. |
| 8,399,724 B2 | 3/2013 | Crowther et al. |
| 8,426,659 B2 | 4/2013 | Holtcamp et al. |
| 8,501,894 B2 | 8/2013 | Crowther et al. |
| 8,580,902 B2 | 11/2013 | Crowther et al. |
| 8,623,974 B2 | 1/2014 | Jiang et al. |
| 8,642,497 B2 | 2/2014 | Berris |
| 8,669,326 B2 | 3/2014 | Hagadorn et al. |
| 8,669,330 B2 | 3/2014 | Stewart |
| 8,748,361 B2 | 6/2014 | Wu et al. |
| 8,754,170 B2 | 6/2014 | Hagadorn et al. |
| 8,816,027 B2 | 8/2014 | Crowther et al. |
| 8,835,563 B2 | 9/2014 | Crowther et al. |
| 8,835,587 B2 | 9/2014 | Crowthers et al. |
| 8,841,394 B2 | 9/2014 | Crowther et al. |
| 8,841,397 B2 | 9/2014 | Holtcamp et al. |

(Continued)

FOREIGN PATENT DOCUMENTS

| CN | 105622807 A | 6/2016 |
| EP | 0283739 A2 | 9/1988 |

(Continued)

OTHER PUBLICATIONS

Extended European Search Report received for European Patent Application No. 20852992.5 mailed on Aug. 11, 2022, 7 Pages.
U.S. Appl. No. 61/136,172, "Polyalkyl succinic acid derivatives as additives for fouling mitigation in petroleum refinery processes" filed Aug. 15, 2008, 27 Pages.
U.S. Appl. No. 62/477,683, "Metallocene-Catalyzed Polyalpha-Olefins" filed Mar. 28, 2017, 57 Pages.
U.S. Appl. No. 62/477,706, "Metallocene Compounds" filed Mar. 28, 2017, 55 Pages.
Cherian, A. E et al., (2005) "Synthesis of Allyl-Terminated Syndiotactic Polypropylene: Macromonomers for the Synthesis of Branched Polyolefins", Macromolecules, vol. 38, No. 15, pp. 6259-6268.
Eshuis, J. J. W. et al., (1990) "Catalytic olefin ougomerization and polymerization with cationic group IV metal complexes [Cp2? MMe(THT)]+[BPh4]−, M = Ti, Zr and Hf", Journal of molecular catalysis, vol. 62, No. 3, pp. 277-287.

(Continued)

Primary Examiner — Caixia Lu

(57) ABSTRACT

A process for making a poly alpha-olefin (PAO) having high vinylidene content (or combined vinylidene and tri-substituted vinylene content) and low vinyl and/or di-substituted vinylene content, as well as a relatively low molecular weight comprising contacting a feed containing a $C_6$-$C_{32}$ alpha-olefin with a catalyst system comprising non-aromatic-hydrocarbon soluble activator and a metallocene compound, typically a cyclopentadienyl-tetrahydro-s-indacenyl group 4 transition metal compound.

29 Claims, No Drawings

(56) References Cited

U.S. PATENT DOCUMENTS

| | | | |
|---|---|---|---|
| 8,940,839 B2 | 1/2015 | Hagadorn et al. | |
| 8,981,029 B2 | 3/2015 | Jiang et al. | |
| 9,409,834 B2 | 8/2016 | Wu et al. | |
| 9,611,280 B2 | 4/2017 | Takaishi et al. | |
| 10,968,290 B2 | 4/2021 | Crowther et al. | |
| 11,041,031 B2 | 6/2021 | Faler et al. | |
| 11,084,894 B2* | 8/2021 | Yang | C07C 2/30 |
| 11,117,908 B2 | 9/2021 | Faler et al. | |
| 11,414,436 B2 | 8/2022 | Faler et al. | |
| 11,680,121 B2* | 6/2023 | Yang | C07C 2/32 |
| | | | 526/127 |
| 2002/0062011 A1 | 5/2002 | Richard, Jr. et al. | |
| 2003/0013913 A1 | 1/2003 | Schottek et al. | |
| 2004/0102590 A1 | 5/2004 | Mccullough et al. | |
| 2005/0159299 A1 | 7/2005 | Rodriguez et al. | |
| 2009/0318644 A1 | 12/2009 | Brant et al. | |
| 2010/0038290 A1 | 2/2010 | Wang et al. | |
| 2010/0087349 A1 | 4/2010 | Lee et al. | |
| 2010/0170829 A1 | 7/2010 | Ng et al. | |
| 2012/0245310 A1 | 9/2012 | Crowther et al. | |
| 2012/0245312 A1 | 9/2012 | Holtcamp et al. | |
| 2012/0316303 A1 | 12/2012 | Hanton et al. | |
| 2013/0023633 A1 | 1/2013 | Holtcamp et al. | |
| 2014/0087986 A1 | 3/2014 | Patil et al. | |
| 2015/0203602 A1 | 7/2015 | Sun et al. | |
| 2016/0108062 A1 | 4/2016 | Takaishi et al. | |
| 2017/0233516 A1 | 8/2017 | Yang et al. | |
| 2018/0037521 A1* | 2/2018 | Islam et al. | C07C 2/32 |
| | | | 526/160 |
| 2018/0094088 A1 | 4/2018 | Crowther et al. | |
| 2019/0161560 A1 | 5/2019 | Yang et al. | |
| 2019/0248936 A1* | 8/2019 | Yang | C07C 2/30 |
| 2019/0330139 A1 | 10/2019 | Faler et al. | |

FOREIGN PATENT DOCUMENTS

| | | |
|---|---|---|
| EP | 0610851 A1 | 8/1994 |
| EP | 0659756 A1 | 6/1995 |
| JP | 2005-336092 A | 12/2005 |
| JP | 2011-037164 A | 2/2011 |
| KR | 17250040000 B1 | 4/2017 |
| WO | 95/27717 A1 | 10/1995 |
| WO | 02/02577 A1 | 1/2002 |
| WO | 2005/121280 A1 | 12/2005 |
| WO | 2009/155471 A2 | 12/2009 |
| WO | 2009/155472 A2 | 12/2009 |
| WO | 2009/155510 A2 | 12/2009 |
| WO | 2009/155517 A2 | 12/2009 |
| WO | 2010/014344 A2 | 2/2010 |
| WO | 2012/133717 A1 | 10/2012 |
| WO | 2012/134720 A2 | 10/2012 |
| WO | 2017/155149 A1 | 9/2017 |
| WO | 2017/188602 A1 | 11/2017 |
| WO | 2018/067289 A1 | 4/2018 |
| WO | 2018/094088 A1 | 5/2018 |
| WO | 2018/182982 A2 | 10/2018 |
| WO | 2021/030045 A1 | 2/2021 |

OTHER PUBLICATIONS

Girolami, G. S., (1994) ""A simple back of the envelope" method for estimating the densities and molecular volumes of liquids and solids", Journal of Chemical Education, vol. 71, No. 11, pp. 962-964.

Janiak, C. et al., (2006) "Metallocene Catalysts for Olefin Oligomerization", Macromolecular symposia, vol. 236, No. 1, pp. 14-22.

Kaneyoshi, H. et al., (2005) "Synthesis of Block and Graft Copolymers with Linear Polyethylene Segments by Combination of Degenerative Transfer Coordination Polymerization and Atom Transfer Radical Polymerization", Macromolecules, vol. 38, No. 13, pp. 5425-5435.

Kolodka, E. et al., (2002) "Copolymerization of Propylene with Poly(ethylene-co-propylene) Macromonomer and Branch Chain-Length Dependence of Rheological Properties", Macromolecules, vol. 35, No. 27, pp. 10062-10070.

Kropp, P. J. et al., (1990) "Surface-mediated reactions. 1. Hydrohalogenation of alkenes and alkynes", Journal of the American Chemical Society, vol. 112, No. 20, pp. 7433-7434.

Linas, G. H. et al., (1988) "(C5Me5)SiMe3 as a mild and effective reagent for transfer of the C5Me5 ring: an improved route to monopentamethylcyclopentadienyl trihalides of the group 4 elements", Journal of organometallic chemistry, vol. 340, No. 1, pp. 37-40.

Markel, E. J. et al., (2000) "Metallocene-Based Branch-Block Thermoplastic Elastomers", Macromolecules, vol. 33, No. 23, pp. 8541-8548.

Moscardi, G. et al., (2001) "Propene Polymerization with the Isospecific, Highly Regioselective rac-Me2C(3-t-Bu-1-Ind)2ZrCl2/MAO Catalyst. 2. Combined DFT/MM Analysis of Chain Propagation and Chain Release Reactions", Organometallics, vol. 20, No. 10, pp. 1918-1931.

Oliveira, J. V. et al., (2000) "High-Pressure Phase Equilibria for Polypropylene-Hydrocarbon Systems", Industrial & engineering chemistry research, vol. 39, No. 12, pp. 4627-4633.

International Preliminary Report on Patentability received for PCT Application No. PCT/US2020/043862, mailed on Feb. 17, 2022, 10 Pages.

International Search Report and Written Opinion received for PCT Application No. PCT/US2020/043862, mailed on Nov. 6, 2020, 12 Pages.

Rose, J. M. et al., (2008) "Poly(ethylene-co-propylene macromonomer)s: Synthesis and Evidence for Starlike Conformations in Dilute Solution", Macromolecules, vol. 41, No. 3, pp. 559-567.

Rudnick, L. R., (2009) "Lubricant Additives: Chemistry and Applications", Second Edition, CRC Press, pp. 143-170.

Rulhoff, S. et al., (2006) "Synthesis and Characterization of Defined Branched Poly(propylene)s with Different Microstructures by Copolymerization of Propylene and Linear Ethylene Oligomers (Cn = 26-28) with Metallocenes/MAO Catalysts", Macromolecular Chemistry and Physics, vol. 207, No. 16, pp. 1450-1460.

Small, B. L. et al., (1999) "Polymerization of Propylene by a New Generation of Iron Catalysts: Mechanisms of Chain Initiation, Propagation, and Termination", Macromolecules, vol. 32, No. 7, pp. 2120-2130.

Toyota, A. et al., (2002) "Synthesis of terminally functionalized polyolefines", Polymer Bulletin, vol. 48, No. 3, pp. 213-219.

Weng, W. et al., (2000) "Synthesis of vinyl-terminated isotactic poly(propylene)", Macromolecular rapid communications, vol. 21, No. 16, pp. 1103-1107.

X. Yang et al., "Cationic Metallocene Polymerization Catalysts. Synthesis and Properties of the First Base-Free Zirconocene Hydride", Angew. Chem. Int. Ed. Engl. 1992, v31, No. 10, pp. 1375-1377.

E. Kolodka et al., "Synthesis and Characterization of Long-Chain-Branched Polyolefins with Metallocene Catalysts. Copolymerization of Ethylene with Poly(ethylene-co-propylene) Macromonomer", Macromol. Rapid Commun. 2003, v24, pp. 311-315.

* cited by examiner

PROCESS TO PRODUCE LOW VISCOSITY POLYALPHAOLEFINS USING NON-AROMATIC-HYDROCARBON SOLUBLE ACTIVATORS

STATEMENT OF RELATED APPLICATIONS

This application is a National Phase Application claiming priority to PCT Application Serial No. PCT/US2020/043862 filed Jul. 28, 2020, which claims the priority benefit of Provisional Application No. 62/885,103 filed Aug. 9, 2019, the disclosures of which are incorporated herein by reference in their entireties.

This application is related to U.S. Ser. No. 15/706,088, filed Sep. 15, 2017 (which is published as US 2018/0094088.

This application is also related to U.S. Ser. No. 15/921,757, filed Mar. 15, 2018 (which is published as WO 2018/182982.

This application is also related to U.S. Ser. No. 16/270,085, filed Feb. 7, 2019 which claims priority to and the benefit of U.S. Ser. No. 62/629,200, filed Feb. 12, 2018, and U.S. Ser. No. 62/732,311, filed Sep. 17, 2018.

This application is also related to U.S. Ser. No. 16/394,197, filed Apr. 25, 2019, and U.S. Ser. No. 16/394,166, filed Apr. 25, 2019, both of which claim priority to and the benefit of U.S. Ser. No. 62/662,972, filed Apr. 26, 2018 and U.S. Ser. No. 62/769,208, filed Nov. 19, 2018.

FIELD OF THE INVENTION

The present invention relates to process for making poly alpha-olefin (PAO) materials using catalysts systems comprising hydrocarbon soluble activator and a metallocene-compound selected to yield a high vinylidene content.

BACKGROUND OF THE INVENTION

Alpha-olefins, especially those containing about 6 to about 20 carbon atoms, and oligomers thereof have been used as intermediates in the manufacture of detergents, lubricants, or other types of commercial products. Longer chain alpha-olefins, such as vinylidene-terminated polydecenes are also known and can be useful as building blocks following functionalization or as macromonomers.

Metallocene catalyst systems can be used for polymerizing alpha-olefin polymers and oligomers. For example, US Patent Publication No. 2005/0159299 discloses polymerization using catalyst compounds, such as dimethylsilyl bis(2-methyl-4-phenyl-indenyl) zirconium dimethyl on a capped support, to produce about 50% vinyl and about 50% vinylidene terminal unsaturations (of the termini that are unsaturated). Another example includes U.S. Pat. No. 8,318,998, which discloses cyclopentadienyl-benzindenyl metallocene compounds useful for production of alpha-olefin polymers, such as ethylene and or propylene polymers, having high allyl chain end content. The Examples in this publication show that the resultant alpha-olefin polymers/oligomers have a proportionally low vinylidene content and a proportionally high vinyl content. US Patent Publication No. 2013/0023633 also discloses metallocene compounds and use thereof in making polyolefins having proportionally high vinyl content.

Another example, U.S. Pat. No. 8,748,361, discloses a mixture comprising unsaturated poly alpha-olefin (uPAO) material made from, e.g., oligomerization of alpha-olefins in the presence of metallocene catalysts. It was disclosed in this reference that the uPAOs could comprise, among others, vinyls, vinylenes, di-substituted vinylenes, and tri-substituted vinylenes. In this publication, mixtures of the uPAOs produced from the polymerization step were subsequently hydrogenated then separated by distillation to obtain a hydrogenated PAO material that is particularly suitable as the basestock for lubricating oil compositions used in various applications.

Ethylenically unsaturated PAO materials prepared from oligomerization of linear alpha-olefins are useful as an intermediates for making various specialty chemicals because of the reactivity of the C=C double bond. For example, various chemical functional groups can be bonded to the carbon backbone of the uPAO molecule when a chemical agent reactive with the C=C bond is allowed to contact the uPAO material. The functional group thus introduced onto the PAO structure can bring about unique properties to the functionalized and saturated PAO molecules.

It has been found that the reactivity of the C=C bonds in vinyls, vinylidenes, di-substituted vinylenes, and tri-substituted vinylenes are different with regard to many chemical functionalization agents. For a specific type of functionalization agent, one or more particular type(s) of olefin(s) may be more desirable than the other(s). In addition, uPAOs having various molecular weight and molecular weight distribution and differing reactivities may be desired for making differing derivatives comprising differing functional groups thereon. Vinylidenes and tri-substituted vinylenes are typically more reactive than di-substituted vinylenes with many common reagents reactive with C=C double bonds.

WO 2017/188602 discloses at paragraph [117] $Me_2Si(Me_4Cp)(2\text{-}Me\text{-}benzindenyl)MCl_2$, where the 2 position on the benzindenyl is methyl.

WO 2012/134720, compound G, discloses 1,3-dimethyl benz[e]indenyl)($Me_5Cp$)$HfMe_2$.

US Patent Publication No. 2018/0094088 discloses benzindenyl compounds such as (1,3-dimethyl benz[e]indenyl)($CpMe_5$)$ZrMe_2$ and (1,3-dimethyl benz[e]indenyl)($CpMe_4$)$ZrMe_2$.

U.S. Pat. No. 5,919,983 discloses polymerization of ethylene and octene using a catalyst system comprising [(Cis)$_2$MeN)]$^+$[B(PhF$_5$)$_4$]$^-$ activator having four fluoro-phenyl groups bound to the boron atom and two linear $C_{18}$ groups bound to the nitrogen, as well as describing other linear groups at column 3, line 51 et seq.

US 2003/0013913 (granted as U.S. Pat. No. 7,101,940) discloses various activators such as N,N-dimethylcyclohexylammoniumtetrakis(pentafluorophenyl)borate [0070], and N,N-diethylbenzylammoniumtetrakis(pentafluorophenyl)borate [0124].

US 2002/0062011 discloses phenyl dioctadecylammonium(hydroxyphenyl) tris(pentafluorophenyl)borate at paragraph [0200] and (pentafluorophenyl) dioctadecylammonium tetrakis(pentafluorophenyl)borate at paragraph [0209].

U.S. Pat. Nos. 7,799,879, 7,985,816, 8,580,902, 8,835,587, and WO 2010/014344 describe ammonium borate activators that include some that use a tetrakis(heptafluoronaphth-2-yl)borate anion.

Other publications of interest include, but are not necessarily limited to: U.S. application Ser. No. 12/642,453 filed Dec. 18, 2009; Ser. No. 12/533,465 filed Jul. 31, 2009; 61/136,172 filed Aug. 15, 2008; 62/477,683 filed Mar. 28, 2017; 62/477,706 filed Mar. 28, 2017; PCT Publication Nos. WO 1995/027717; WO 2009/155471; WO 2009/155472; WO 2009/155510; WO 2009/155517; WO 2017/155149; WO 2012/133717; WO 2018/0094088; WO 2018/182982;

U.S. Pat. Nos. 3,367,987; 7,214,745; 8,816,027; 8,669,326; 8,940,839; 8,754,170; 8,426,659; 8,841,397; 8,501,894; 8,669,330; 8,835,563; 8,841,394; 8,399,724; 8,623,974; 8,981,029; 6,403,732; 6,818,585; 7,199,072; US Patent Publication Nos. 2018/0094088; 2009/0318644, 2004/0102590; 2017/0233516; Japanese Publication No. JP 2005-336092; JP 2011-037164A; Chinese Publication No. CN 105622807; EP Publication Nos. EP 0659756; EP 0610851; EP 0283739; Korean Publication No. KR 17250040000; Rulhoff, S. et al. (2006) "Synthesis and Characterization of Defined Branched Poly(propylene)s with Different Microstructures by Copolymerization of Propylene and Linear Ethylene Oligomers ($C_n$=26-28) with Metallocenes/MAO Catalysts," *Macromolecules*, v. 207(16), pp. 1450-1460; Kaneyoshi, H. et al. (2005) "Synthesis of Block and Graft Copolymers with Linear Polyethylene Segments by Combination of Degenerative Transfer Coordination Polymerization and Atom Transfer Radical Polymerization," *Macromolecules*, v. 38(13), pp. 5425-5435; Teuben et al. (*Journal Molecular Catalysis*, v. 62, 1990, pp. 277-287); X. Yang et al. (1992) *Angew. Chem. Int'l Edition.*, Engl., v. 31, pp. 1375-1377; Small, B. L. et al. (1999) *Macromolecules*, v. 32(7), pp. 2120-2130; Weng, W. et al. (2000) *Macromolecular Rapid Comm.*, v. 21(16), pp. 1103-1107; Markel, E. J. et al. (2000) *Macromolecules*, v. 33(23), pp. 8541-8548; Moscardi, G. et al. (2001) *Organometallics*, v. 20(10) pp. 1918-1931; Zhu, S. et al. (2002) *Macromolecules*, v. 35(27), pp. 10062-10070 and (2003) *Macromolecular Rapid Commun.*, v. 24(4), pp. 311-315; Coates, G. W. et al. (2005) *Macromolecules*, v. 38(15), pp. 6259-6268; Rose, J. M. et al. (2008) *Macromolecules*, v. 41(03), pp. 559-567; Janiak, C. et al. (2006) *Macromolecular Symposia*, v. 236(1), pp. 14-22, WO 2002/002577; U.S. Pat. Nos. 7,087,602; 8,642,497; 6,121,185; 8,642,497; US 2015/0203602; U.S. Ser. No. 16/394,166 filed Apr. 25, 2019, CAS number 909721-53-5, CAS number 943521-08-2; and U.S. Pat. No. 8,642,497.

There remains a need for uPAO materials having a high concentration of vinylidenes (and/or of vinylidenes and tri-substituted vinylenes combined), as well as for processes for, and catalyst systems specifically tailored to, making such uPAO materials.

SUMMARY OF THE INVENTION

This invention relates to a process for making a poly alpha-olefin, PAO, comprising: contacting a feed comprising a $C_6$-$C_{32}$ alpha-olefin with a catalyst system comprising an unsymmetrical metallocene compound, a hydrocarbon soluble activator compound, and a non-aromatic-hydrocarbon solvent in a polymerization reactor under polymerization conditions; and obtaining an unsaturated PAO product comprising vinylidenes, optional tri-substituted vinylenes, optional di-substituted vinylenes, and optional vinyls or vinylidenes, tri-substituted vinylenes, optional di-substituted vinylenes, and optional vinyls.

DETAILED DESCRIPTION

Definitions

The term "alkyl" or "alkyl group" interchangeably refers to a saturated hydrocarbyl group consisting of carbon and hydrogen atoms. An alkyl group can be linear, branched, cyclic, or a combination thereof. Wherever "linear, branched, or cyclic" is used, combinations thereof are included. For example, methylcyclohexyl is a combination, and included in the definition of an alkyl group.

The term "cycloalkyl" or "cycloalkyl group" interchangeably refers to a saturated hydrocarbyl group wherein the carbon atoms form one or more ring structures.

The term "alkenyl" or "alkenyl group" interchangeably refers to a linear unsaturated hydrocarbyl group comprising a C=C bond therein.

The term "cycloalkenyl" or "cycloalkenyl group" interchangeably refers to cyclic hydrocarbyl group comprising a C=C bond in the ring.

The term "aryl" or "aryl group" interchangeably refers to a hydrocarbyl group comprising an aromatic ring structure therein.

The terms "aryloxy" and "aryloxide" mean an aryl group bound to an oxygen atom, such as an aryl ether group/radical connected to an oxygen atom and can include those where the aryl group is a $C_6$ to $C_{20}$ hydrocarbyl. Examples of suitable aryloxy radicals can include phenoxy, biphenoxy, naththoxy, and the like.

The terms "alkoxy" and "alkoxide" mean an alkyl group bound to an oxygen atom, such as an alkyl ether group/radical connected to an oxygen atom and can include those where the alkyl group is a $C_1$ to $C_{20}$ hydrocarbyl. The alkyl group may be straight chain, branched, or cyclic. The alkyl group may be saturated or partially unsaturated. Examples of suitable alkoxy radicals can include methoxy, ethoxy, n-propoxy, iso-propoxy, n-butoxy, iso-butoxy, sec-butoxy, tert-butoxy, and the like.

The terms "hydrocarbyl radical," "hydrocarbyl group," or "hydrocarbyl" interchangeably refers to a group consisting of hydrogen and carbon atoms only. A hydrocarbyl group can be saturated or unsaturated, linear or branched, cyclic or acyclic, aromatic or non-aromatic.

Unless otherwise indicated (such as for substituted hydrocarbyl, etc.), a substituted group means such a group in which at least one atom is replaced by a different atom or a group. For example, a substituted alkyl group can be an alkyl group in which at least one hydrogen atom is replaced by a hydrocarbyl group, a halogen, any other non-hydrogen group, and/or a least one carbon atom and hydrogen atoms bonded thereto is replaced by a different group. Preferably, a substituted group is a radical in which at least one hydrogen atom has been substituted with a heteroatom or heteroatom containing group, preferably with at least one functional group, such as halogen (Cl, Br, I, F), NR*$_2$, OR*, SR*, SeR*, TeR*, PR*$_2$, AsR*$_2$, SbR*$_2$, BR*$_2$, SiR*$_3$, GeR*$_3$, SnR*$_3$, PbR*$_3$, and the like or where at least one heteroatom has been inserted within the hydrocarbyl radical, such as, O, S, Se, Te, NR*, PR*, AsR*, SbR*, BR*, SiR*$_2$, GeR*$_2$, SnR*$_2$, PbR*$_2$, and the like, where R* is, independently, hydrogen, hydrocarbyl, or halocarbyl.

As used herein, aromatic refers to cyclic compounds, ligands or substituents ("ring") that contain cyclic clouds of delocalized pi electrons above and below the plane of the "ring", and the pi clouds must contain a total of 4n+2 pi electrons wherein n is an integer. As used herein, the term "aromatic" also refers to pseudoaromatic heterocycles which are heterocyclic substituents that have similar properties and structures (nearly planar) to aromatic heterocyclic ligands, but are not by definition aromatic.

Substituted hydrocarbyl radicals are radicals in which at least one hydrogen atom has been substituted with a heteroatom or heteroatom containing group, preferably with at least one functional group, such as halogen (Cl, Br, I, F), NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like or where at least one heteroatom has been inserted within the hydrocarbyl radical, such as halogen (Cl, Br, I, F), O, S, Se, Te, NR*, PR*, AsR*, SbR*, BR*, SiR*$_2$, GeR*$_2$, SnR*$_2$, PbR*$_2$, and the like, where R* is, independently, hydrogen or a hydrocarbyl.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl. Also included are isomers of saturated, partially unsaturated and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. Alkyl, alkenyl, and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl, and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

Silyl groups (also referred to as silyl, silyl radicals, and silyl substituents) are defined as SiR*$_3$ where R* is independently a hydrogen, hydrocarbyl or halocarbyl radical, and two or more R* may join together to form a substituted or unsubstituted saturated, partially unsaturated or aromatic cyclic or polycyclic ring structure. Silyl groups are bonded via a silicon atom.

Silylcarbyl radicals (aka, hydrocarbylsilyl groups, also referred to as silylcarbyls, silylcarbyl groups or silylcarbyl substituents) are radicals in which one or more hydrocarbyl hydrogen atoms have been substituted with at least one SiR*$_3$ containing group or where at least one —Si(R*)$_2$— has been inserted within the hydrocarbyl radical where R* is independently a hydrogen, hydrocarbyl or halocarbyl radical, and two or more R* may join together to form a substituted or unsubstituted saturated, partially unsaturated or aromatic cyclic or polycyclic ring structure. Silylcarbyl radicals can be bonded via a silicon atom or a carbon atom.

Substituted silylcarbyl radicals are silylcarbyl radicals in which at least one hydrogen atom has been substituted with at least one functional group such as NR*$_2$, OR*, SeR*, TeR*, PR*$_2$, AsR*$_2$, SbR*$_2$, SR*, BR*$_2$, GeR*$_3$, SnR*$_3$, PbR*$_3$ and the like or where at least one non-hydrocarbon atom or group has been inserted within the silylcarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Ge (R*)$_2$—, —Sn(R*)$_2$—, —Pb(R*)$_2$— and the like, where R* is independently a hydrogen, hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g., F, Cl, Br, I) or halogen-containing group (e.g., CF$_3$).

Substituted halocarbyl radicals are radicals in which at least one halocarbyl hydrogen or halogen atom has been substituted with at least one functional group such as NR*2, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si (R*)$_2$—, —Ge(R*)$_2$—, —Sn(R*)$_2$—, —Pb(R*)$_2$— and the like, where R* is independently a hydrogen, hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

The term "substituted phenyl," or "substituted phenyl group" means a phenyl group having one or more hydrogen groups replaced by a hydrocarbyl, substituted hydrocarbyl, heteroatom or heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SiR*, —SiR*$_3$, —GeR*, —GeR*$_3$, —SnR*, —SnR*$_3$, —PbR*$_3$, and the like, where each R* is independently a hydrocarbyl, halogen, or halocarbyl radical. Preferably the "substituted phenyl" group is represented by the formula:

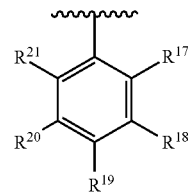

where each of $R^{17}$, $R^{18}$, $R^{19}$, $R^{20}$, and $R^{21}$ is independently selected from hydrogen, $C_1$-$C_{40}$ hydrocarbyl or $C_1$-$C_{40}$ substituted hydrocarbyl, a heteroatom, such as halogen, or a heteroatom-containing group (provided that at least one of $R^{17}$, $R^{18}$, $R^{19}$, $R^{20}$, and $R^{21}$ is not H), or a combination thereof.

A "fluorophenyl" or "fluorophenyl group" is a phenyl group substituted with one, two, three, four or five fluorine atoms.

The term "arylalkyl" means an aryl group where a hydrogen has been replaced with an alkyl or substituted alkyl group. For example, 3,5'-di-tert-butyl-phenyl indenyl is an indene substituted with an arylalkyl group. When an arylalkyl group is a substituent on another group, it is bound to that group via the aryl.

The term "alkylaryl" means an alkyl group where a hydrogen has been replaced with an aryl or substituted aryl group. For example, phenethyl indenyl is an indene substituted with an ethyl group bound to a benzene group. When an alkylaryl group is a substituent on another group, it is bound to that group via the alkyl.

Reference to an alkyl, alkenyl, alkoxide, or aryl group without specifying a particular isomer (e.g., butyl) expressly discloses all isomers (e.g., n-butyl, iso-butyl, sec-butyl, and tert-butyl), unless otherwise indicated.

The term "ring atom" means an atom that is part of a cyclic ring structure. Accordingly, a benzyl group has six ring atoms and tetrahydrofuran has 5 ring atoms.

Reference to an alkyl, alkenyl, alkoxide, or aryl group without specifying a particular isomer (e.g., butyl) expressly discloses all isomers (e.g., n-butyl, iso-butyl, sec-butyl, and tert-butyl), unless otherwise indicated.

The term "Cn" group or compound refers to a group or a compound comprising carbon atoms at total number thereof of n. Thus, a "Cm-Cn" group or compound refers to a group or compound comprising carbon atoms at a total number thereof in the range from m to n. Thus, a $C_1$-$C_{50}$ alkyl group refers to an alkyl group comprising carbon atoms at a total number thereof in the range from 1 to 50.

The term "olefin," alternatively termed "alkene," refers to a substituted or unsubstituted aliphatic hydrocarbon compound having a hydrocarbon chain containing at least one carbon-to-carbon double bond in the structure thereof. The olefin may be linear, branched, or cyclic, or a combination thereof. For purposes of this specification and the claims appended thereto, when a polymer or copolymer is referred to as comprising an olefin, including, but not limited to, ethylene, propylene, and butene, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Thus, an "olefin" is intended to embrace all structural isomeric forms of olefins, unless it is specified to mean a single isomer or the context clearly indicates otherwise. An oligomer is a polymer having a low molecular weight, such as an Mn of 21,000 g/mol or less (preferably 10,000 g/mol or less), and/or a low number of mer units, such as 100 mer units or less (preferably 75 mer units or less).

The term "alpha-olefin" refers to an olefin having a terminal carbon-to-carbon double bond in the structure thereof (R'HC=CH$_2$, where R' can be independently hydrogen or any hydrocarbyl group. Non-limiting examples of α-olefins include ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane.

Cyclic olefins contain a carbon-to-carbon double bond within a ring structure. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, norbornadiene, dicyclopentadiene, 5-ethylidene-2-norbornene, vinylcyclohexene, and 5-vinyl-2-norbornene.

The term "vinyl" means an olefin represented by the following formula:

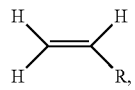

wherein R is a hydrocarbyl group, preferably a saturated hydrocarbyl group such as an alkyl group.

The term "vinylidene" means an olefin represented by the following formula:

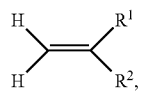

wherein $R^1$ and $R^2$ are each independently a hydrocarbyl group, preferably a saturated hydrocarbyl group such as alkyl group. Vinylidenes are 1,1-di-substituted vinylene groups.

The term "di-substituted vinylene" means:
(i) an olefin represented by the following formula:

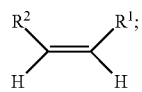

or
(ii) an olefin represented by the following formula:

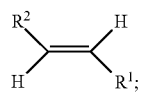

or
(iii) a mixture of (i) and (ii) at any proportion thereof, wherein $R^1$ and $R^2$, the same or different at each occurrence, are each independently a hydrocarbyl group, preferably saturated hydrocarbyl group such as alkyl group. Di-substituted vinylenes represent only 1,2-di-substituted vinylene groups and do not include vinylidenes, or 1,1-di-substituted vinylenes. The term "vinylene," as used herein, is an alternative term for "di-substituted vinylene" only and not as a generic class of multiple vinylene species.

The term "tri-substituted vinylene" means an olefin represented by the following formula:

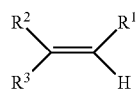

wherein R$^1$, R$^2$, and R$^3$ are each independently a hydrocarbyl group, preferably a saturated hydrocarbyl group such as alkyl group, or alternatively R$^1$ and R$^2$ can together form a non-aryl ring structure with R$^3$ being a pendant hydrocarbyl group.

As used herein, "poly alpha-olefin(s)" (PAO(s)) are polymers of one or more alpha-olefin monomers, particularly an oligomer of one or more alpha-olefins. PAOs are polymeric, typically oligomeric, molecules produced from the polymerization reactions of alpha-olefin monomer molecules in the presence of a catalyst system, optionally further partially or fully hydrogenated to remove residual carbon-carbon double bonds therein or optionally further functionalized by reaction with some or all of the residual carbon-carbon bonds therein. Thus, the PAO can be a dimer, a trimer, a tetramer, or any other oligomer or polymer comprising two or more structure units derived from one or more alpha-olefin monomer(s). The PAO molecule can be highly stereo-regular, such that the bulk material may exhibit an isotacticity, or a syndiotacticity when measured by $^{13}$C NMR. The PAO molecule can be highly stereo-irregular, such that the bulk material can be substantially atactic when measured by $^{13}$C NMR. Typically, tacticity is only relevant for higher viscosity (higher molecular weight) PAO molecules wherein at least triad distributions can be measured by $^{13}$C NMR.

A PAO material made by using a metallocene-based catalyst system is typically referred to as a metallocene-PAO (mPAO), and a PAO material made by using traditional non-metallocene-based catalysts (e.g., Lewis acids, supported chromium oxide, and the like) is typically referred to as a conventional PAO (cPAO).

The term "carbon backbone" refers to the longest straight carbon chain in the molecule of the compound or the group in question. "Branches" or "pendant groups" interchangeably refer to any non-hydrogen group connected to the carbon backbone other than those attached to the carbon atoms at the very ends of the carbon backbone. As used herein, the term "length" of a pendant group is defined as the total number of carbon atoms in the longest carbon chain in the pendant group, counting from the first carbon atom attached to the carbon backbone and ending with the final carbon atom therein, without taking into consideration any substituents or pendant groups on the chain. In some embodiments, the pendant group is free of substituents comprising more than 2 carbon atoms (or more than 1 carbon atom), or is free of any substituent. A pendant group may contain a cyclic group or a portion thereof in the longest carbon chain, in which case half of the carbon atoms in the cyclic group are counted toward the length of the pendant group. Thus, by way of examples, a linear C$_8$ pendant group has a length of 8; each of the pendant groups PG-1 (cyclohexylmethylene) and PG-2 (phenylmethylene) has a length of 4; and each of the pendant groups PG-3 (o-heptylphenylmethylene) and PG-4 (p-heptylphenylmethylene) has a length of 11. Where a PAO molecule contains multiple pendant groups, the arithmetic average of the lengths of all such pendant groups is calculated as the average length of all pendant groups in the PAO molecule.

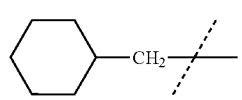

(PG-1)

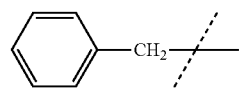

(PG-2)

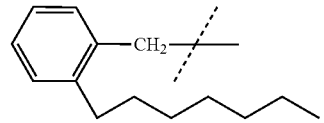

(PG-3)

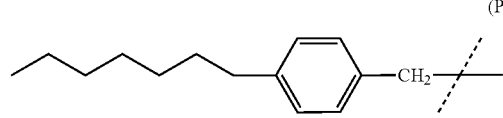

(PG-4)

For nomenclature purposes, the following numbering schemes are used for cyclopentadienyl, indenyl, tetrahydro-s-indacenyl, tetrahydro-as-indacenyl, benz[f]indenyl, benz[e]indenyl ligands.

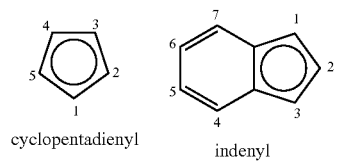

cyclopentadienyl    indenyl

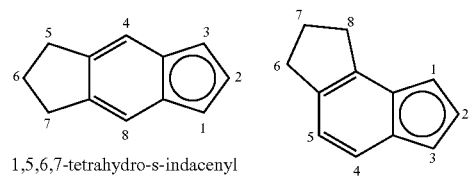

1,5,6,7-tetrahydro-s-indacenyl 3,6,7,8-tetrahydro-as-indacenyl

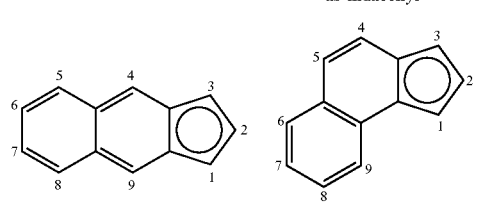

benz[f]indenyl    benz[e]indenyl

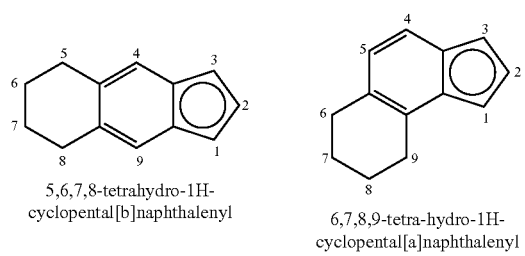

5,6,7,8-tetrahydro-1H-cyclopental[b]naphthalenyl 6,7,8,9-tetra-hydro-1H-cyclopental[a]naphthalenyl In the present invention, any metallocene compound may have one or more optical isomers. All metallocene compound identified herein by name or structure shall include all possible optical isomers thereof and mixtures of any such optical isomers. For example, metallocene compound Me$_2$Si(Me$_4$Cp)(3-PrInd)ZrMe$_2$ shall include the following two optical isomers and mixtures thereof, even if only one structure is given when it is described:

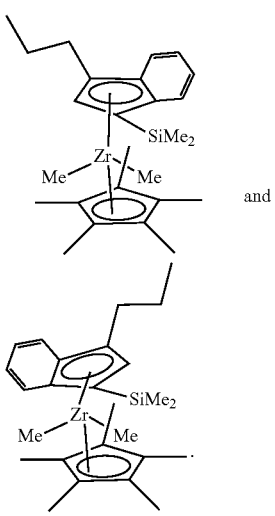

and

A "metallocene" catalyst compound is a transition metal catalyst compound having one, two or three, typically one or two, substituted or unsubstituted cyclopentadienyl ligands bound to the transition metal, typically a metallocene catalyst is an organometallic compound containing at least one n-bound cyclopentadienyl moiety (or substituted cyclopentadienyl moiety). Substituted or unsubstituted cyclopentadienyl ligands include substituted or unsubstituted indenyl, fluorenyl, tetrahydro-s-indacenyl, tetrahydro-as-indacenyl, benz[f]indenyl, benz[e]indenyl, tetrahydrocyclopenta[b]naphthalene, tetrahydrocyclopenta[a]naphthalene, and the like.

An unsymmetrical metallocene compound is a metallocene compound having two π-bound cyclopentadienyl moieties that differ by ring type such as by having one monocyclic arenyl ligand and one polycyclic arenyl ligand. For example, (cyclopentadienyl)(indenyl)zirconium dichloride would be considered unsymmetrical because is has one monocyclic arenyl ligand and one polycyclic arenyl ligand, while bis(indenyl)zirconium dichloride would be considered symmetrical since it has two polycyclic arenyl ligands.

As used herein, the term "monocyclic arenyl ligand" is used herein to mean a substituted or unsubstituted monoanionic $C_5$ to $C_{100}$ hydrocarbyl ligand that contains an aromatic five-membered single hydrocarbyl ring structure (also referred to as a cyclopentadienyl ring).

As used herein, the term "polycyclic arenyl ligand" is used herein to mean a substituted or unsubstituted monoanionic $C_8$ to $C_{103}$ hydrocarbyl ligand that contains an aromatic five-membered hydrocarbyl ring (also referred to as a cyclopentadienyl ring) that is fused to a partially unsaturated, or aromatic hydrocarbyl ring structures which may be fused to additional saturated, partially unsaturated, or aromatic hydrocarbyl rings.

Monocyclic arenyl ligands include substituted or unsubstituted cyclopentadienyls. Polycyclic arenyl ligands include substituted or unsubstituted, partially unsaturated or aromatic indenyls, fluorenyls, benz[f]indenyl, benz[e]indenyl, 5,6,7,8-tetrahydro-1H-cyclopenta[b]naphthalenyl, 6,7,8,9-tetrahydro-1H-cyclopenta[a]naphthalenyls, 1,5,6,7-tetrahydro-s-indacenyl, 3,6,7,8-tetrahydro-as-indacenyl and the like.

Non-limiting examples of polycyclic arene ligands, named also as monoanionic ligands, include indenyl, 4,5-dihydroindenyl, 4,7-dihydroindenyl, 4,5,6,7-tetrahydroindenyl, benz[f]indenyl, benz[e]indenyl, 5,6,7,8-tetrahydro-1H-cyclopenta[b]naphthalenyl, 6,7,8,9-tetrahydro-1H-cyclopenta[a]naphthalenyls, 1,5,6,7-tetrahydro-s-indacenyl, 3,6,7,8-tetrahydro-as-indacenyl, 5,6-trimethyleneindenyl, 4,5-trimethyleneindenyl, 5,6-pentamethyleneindenyl, 4,5-pentamethyleneindenyl, 5,6-hexamethyleneindenyl, 4,5-hexamethyleneindenyl, 5,6-heptamethyleneindenyl, 4,5-heptamethyleneindenyl, 5,6-octamethyleneindenyl, 4,5-octamethyleneindenyl, 5,6-nonamethyleneindenyl, 4,5-nonamethyleneindenyl, 5,6-decamethyleneindenyl, 4,5-decamethyleneindenyl, 5,6-undecamethyleneindenyl, 4,5-undecamethyleneindenyl, 5,6-dodecamethyleneindenyl, 4,5-dodecamethyleneindenyl, 5,6-tridecamethyleneindenyl, 4,5-tridecamethyleneindenyl, 5,6-tetradecamethyleneindenyl, 4,5-tetradecamethyleneindenyl, 5,6-pentadecamethyleneindenyl, 4,5-pentadecamethyleneindenyl, 5,6-hexadecamethyleneindenyl, 4,5-hexadecamethyleneindenyl, 5,6-heptadecamethyleneindenyl, 4,5-heptadecamethyleneindenyl, 5,6-octadecamethyleneindenyl, 4,5-octadecamethyleneindenyl, 5,6-nonadecamethyleneindenyl, 4,5-nonadecamethyleneindenyl, 5,6-eicosamethyleneindenyl, 4,5-eicosamethyleneindenyl, (6Z,8Z,10Z)-cycloocta[e]indenyl, (5Z,7Z,9Z)-cycloocta[f]indenyl, (5E,7Z,9E,11Z,13E)-cyclododeca[f]indenyl, (6E,8Z,10E,12Z,14E)-cyclododeca[e]indenyl.

Partially hydrogenated polycyclic arene ligands retain the numbering scheme of the parent polycyclic arene ligand, namely the numbering schemes defined for indenyl, benz[f]indenyl, benz[e]indenyl, 5,6,7,8-tetrahydro-1H-cyclopenta[b]naphthalenyl, 6,7,8,9-tetrahydro-1H-cyclopenta[a]naphthalenyls, 1,5,6,7-tetrahydro-s-indacenyl, 3,6,7,8-tetrahydro-as-indacenyl.

Unless specified otherwise, the term "substantially all" with respect to PAO molecules means at least 90 mol % (such as at least 95 mol %, at least 98 mol %, at least 99 mol %, or even 100 mol %).

Unless specified otherwise, the term "substantially free of" with respect to a particular component means the concentration of that component in the relevant composition is no greater than 10 mol % (such as no greater than 5 mol %, no greater than 3 mol %, no greater than 1 mol %, or about 0%, within the bounds of the relevant measurement method), based on the total quantity of the relevant composition. Preferably "substantially free of" means no greater than 10 mol % (such as no greater than 5 mol %, no greater than 3 mol %, no greater than 1 mol %, or about 0%, based on the total quantity of the relevant composition.

The terms "catalyst" and "catalyst compound" are defined to mean a compound capable of initiating catalysis and/or of facilitating a chemical reaction. In the description herein, the catalyst may be described as a catalyst precursor, a pre-catalyst compound, or a transition metal compound, and these terms are used interchangeably. When the catalyst compound is combined with an activator to initiate catalysis, the catalyst compound is often referred to as a pre-catalyst or catalyst precursor. A "catalyst system" is combination of at least one catalyst compound, at least one activator, and optional co-activator, where the system can polymerize monomers to form polymer (such as the oligomers escribed herein).

A scavenger is a compound typically added to facilitate oligomerization/polymerization by scavenging impurities. Some scavengers may also act as activators and may be referred to as co-activators. A co-activator, that is not a scavenger, may be used in conjunction with an activator in order to form an active catalyst. In some embodiments, a co-activator can be pre-mixed with the catalyst compound to form an alkylated catalyst compound.

As used herein, a "lubricant" refers to a substance that can be introduced between two or more moving surfaces and lower the level of friction between two adjacent surfaces moving relative to each other. A lubricant "base stock" is a material, typically a fluid at the operating temperature of the lubricant, used to formulate a lubricant by admixing it with other components. Non-limiting examples of base stocks suitable in lubricants include API Group I, Group II, Group III, Group IV, Group V and Group VI base stocks. Fluids derived from Fischer-Tropsch process or Gas-to-Liquid ("GTL") processes are examples of synthetic base stocks useful for making modern lubricants. GTL base stocks and processes for making them can be found, e.g., in PCT Publication No. WO 2005/121280 and in U.S. Pat. Nos. 7,344,631; 6,846,778; 7,241,375; and 7,053,254.

In the present invention, all percentages of pendant groups, terminal carbon chains, and side chain groups are by mole, unless specified otherwise.

Percent by mole is expressed as "mol %," and percent by weight is expressed as "wt %."

In the present invention, all molecular weight data are in the unit of g/mol (also written as g-mol$^{-1}$).

Unless otherwise indicated, proton NMR ($^1$H-NMR) analysis is used to determine the number average molecular weight (Mn) of the polymer materials (including functionalized, hydrogenated, and unhydrogenated PAO materials) prepared herein. In addition, $^1$H-NMR analysis of the unsaturated PAO product can give a quantitative breakdown of the olefinic structure types (viz. vinyl, di-substituted vinylene, tri-substituted vinylene, and vinylidene). In the present invention, compositions of mixtures of olefins comprising terminal olefins (vinyls and vinylidenes) and internal olefins (di-substituted vinylenes and tri-substituted vinylenes) are determined by using $^1$H-NMR as described in the experimental section.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn. Unless otherwise noted, all molecular weight units (e.g., Mw, Mn, Mz) are g/mol (g mol$^{-1}$).

The following abbreviations may be used through this specification: Cp is cyclopentadiene or cyclopentadienyl; Ind is indene or indenyl, Flu is fluorene or fluorenyl, Me is methyl, Et is ethyl, Pr is propyl, iPr is isopropyl, n-Pr is normal propyl, cPr is cyclopropyl, Bu is butyl, nBu is normal butyl, iBu is isobutyl, sBu is sec-butyl, tBu is tertiary butyl, MeCy is methylcyclohexane, and Cy is cyclohexyl, Ph is phenyl, p-tBu is para-tertiary butyl, p-Me is para-methyl, o-biphenyl is an ortho-biphenyl moiety represented by the structure

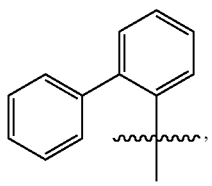 [SMILES: *c1ccccc1-c1ccccc1]

Cbz is Carbazole, Cy is cyclohexyl Oct is octyl, Ar* is 2,6-diisopropylphenyl, Bz or Bn are interchangeably benzyl (i.e., CH$_2$Ph), TMS is trimethylsilyl, TIBAL or TiBAl is triisobutylaluminum, TNOAL or TNOA or TnOAl is tri-n-octylaluminum, MAO is methylalumoxane, THF or thf is tetrahydrofuran, tol or Tol is toluene, dme is 1,2-dimethoxyethane, EtOAc is ethyl acetate, and RT is room temperature (and is 23° C. unless otherwise indicated). The term "continuous" means a system that operates without interruption or cessation for a period of time, such as where reactants are continually fed into a reaction zone and products are continually or regularly withdrawn without stopping the reaction in the reaction zone. For example, a continuous process to produce a polymer would be one where the reactants are continually introduced into one or more reactors and polymer product is continually withdrawn.

A "solution polymerization" means a polymerization process in which the polymerization is conducted in a liquid polymerization medium, such as an inert solvent or monomer(s) or their blends. A solution polymerization is typically homogeneous. A homogeneous polymerization is one where the polymer product is dissolved in the polymerization medium. Such systems are typically not turbid as described in Oliveira, J. V. et al. (2000) "High-Pressure Phase Equilibria for Polypropylene-Hydrocarbon Systems," *Ind. Eng. Chem. Res.*, v. 39(12), pp. 4627-4633.

A bulk polymerization means a polymerization process in which the monomers and/or comonomers being polymerized are used as a solvent or diluent using little or no inert solvent or diluent. A small fraction of inert solvent might be used as a carrier for catalyst and scavenger. A bulk polymerization system contains less than about 25 wt % of inert solvent or diluent, such as less than about 10 wt %, such as less than about 1 wt %, such as 0 wt %.

Description

This invention relates to a process for making a poly alpha-olefin, PAO, comprising contacting a feed containing a C$_6$-C$_{32}$ alpha-olefin with a catalyst system comprising an unsymmetrical metallocene compound and a non-aromatic-hydrocarbon soluble activator in a polymerization reactor under polymerization conditions to obtain PAO comprising vinylidenes, tri-substituted vinylenes, optional di-substituted vinylenes, and optional vinyls; wherein the polymerization reaction preferably exhibits a selectivity toward greater than or equal to about 80 mol % vinylidenes, preferably 90 mol % vinylidenes, preferably 95 mol % vinylidenes, more preferably 96.5 mol % vinylidenes, based on total moles of vinyls, vinylidenes, di-substituted vinylenes, and tri-substituted vinylenes in the unsaturated PAO product.

In some embodiments of the process, the polymerization reaction exhibits a selectivity toward a combination of greater than or equal to about 90 mol % vinylidenes, from 0.5 mol % to 6 mol % tri-substituted vinylenes, less than or equal to about 2.5 mol % di-substituted vinylenes, and less than or equal to about 1.5 mol % vinyls, based on total moles of vinyls, vinylidenes, di-substituted vinylenes, and tri-substituted vinylenes in the unsaturated PAO product.

In particular embodiments of the process, the polymerization reaction exhibits a selectivity toward a combination of vinylidenes of equal to or greater than 95.0 mol %, preferably equal to or greater than 96 mol %, preferably equal to or greater than 97 mol %; tri-substituted vinylenes of less than 2.5 mol %; di-substituted vinylenes of 1.0 mol % or less; and vinyls of 1.5 mol % or less, based on total moles of vinyls, vinylidenes, di-substituted vinylenes, and tri-substituted vinylenes in the unsaturated PAO product. In particular embodiments of the process, the polymerization reaction exhibits a selectivity towards a combination of vinylidenes and tri-substituted vinylenes of collectively greater than 95.0 mol %, preferably greater than 98 mol %, and a combination of di-substituted vinylenes and vinyls of collectively less than 5.0 mol %, preferably less than 2.0 mol %, based on total moles of vinyls, vinylidenes, di-substituted vinylenes, and tri-substituted vinylenes in the unsaturated PAO product.

Preferably, the polymerization reaction exhibits a selectivity toward greater than or equal to about 80 mol % vinylidenes (alternatively greater than or equal to 85 mol % vinylidenes, preferably greater than or equal to 90 mol % vinylideneds), based on total moles of vinyls, vinylidenes, di-substituted vinylenes, and tri-substituted vinylenes in the unsaturated PAO product.

Preferably, the conversion is about 10% or more and the polymerization reaction exhibits a selectivity toward greater than or equal to about 80 mol % vinylidenes (alternatively greater than or equal to 85 mol % vinylidenes, preferably greater than or equal to 90 mol % vinylidenes), based on total moles of vinyls, vinylidenes, di-substituted vinylenes, and tri-substituted vinylenes in the unsaturated PAO product.

Preferably, the polymerization reaction exhibits a selectivity toward a combination of greater than or equal to about 96.5 mol % vinylidenes, from 0.5 mol % to 3.5 mol % tri-substituted vinylenes, less than or equal to about 1.5 mol % di-substituted vinylenes, and less than or equal to about 1.5 mol % vinyls, based on total moles of vinyls, vinylidenes, di-substituted vinylenes, and tri-substituted vinylenes in the unsaturated PAO product.

Preferably, the polymerization reaction exhibits a selectivity toward a combination of vinylidenes of equal to or greater than 97.0 mol %; tri-substituted vinylenes of less than 2.0 mol %; di-substituted vinylenes of 0.5 mol % or less; and vinyls of 1.5 mol % or less, based on total moles of vinyls, vinylidenes, di-substituted vinylenes, and tri-substituted vinylenes in the unsaturated PAO product.

Preferably, the polymerization reaction exhibits a selectivity towards a combination of vinylidenes and tri-substituted vinylenes of collectively greater than 98.0 mol %, and a combination of di-substituted vinylenes and vinyls of collectively less than 2.0 mol %, based on total moles of vinyls, vinylidenes, di-substituted vinylenes, and tri-substituted vinylenes in the unsaturated PAO product.

In some embodiments when the only solvent used is the monomer itself, such as an alpha-olefin monomer, the conversion is about 20% or more and the polymerization reaction exhibits a selectivity toward greater than or equal to about 80 mol % vinylidenes (preferably about 85% or greater, more preferably about 90% or greater, most preferably about 95% or greater), based on total moles of vinyls, vinylidenes, di-substituted vinylenes, and tri-substituted vinylenes in the unsaturated PAO product.

In some embodiments of the invention when the polymerization temperature is above 100° C., preferably above 110° C., the conversion is 50% or more and the polymerization reaction exhibits a selectivity toward greater than or equal to about 80 mol % vinylidenes (preferably about 85% or greater, more preferably about 90% or greater, most preferably about 95% or greater), based on total moles of vinyls, vinylidenes, di-substituted vinylenes, and tri-substituted vinylenes in the unsaturated PAO product.

The number average molecular weight (Mn) of the PAO is highly dependent on the molecular weight of the alpha-olefin or mixture of alpha-olefins used. Because of this, in some embodiments, the degree of polymerization (DP) better represents the preferred ranges of PAO molecular weight. DP is defined as the Mn of the PAO divided by the molecular weight of the alpha-olefin used where the PAO Mn is measured by $^1$H NMR. For purposes of this invention the alpha-olefin molecular weight is calculated to be the carbon number of the alpha-olefin multiplied by 14 (the molecular weight of a $CH_2$ unit). For example, for decene which is a $C_{10}$ alpha-olefin, the molecular weight is 140 g/mole. When mixtures of alpha-olefins are used, the DP is calculated from the Mn of the PAO divided by the average molecular weight of the alpha-olefins used where the PAO Mn is measured by $^1$H NMR, and the average molecular weight of the alpha-olefins is calculated from the sum of molecular weights of each alpha-olefin multiplied by the mole fraction of alpha-olefin used in the polymerization. For example, if 50% octene and 50% tetradecene are used in the polymerization, the average molecular weight of the alpha-olefins used would be (0.5×112 g/mol)+(0.5×196 g/mol) which equals 154 g/mole. In some embodiments of the invention the PAO product has a degree of polymerization from 10 to 2, preferably form 7 to 2, more preferably from 4 to 2. In some embodiments of the invention, for example, when a dimer product is preferred, the DP is 2. In other embodiments of the invention, when a trimer product is preferred, the DP is 3.

In some embodiments of the process the polymerization reaction results in the unsaturated PAO product having a number average molecular weight (Mn) of 2500 g/mol or less, preferably 1500 g/mol or less, preferably 1000 g/mol or less, preferably from about 150 to about 1000 g/mol, preferably from about 200 to about 800 g/mol, as measured by $^1$H NMR.

In particular embodiments of the process, the polymerization conditions comprise a reaction temperature from 40° C. to 180° C.; an average activity level of at least 1500 g/mol·hr; the polymerization reaction mixture exhibits an oligomer yield of at least 10%; or a combination thereof.

In some embodiments the process further comprises: a) contacting the unsaturated PAO product with hydrogen to convert at least a portion of the unsaturated PAO product to a hydrogenated PAO product; or b) contacting the unsaturated PAO product with a chemical reagent to convert at least a portion of the unsaturated PAO product to a functionalized PAO product; or a combination thereof.

In some embodiments the process further comprises: a) contacting the unsaturated PAO product with hydrogen to convert at least a portion of the unsaturated PAO product to a partially hydrogenated PAO product and contacting the unsaturated PAO product with a chemical reagent to convert at least a portion of the unsaturated PAO product to a functionalized PAO product; or a combination thereof.

In some embodiments the process further comprises contacting the unsaturated PAO product with a chemical reagent to convert at least a portion of the unsaturated PAO product to a functionalized PAO product.

In particular embodiments of the process, the feed comprises $C_6$-$C_{24}$ alpha-olefin; and any combination of $C_2$-$C_5$ alpha-olefins are collectively present in the alpha-olefin feed at no higher than 25 mol %, based on the total moles of the alpha-olefins supplied to the polymerization reactor, preferably wherein the alpha-olefin feed is substantially free of ethylene, propylene, $C_4$ alpha-olefins, and $C_5$ alpha-olefins; or a combination thereof. Preferably, the alpha-olefin feed is substantially free (preferably absent, 0 mol %) of propylene, $C_4$ alpha-olefins, and $C_5$ alpha-olefins; or a combination thereof. Optionally, the alpha-olefin feed comprises less than 25 mol %, preferably less than 15 mol %, preferably less than 5 mol % of propylene, $C_4$ alpha-olefins, and $C_5$ alpha-olefins; or a combination thereof.

Optionally, the alpha-olefin feed comprises less than 25 mol %, preferably less than 0.1 to 15 mol %, preferably 1 to 5 mol % of ethylene.

Optionally, the alpha-olefin feed comprises octene. Optionally, the alpha-olefin feed comprises decene. Optionally, the alpha-olefin feed comprises octene, decene and dodecene. Optionally, the alpha-olefin feed comprises octene and dodecene. Optionally, the alpha-olefin feed comprises a single alpha-olefin monomer or a combination of two or more alpha-olefin monomers. Optionally, the alpha-olefin feed comprises a single alpha-olefin monomer selected from the group consisting of: hexene, heptene, octene, nonene, decene, dodecene, tetradecene, and hexadecane. Optionally, the alpha-olefin feed comprises two or more alpha-olefin monomers selected from the group consisting of: hexene, heptene, octene, nonene, decene, dodecene, tetradecene, and hexadecene.

In embodiments of the invention, the unsaturated poly alpha-olefin product comprises greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes contained therein. In particular embodiments, the unsaturated poly alpha-olefin product comprises 96.5 mol % to 99.9 mol % of vinylidenes; 0.1 mol % to 3.5 mol % of tri-substituted vinylenes; 3.0 mol % or less of di-substituted vinylenes; 3.0 mol % or less of vinyl groups; based on total moles of vinylidenes, tri-substituted vinylenes, di-substituted vinylenes, and vinylidenes contained therein; and has a number average molecular weight (Mn) of 1500 g/mol or less as measured by $^1$H NMR.

In particular embodiments, the unsaturated poly alpha-olefin product comprises 96.5 mol % to 99.9 mol % of vinylidenes; 0.1 mol % to 3.5 mol % of tri-substituted vinylenes, di-substituted vinylenes and vinyl groups; based on total moles of vinylidenes, tri-substituted vinylenes, di-substituted vinylenes, and vinylidenes contained therein; and has a number average molecular weight (Mn) of 1500 g/mol or less as measured by $^1$H NMR.

In some embodiments the unsaturated poly alpha-olefin product comprises less than or equal to about 1.0 mol % di-substituted vinylenes; less than or equal to about 1.0 mol % vinyl groups; and has a number average molecular weight (Mn) of 1000 g/mol or less as measured by $^1$H NMR.

In particular embodiments, the unsaturated poly alpha-olefin product comprises from 98 mol % to 99.5 mol % of a combination of vinylidenes and tri-substituted vinylenes; and 0.5 mol % to 2 mol % of a combination of di-substituted vinylenes and vinyl groups, and has a number average molecular weight (Mn) of 800 g/mol or less as measured by $^1$HNMR.

In embodiments of the invention, the catalyst compound useful herein has a polymerization selectivity of greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product.

In particular embodiments, the catalyst compound comprises a polymerization selectivity suitable to form an unsaturated PAO product comprising 96.5 mol % to 99.9 mol % of vinylidenes; 0.1 mol % to 3.5 mol % of tri-substituted vinylenes; 2.0 mol % or less of di-substituted vinylenes; 2.0 mol % or less of vinyl groups; based on total moles of vinyls, vinylidenes, di-substituted vinylenes, and tri-substituted vinylenes in the unsaturated PAO product; and a number average molecular weight (Mn) of 1500 g/mol or less as measured by $^1$H NMR.

I. Unsaturated PAO Product

PAOs are polymeric, typically oligomeric, molecules produced from the polymerization reactions of alpha-olefin monomer molecules in the presence of a catalyst system. An unsaturated poly alpha-olefin (uPAO) molecule in the material of the present invention contains a C=C bond therein. Each uPAO molecule has a carbon chain with the largest number of carbon atoms, which is designated the carbon backbone of the molecule. Any non-hydrogen group attached to the carbon backbone other than to the carbon atoms at the very ends thereof is defined as a pendant group. The number of carbon atoms in the longest carbon chain in each pendant group is defined as the length of the pendant group. The backbone typically comprises the carbon atoms derived from the C=C bonds in the monomer molecules participating in the polymerization reactions, and additional carbon atoms from monomer molecules and/or molecules in the catalyst system that form the two ends of the backbone. A typical unsaturated poly alpha-olefin, uPAO, molecule can be represented by the following Formula (F-1):

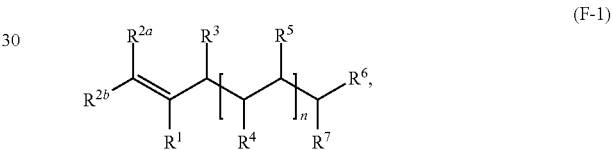

(F-1)

where $R^1$, $R^{2a}$, $R^{2b}$, $R^3$, $R^4$, $R^5$, $R^6$, and $R^7$, the same or different at each occurrence, independently represents a hydrogen or a substituted or unsubstituted hydrocarbyl (preferably an alkyl) group, and n zero or a non-negative integer corresponding to the degree of polymerization, e.g. 1 or more, such as 1, 2, 3, 4, or 5. Where $R^1$, $R^{2a}$ and $R^{2b}$ are all hydrogen, (F-1) represents a vinyl uPAO; where $R^1$ is not hydrogen, and both $R^{2a}$ and $R^{2b}$ are hydrogen, (F-1) represents a vinylidene uPAO; where $R^1$ is hydrogen, and only one of $R^{2a}$ and $R^{2b}$ is hydrogen, (F-1) represents a di-substituted vinylene uPAO; and where $R^1$ is not hydrogen, and only one of $R^{2a}$ and $R^{2b}$ is hydrogen, then (F-1) represents a tri-substituted vinylene uPAO.

Preferably, $R^1$ is not hydrogen, both $R^{2a}$ and $R^{2b}$ are hydrogen and n is 0.

Preferably, the unsaturated PAO product is represented by the following Formula (F-1):

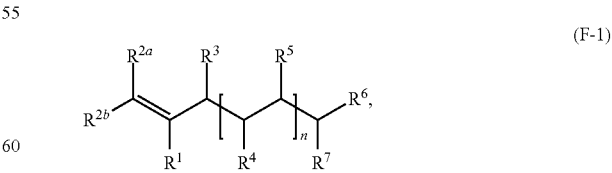

(F-1)

where $R^1$, $R^3$, $R^4$, $R^5$, $R^6$, and $R^7$, are the same or different at each occurrence, and each independently represents a hydrogen or a substituted or unsubstituted hydrocarbyl, both $R^{2a}$ and $R^{2b}$ are hydrogen, n is zero, where $R^1$ is not hydrogen.

When n=0, (F-1) represents an uPAO dimer produced from the reaction of two monomer molecules after a single addition reaction between two C=C bonds.

Thus, when n=1, (F-1) represents a trimer produced from the reactions of three monomer molecules after two steps of linear addition reactions between two C=C bonds.

Assuming a carbon chain starting from $R^1$ and ending with $R^7$ has the largest number of carbon atoms among all straight carbon chains existing in (F-1), that carbon chain starting from $R^1$ and ending with $R^7$ having the largest number of carbon atoms constitutes the carbon backbone of the unsaturated PAO product molecule (F-1). $R^2$, $R^3$, each of $R^4$ and $R^5$, and $R^6$, which can be substituted or unsubstituted hydrocarbyl (preferably alkyl) groups, are pendant groups (if not hydrogen).

If only alpha-olefin monomers are used in the polymerization process, and no isomerization of the monomers and oligomers ever occurs in the reaction system during polymerization, about half, typically at least one more than half, of $R^1$, $R^{2a}$, $R^{2b}$, $R^3$, all $R^4$ and $R^5$, $R^6$, and $R^7$ would be hydrogen, and one of $R^1$, $R^{2a}$, $R^{2b}$, $R^6$, and $R^7$ would be a hydrocarbyl, such as methyl, and about half, typically less than half, of groups $R^1$, $R^{2a}$, $R^{2b}$, $R^3$, all $R^4$ and $R^5$, $R^6$, and $R^7$ would be hydrocarbyl groups introduced from the alpha-olefin monomer molecules. In a specific example of such case, assuming $R^{2a}$ and $R^{2b}$ are hydrogen, $R^3$, all $R^5$, and $R^6$ are hydrogen, and $R^1$, all $R^4$, and $R^7$ have 8 carbon atoms in the longest carbon chains contained therein, and n=8, then the carbon backbone of the (F-1) PAO molecule would comprise 35 carbon atoms, and the average pendant group length of the pendant groups (the initial=$CR^{2a}R^{2b}$ group, and all of $R^4$) would be 7.22 (i.e., (1+8*8)/9). Such an uPAO molecule, which may be produced by polymerizing 1-decene using certain metallocene catalyst systems, such as described in greater detail below, can be represented by Formula (F-2) below:

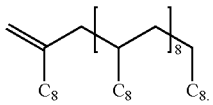

(F-2)

In such a molecule, the longest 5%, 10%, 20%, 40%, 50%, and 100% of the pendant groups have average pendant group length of Lpg(5%) of 8, Lpg(10%) of 8, Lpg(20%) of 8, Lpg(50%) of 8, and Lpg(100%) of 7.22, respectively.

Depending on the polymerization catalyst system used, however, different degrees of isomerization of the monomers and/or oligomers can occur in the reaction system during the polymerization process, resulting in different degrees of substitution on the carbon backbone. In a specific example of such case, assuming $R^{2a}$ and $R^{2b}$ are both hydrogen, $R^3$ and all $R^5$ are methyl, $R^6$ is hydrogen, $R^1$ has 8 carbon atoms in the longest carbon chain contained therein, all $R^4$ and $R^7$ have 7 carbon atoms in the longest carbon chain contained therein, and n=8, then the carbon backbone of the (F-1) uPAO molecule would comprise 34 carbon atoms, and the average pendant group length of the pendant groups (the initial=$CR^{2a}R^{2b}$ group, all $R^4$, and $R^5$) would be ~3.7 (i.e., (1+1+7*8+8*1)/18). Such an uPAO molecule, which may be produced by polymerizing either 1-decene, with a given level and pattern of isomerization, or by polymerizing a combination of 1-decene and 2-decene, using certain non-metallocene catalyst systems, such as described in greater detail below, can be represented by the following Formula (F-3):

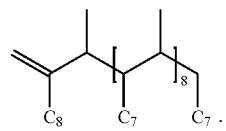

(F-3)

In this molecule, the longest 5%, 10%, 20%, 40%, 50%, and 100% of the pendant groups have average pendant group lengths of Lpg(5%) of 7, Lpg(10%) of 7, Lpg(20%) of 7, Lpg(50%) of 6.3, and Lpg(100%) of 3.7, respectively.

One skilled in the art, with knowledge of the molecular structure or the monomer(s) used in the polymerization step for making the unsaturated PAO product, the process conditions (catalyst used, reaction conditions, etc.), and the polymerization reaction mechanism, inter alia, can approximate the molecular structure of the uPAO molecules, thus the pendant groups attached to the carbon backbone, and hence approximate values of Lpg(5%), Lpg(10%), Lpg(20%), Lpg(50%), and Lpg(100%), respectively.

One skilled in the art can determine the Lpg(5%), Lpg(10%), Lpg(20%), Lpg(50%), and Lpg(100%) values of a given unsaturated PAO product by using separation and characterization techniques available to polymer chemists. For example, gas chromatography/mass spectroscopy machines equipped with boiling point column separator can be used to separate and identify individual chemical species and fractions; and standard characterization methods such as NMR, IR, and UV spectroscopy can be used to further confirm the structures.

In some embodiments of the invention, the uPAO is represented by Formula (F-4):

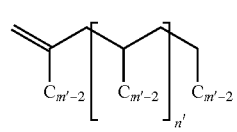

(F-4)

wherein C is a hydrocarbon chain of length m'-2, each m' is independently an integer from 4 to 16 and is the carbon number of the monomer(s) used in the polymerization, for example m' is 8 for octene, 10 for decene, and 12 for dodecene, and n' is an integer from 0 to 10, preferably 0 to 2, and more preferably 0 to 1, and most preferably 0. When n' is zero, the product is a dimer. When n' is one, the product is a trimer.

The unsaturated PAO products of the present invention may be a homopolymer made from a single alpha-olefin monomer or a copolymer made from a combination of two or more alpha-olefin monomers. In some embodiments, the alpha-olefin monomer(s) can include, consist essentially of, or be 1-hexene, 1-octene, 1-decene, 1-dodecene, 1-tetradecene, 1-hexadecene or a combination thereof, such as 1-octene, 1-decene, and 1-dodecene. Preferably, the PAO is a homopolymer of 1-hexene, 1-heptene, 1-octene, 1-nonene, 1-decene, 1-undecene, 1-dodecene, 1-tetradecene, or 1-hexadecene. Alternately, the PAO is a copolymer of decene and one or more of 1-hexene, 1-heptene, 1-octene, 1-nonene, 1-decene, 1-undecene, 1-dodecene, 1-tetradecene, or 1-hexadecene.

The unsaturated PAO products of the present invention may be produced by using a catalyst system comprising a specific type of metallocene compound, such as described in detail herein. The unsaturated PAO products can be substantially free of the alpha-olefin monomer(s), and may advantageously contain vinylidenes at a high concentration, desirably in the range from $c1$ to $c2$ mol % in total, where $c1$ and $c2$ can be, independently, 80, 85, 90, 91, 92, 93, 94, 95, 96, 96.5, 97, 98, 99, 99.5, or 99.9, based on the total moles of vinyls, vinylidenes, di-substituted vinylenes, and tri-substituted vinylenes, as long as $c1<c2$. In particular embodiments, $c1=90$ and $c2=99$; $c1=91$ and $c2=99$; $c1=92$ and $c2=98$; $c1=93$ and $c2=97$; $c1=96.5$ and $c2=99.9$; or $c1=98$ and $c2=99.5$. Without intending to be bound by a particular theory, it is believed that the high concentrations of vinylidenes can be achieved partly by the unique structure of the metallocene compound used in the catalyst system.

Between the vinylidenes and tri-substituted vinylenes in the unsaturated PAO product of the present invention, tri-substituted vinylenes tend to have a considerably lower concentration than the vinylidenes. In some embodiments, the unsaturated PAO products of the present invention can contain a concentration of tri-substituted vinylenes in the range from $c3$ to $c4$ mol %, based on the total moles of the vinyls, vinylidenes, di-substituted vinylenes, and tri-substituted vinylenes, where $c3$ and $c4$ can be, independently, 0, 0.1, 0.5, 1.0, 1.5, 2.0, 2.5, 3.0, 3.5, 4.0, 4.5, 5.0, 5.5 or 6.0, as long as $c3<c4$. In particular embodiments, $c3=0.5$ and $c4=5.5$; $c3=1.0$ and $c4=5.0$; $c3=0.5$ and $c4=4.0$; $c3=0$ and $c4=4.0$; $c3=0.1$ and $c4=3.5$; or $c3=0.5$ and $c4=2$.

In some embodiments, the unsaturated PAO products of the present invention can desirably contain a high combined concentration of vinylidenes and tri-substituted vinylenes, the combined concentration being in the range from $c5$ to $c6$ mol %, based on the total moles of the vinyls, vinylidenes, di-substituted vinylenes, and tri-substituted vinylenes, where $c5$ and $c6$ can be, independently, 85, 90, 91, 92, 93, 94, 95, 96, 97, 98, 99, or 99.5, based on the total moles of vinyls, vinylidenes, di-substituted vinylenes, and tri-substituted vinylenes, as long as $c5<c6$. In particular embodiments, $c5=90$ and $c6=99.5$; $c5=92$ and $c6=99.5$; $c5=94$ and $c6=99$; $c5=95$ and $c6=99$; or $c5=98$ and $c6=99.5$.

Without intending to be bound by a particular theory, it is believed that vinylidenes and tri-substituted vinylenes are more reactive than di-substituted vinylenes when reacted with many functionalizing agents. Thus, the high concentration of vinylidenes, as well as the high combined concentration of vinylidenes plus tri-substituted vinylenes, in the unsaturated PAO products of the present invention may be particularly advantageous if the unsaturated PAO products are used as intermediates for making functionalized PAO products.

The unsaturated PAO products of the present invention can desirably contain di-substituted vinylenes at a low concentration in the range from $c7$ to $c8$ mol %, based on the total moles of vinyls, vinylidenes, di-substituted vinylenes, and tri-substituted vinylenes, where $c7$ and $c8$ can be 0, 0.1, 0.2, 0.3, 0.4, 0.5, 0.6, 0.7, 0.8, 1.0, 1.2, 1.4, 1.6, 1.8, 2.0, 2.5, 3.0, 3.5, 4.0, 4.5, or 5.0, as long as $c7<c8$. In particular embodiments, $c7=0$ and $c8=4.0$; $c7=0$ and $c8=3.0$; $c7=0$ and $c8=2.0$; $c7=0$ and $c8=1$; $c7=0$ and $c8=1.2$; or $c7=0.1$ and $c8=2.5$. Without intending to be bound by a particular theory, it is believed that such low concentrations of di-substituted vinylenes in the unsaturated PAO products are achieved by the low selectivity toward these olefins in the polymerization reactions, which can be enabled at least partially by the unique structure of the metallocene compound in the catalyst system used in the polymerization reaction.

Depending on the metallocene compound used in the catalyst system, the unsaturated PAO products of the present invention can contain vinyls at a low concentration, e.g., from $c9$ to $c10$ mol %, based on the total moles of vinyls, vinylidenes, di-substituted vinylenes, and tri-substituted vinylenes, where $c9$ and $c10$ can be 0, 0.1, 0.2, 0.3, 0.4, 0.5, 0.6, 0.7, 0.8, 1.0, 1.2, 1.4, 1.6, 1.8, 2.0, 2.5, 3.0, 3.5, 4.0, 4.5, or 5.0, as long as $c9<c10$. In particular embodiments, $c9=0$ and $c10=4.0$; $c9=0$ and $c10=3.0$; $c9=0$ and $c10=2$; $c9=0$ and $c10=1.6$; $c9=0$ and $c10=1.0$; or $c9=0.1$ and $c10=1.2$. Without intending to be bound by a particular theory, it is believed that such low concentration of vinyls in the unsaturated PAO products are achieved by the low selectivity toward vinyls in the polymerization reactions, which can be enabled by choosing the molecular structure of the metallocene compound in the catalyst system used in the polymerization reaction.

In some embodiments, the unsaturated PAO products of the present invention can desirably contain a low combined concentration of vinyls and di-substituted vinylenes, the combined concentration being in the range from $c11$ to $c12$ mol %, based on the total moles of the vinyls, vinylidenes, di-substituted vinylenes, and tri-substituted vinylenes, where $c11$ and $c12$ can be, independently, 0, 0.1, 0.2, 0.3, 0.4, 0.5, 0.6, 0.7, 0.8, 1.0, 1.2, 1.4, 1.6, 1.8, 2.0, 2.5, 3.0, 3.5, 4.0, 4.5, 5.0, 5.5, or 6.0, as long as $c11<c12$. In particular embodiments, $c11=0$ and $c12=5.0$; $c11=0$ and $c12=4.0$; $c11=0.5$ and $c12=2$; $c11=0.5$ and $c12=4.5$; or $c11=0.8$ and $c12=5.0$.

Thus, the unsaturated PAO products of the present invention can typically comprise a plurality of PAO molecules, which may be the same or different. Each uPAO molecule can comprise a plurality of pendant groups, which may be the same or different, and the longest 5%, 10%, 20%, 40%, 50%, and 100% of the pendant groups of all of the olefin molecules of the unsaturated PAO product have an average pendent group length of Lpg(5%), Lpg(10%), Lpg(20%), Lpg(40%), Lpg(50%), and Lpg(100%), respectively. It is preferred that at least one of the following conditions are met:

(i) $a1 \leq Lpg(5\%) \leq a2$, where $a1$ and $a2$ can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0 15.5, or 16.0, as long as $a1<a2$;

(ii) $b1 \leq Lpg(10\%) \leq b2$, where $b1$ and $b2$ can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as $b1<b2$;

(iii) $c1 \leq Lpg(20\%) \leq c2$, where $c1$ and $c2$ can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as $c1<c2$;

(iv) $d1 \leq Lpg(40\%) \leq d2$; where $d1$ and $d2$ can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as $d1<d2$;

(v) $e1 \leq Lpg(50\%) \leq e2$; where $e1$ and $e2$ can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, or 14.0, as long as $e1<e2$; and (vi) $f1 \leq Lpg(100\%) \leq f2$, where $f1$ and $f2$ can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, or 13.0, as long as $f1<f2$.

In some embodiments, at least 60% of the pendent groups on olefin molecules in the unsaturated PAO product are straight chain alkyls having at least 4 (e.g., at least 6, at least 8, or at least 10) carbon atoms. In particular embodiments, at least 90% of the pendent groups on the olefin molecules in the unsaturated PAO product are straight chain alkyls having at least 4 (e.g., at least 6, at least 8, or at least 10) carbon atoms.

The unsaturated PAO products of the present invention can have viscosity varying in a broad range. For example, the unsaturated PAO product may have a KV100 in a range from 1 to 5,000 cSt, such as 1 to 3,000 cSt, 2 to 2,000 cSt, 2 to 1,000 cSt, 2 to 800 cSt, 2 to 600 cSt, 2 to 500 cSt, 2 to 400 cSt, 2 to 300 cSt, 2 to 200 cSt, or 5 to 100 cSt as determined according to ASTM D445 (100° C.). The exact viscosity of the unsaturated PAO product can be controlled by, e.g., monomer used, polymerization temperature, polymerization reactor residence time, catalyst used, concentration of catalyst used, distillation and separation conditions, and mixing multiple unsaturated PAO products with different viscosity.

In addition, the unsaturated PAO products of the present invention advantageously have a low molecular weight distribution (polydispersity index), Mw/Mn, in the range from about 1.0 to about 5.0 (e.g., from 1.2 to 4.0, from 1.3 to 3.0, from 1.4 to 2.5, from 1.5 to 2.0, or from 1.6 to 1.8). A narrow molecular weight distribution of the uPAO molecules can be achieved by using metallocene-compound-based catalyst systems in the polymerization step under controlled polymerization conditions (temperature fluctuation, residence time, and the like). Such narrow PDI is desirable in that it defines a material with a high degree of homogeneity in molecular weight, molecular size, rheology behavior, viscosity index, and degrading behavior (such as shear stability and oxidation stability). From an olefin mixture with such degree of homogeneity one can produce a functionalized material having a similar degree of homogeneity as well.

In general, the olefin mixture in the unsaturated PAO products of the present invention can have an average molecular weight that can vary widely (and correspondingly, a KV100 that can vary widely). In some embodiments, the uPAO olefin mixture can have a number average molecular weight of Mn, where Mn1≤Mn≤Mn2, where Mn1 and Mn2 can be, independently, 150, 200, 300, 400, 500, 600, 700, 800, 900, 1000, 1100, 1200, 1300, 1400, 1500, 1700, 2000, 2500, 3000, 3500, 4000, 4500, 5000, 6000, 7000, 8,000, 9000, or 10000 g/mol, as long as Mn1<Mn2. In some embodiments, the uPAO olefin mixture can have a number average molecular weight of 3000 g/mol or less, e.g., 2500 g/mol or less, 2000 g/mol or less, 1700 g/mol or less, 1500 g/mol or less, 1400 g/mol or less, 1300 g/mol or less, 1200 g/mol or less, 1100 g/mol or less, 1000 g/mol or less, 900 g/mol or less, 800 g/mol or less, 700 g/mol or less, 650 g/mol or less, 620 g/mol or less, 600 g/mol or less, 520 g/mol or less, 500 g/mol or less, 400 g/mol or less, 380 g/mol or less, 370 g/mol or less, 360 g/mol or less, 350 g/mol or less, 340 g/mol or less, 330 g/mol or less, or 320 g/mol or less; typically, as the product is preferred to exclude olefin monomers but may include dimers and higher mers, the number average molecular weight can optionally be at least 100 g/mol, e.g., at least 150 g/mol or at least 200 g/mol, depending upon the molecular weight of a monomeric feed olefin component.

The unsaturated PAO products of the present invention may additionally comprise saturated hydrocarbons. The saturated hydrocarbons may be produced in situ in the polymerization step of the alpha-olefin for making the unsaturated PAO products, e.g., where the polymerization is conducted in the presence of a hydrogen-containing atmosphere. Alternatively or additionally, the saturated hydrocarbons may be produced by a partial hydrogenation of a portion of the unsaturated PAO product as produced from the polymerization step. Further additionally or alternatively, the saturated hydrocarbon may be blended with an olefin mixture to obtain a mixture of desired property and composition. Nonetheless, it is desired that the unsaturated PAO products of the present invention comprise the vinylidenes, tri-substituted vinylenes, optional vinyls and optional di-substituted vinylenes at a total concentration thereof of at least 50 wt % (e.g., at least 60, 65, 70, 75, 80, 85, 90, 91, 92, 93, 94, 95, 96, 97, 98, 99, 99.5, or 99.8 wt %), based on total weight of the unsaturated PAO product.

In general, it is desired that the unsaturated PAO product of the present invention has a bromine number in a range from Nb(PAO)1 to Nb(PAO)2, where Nb(PAO)1 and Nb(PAO)2 can be, independently, 1.0, 1.5, 2.0, 2.5, 3.0, 3.5, 4.0, 4.5, 5.0, 6.0, 7.0, 8.0, 9.0, or even 10.0, 15.0, 10.0, as long as Nb(PAO)1<Nb(PAO)2. Desirably, a great majority, such as at least 80, 85, 90, 95, 98, or even 99 mol % of the molecules in the unsaturated PAO product of the present invention may be unsaturated. Desirably, each unsaturated PAO molecule is capable of addition reaction with one $Br_2$ molecule to obtain a 1,2-dibromo-derivative thereof.

Molecular structures of exemplary vinylidene uPAOs made from a mixture of 1-octene and 1-dodecene alpha-olefin monomers at a molar ratio of 4:1 can be schematically represented by Formula (F-V) as follows, where n can be any integer.

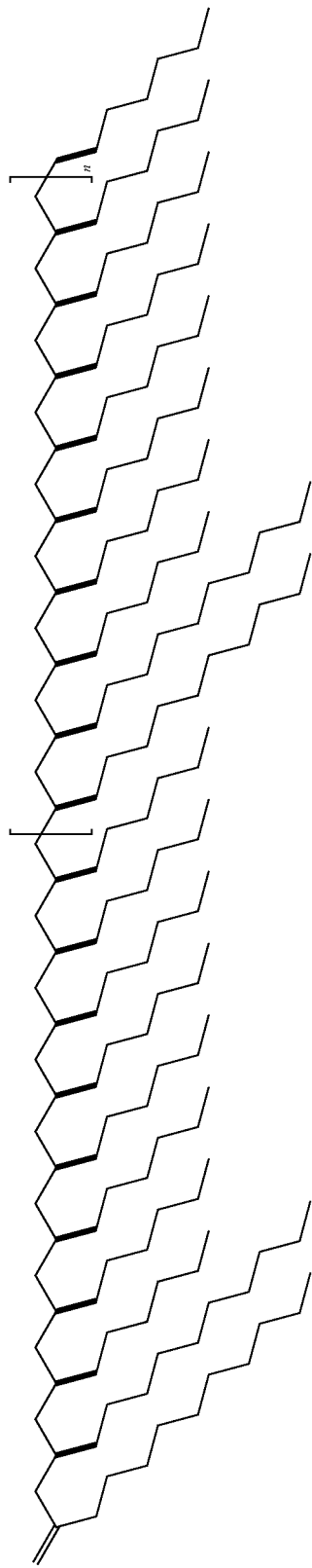

The two $C_{10}$ pendant groups are shown to be next to each other. In real molecules, they may be randomly distributed among all of the pendant groups. The structure shows nearly 100% isotacticity, i.e., 100 mol % of (m,m)-triads in the structure. In real molecules, a small fraction may be (m,r)- or (r,r)-triads. Nonetheless, each of the long pendant groups can extend to form a substantially linear chain, and interact with other long straight carbon chains from other uPAO molecules and other molecules in its vicinity.

Because of the presence of the C═C bonds in the uPAO molecules, when exposed to $O_2$ molecules (such as when exposed to air), the unsaturated PAO product can be oxidized if not protected by a more reactive material toward $O_2$. To that end, in the unsaturated PAO products, anti-oxidant materials may be added to prolong shelf life and facilitate handling, storage, and transportation thereof. Such anti-oxidants can include, but are not limited to, those anti-oxidants typically used in lubricant base stocks and lubricating oil compositions. Non-limiting examples of such anti-oxidants and the use quantity thereof are given in paragraphs [0101]-[0108], pages 9 and 10 of US Patent Publication No. 2010/0087349, the content of which is hereby incorporated by reference in its entirety.

II. Hydrogenation of the Unsaturated PAO Products

The unsaturated PAO products made by the method of the present invention can be directly used as a lubricating oil base stock and other applications because it can be made to have the desired physical properties, particularly rheological properties interesting for such applications. However, due to the presence of C═C bonds on a large portion, if not all, of the uPAO molecules, direct use thereof as a lubricating oil base stock can cause stability issues to the oil if the oil is exposed to an oxidative environment, such as the air. Thus, in general, for lubricating oil applications, it may be desirable to hydrogenate the unsaturated PAO products to remove at least a portion, preferably a major portion, typically all of the C═C bonds of the PAO molecules. For example, one can subject the unsaturated PAO product of the present invention to a step of hydrogenation by contacting it with a hydrogen-containing atmosphere in the presence of a hydrogenation catalyst, such as one containing one or more of Fe, Co, Ni, precious metals (such as Ru, Rh, Pd, Os, Ir, Pt), and the like. Because of the composition of the unsaturated PAO product of the present invention, they can be advantageously hydrogenated to convert a great majority of the C═C bonds present in the olefin molecules into carbon-carbon single bonds, thereby achieving a material that is substantially aliphatic and saturated (e.g., which can be characterized by a low Bromine number of no greater than 5.0, no greater than 4.0, no greater than 3.0, or no greater than 2.0). Such hydrogenated, largely aliphatic hydrocarbon materials can have one or more of high viscosity index, low pour point, high oxidation stability, and high shear stability. They can advantageously be used as, e.g., base stocks for lubricant compositions, such as those used in internal combustion engines, automotive grease oils, industrial grease oils, gear box oils, and the like.

The hydrogenated PAO products made from hydrogenating the unsaturated PAO products can generally exhibit viscosity, molecular weight distribution, pendent group distribution, polydispersity index, that are almost identical with those of precursor unsaturated PAO products. Thus, the hydrogenated PAO products of the present invention can have a KV100 in a range from 1 to 5,000 cSt, such as 1 to 3,000 cSt, 2 to 2,000 cSt, 2 to 1,000 cSt, 2 to 800 cSt, 2 to 600 cSt, 2 to 500 cSt, 2 to 400 cSt, 2 to 300 cSt, 2 to 200 cSt, or 5 to 100 cSt, as determined according to ASTM D445 (100° C.).

The hydrogenated PAO products of the present invention can advantageously have a low polydispersity index (PDI, Mw/Mn) in the range from about 1.0 to about 5.0 (e.g., from 1.2 to 4.0, from 1.3 to 3.0, from 1.4 to 2.5, from 1.5 to 2.0, or from 1.6 to 1.8. Such narrow PDI can be desirable, in that it defines a material with a high degree of homogeneity in molecular weight, molecular size, rheology behavior, viscosity index, and degrading behavior (such as shear stability and oxidation stability).

The hydrogenated PAO products of the present invention can have a number average molecular weight of Mn, where Mn1≤Mn≤Mn2, where Mn1 and Mn2 can be, independently, 150, 200, 300, 400, 500, 600, 700, 800, 900, 1000, 1100, 1200, 1300, 1400, 1500, 1700, 2000, 2500, 3000, 3500, 4000, 4500, 5000, 6000, 7000, 8,000, 9000, or 10000, as long as Mn1<Mn2. In some embodiments, the hydrogenated PAO product can have a number average molecular weight of 3000 g/mol or less, e.g., 2500 g/mol or less, 2000 g/mol or less, 1700 g/mol or less, 1500 g/mol or less, 1400 g/mol or less, 1300 g/mol or less, 1200 g/mol or less, 1100 g/mol or less, 1000 g/mol or less, 900 g/mol or less, 800 g/mol or less, 700 g/mol or less, 600 g/mol or less, or 500 g/mol or less; typically, as the product is preferred to exclude olefin monomers but may include dimers and higher mers, the number average molecular weight can optionally be at least 100 g/mol, e.g., at least 150 g/mol or at least 200 g/mol, depending upon the molecular weight of a monomeric feed olefin component.

The hydrogenated PAO can be used as a high-quality API Group IV base stock. Various grades of the hydrogenated mPAO with KV100 varying from very low such as 1 cSt to very high such as 5,000 cSt can be made by using the method of the present invention, and used for blending with each other and other API Group I, II, III, IV, or V base stocks to make high-quality lubricating oil formulations, such as internal combustion engine oils, automobile drive line oils, industrial oils, greases, and the like. Furthermore, the mPAO can be used as heat transfer oil (e.g., transformer oil), processing oil, hydraulic power transfer oil, and the like.

III. Functionalization of the Unsaturated PAO Products

The unsaturated PAO products of the present invention as described above, desirably produced by polymerization of alpha-olefin and/or olefinic monomers in the presence of a metallocene-compound-based catalyst system, can be advantageously used as a chemical intermediate for making many products, especially those comprising a PAO molecule moiety and one or more functional groups. The hydrocarbon molecules in the unsaturated PAO products, if prepared from the polymerization of olefins/alpha-olefins containing only one C═C double bond in their pre-polymerized molecules, can tend to comprise no more than one C═C bond each, with the rest of the molecular structure typically consisting of C—C bonds and C—H bonds.

The C═C bonds present in the molecules of the unsaturated PAO product of the present invention are highly reactive, and therefore can react with multiple, different types of chemical agents having useful functional groups, thereby creating a PAO molecule further comprising a functional group bonded thereto. The functional group can comprise, in turn, other functional groups, which can react with additional chemical agents, bringing additional or different functional groups to the final molecule. The hydrocarbon substrate (i.e., the PAO structure) of thus functionalized PAO can impart desired properties to the functionalized material, such as solubility in organic media or hydrophobicity, and the functional groups can impart other desired properties to the final material, such as polarity, hydrophilicity (thus, solubility in aqueous media), and the like, making the final material particularly useful where such dual properties are desired (e.g., detergents, adhesives, etc.).

US Publication No. 2014/0087986 discloses multiple methods for making functionalized PAO from unsaturated PAO products produced by polymerization of alpha-olefin monomers in the presence of a metallocene-compound-based catalyst system. The entirety of the invention of US 2014/0087986 is incorporated by reference herein.

It is highly desired that upon functionalization of the unsaturated PAO product, the C=C double bond in the reacted uPAO molecule becomes saturated (i.e., each carbon atom in the original C=C bond is then bonded to four atoms). This can be achieved by using functionalization agents reactive substantially only toward the C=C bonds, but substantially inert toward the C—C bonds and C—H bonds in the uPAO olefin molecules under the functionalization conditions. Given that each uPAO olefin molecule comprises typically only one C=C bond, the uPAO olefin molecule would then become saturated upon such functionalization reaction.

Upon functionalization of the C=C bond in the uPAO olefin molecule, the overall structure of the functionalized PAO molecule would be substantially similar to that of a hydrogenated PAO molecule where the C=C bond has been saturated by hydrogenation as described above. Assuming that the bond between the functional group(s) to the carbon atom(s) is not significantly less robust than the C—C and C—H bonds, and assuming the functional group(s) per se are not significantly less robust than a pendant group on the PAO molecule under the use conditions, one can expect a stable oligomeric/polymeric structure retaining at least some of the interesting and useful properties of a saturated PAO molecule, such as one or more of viscosity index, oxidation stability, shear stability, Bromine number, and the like. The retained properties can make the functionalized PAO material particularly useful in applications typical for the saturated PAO materials, such as lubricating oil compositions, and the like.

It is highly desirable that the functionalization agent used to functionalize the unsaturated PAO product is highly selective toward reacting with the C=C bond only, and is substantially inert with respect to the C—C bonds and C—H bonds on the uPAO molecules. This can ensure the production of functionalized PAO molecules each comprising one or two functional group(s) only, and a complete functionalization of substantially all of the uPAO molecules if desired. In applications such as lubricating oil compositions, because of the high reactivity of C=C bonds in the uPAO molecules, it may be desired that substantially all of the C=C bonds in the uPAO molecules are saturated before the functionalized PAO material is put into the oil compositions, either as a base stock or as an additive.

Additionally or alternatively, one may also functionalize the uPAO molecules by substituting one or more of the hydrogen atoms on the carbon backbone or one of the pendant groups with a functional group by using chemical agents known to be reactive with C—H bonds. Because a uPAO molecule typically comprise many C—H bonds at multiple locations, such reaction would be less selective than selective functionalization of C=C bonds by using a functionalization agent that is inert to the C—H bonds, and can result in very large number of very different molecules, and thus is less desirable than functionalization selective toward the C=C bonds only.

Additionally or alternatively, the uPAO products of the present invention can be functionalized by reaction between the unsaturated C=C bonds of the uPAO molecules and a chemical reagent. The chemical reagent may contain the moiety to be directly or indirectly reacted with the reactive portion(s) of the uPAO, optionally in the presence of an appropriate catalyst or facilitating agent. Alternatively, the chemical reagent may be a precursor to be directly or indirectly reacted with the reactive portion(s) of the uPAO, optionally in the presence of an appropriate catalyst or facilitating agent, followed by at least one other treatment and/or chemical reagent reaction, also optionally in the presence of the same or a different appropriate catalyst or facilitating agent, in order to effectuate a desired final functionality at the reactive portion(s) of the uPAO. Further alternatively, the chemical reagent may be a co-reactant to be pre-reacted or simultaneously reacted with another chemical reagent for direct or indirect reaction with the reactive portion(s) of the uPAO, optionally in the presence of an appropriate catalyst or facilitating agent.

Optionally, more than one type of functionality can be desired, such that the functionalization can occur simultaneously (effectuating a variety of functionalities in a single result), in series, in parallel (provided two parallel reactions do not countermand each other), or some combination thereof. Whether one or more functionalities are desired, the reaction can be of any variety capable of effectively accomplishing the functionalization, e.g., liquid-phase chemistry, gas-liquid interfacial chemistry, solid-liquid surface chemistry, gaseous oxidation, gaseous oxidation followed by some other functionalization mechanism, plasma oxidation, plasma oxidation followed by some other functionalization mechanism, radical formation, radical formation followed by some other functionalization mechanism, or the like. The ultimately desired functional group(s) can be tailored to the particular end-use application, e.g., including but not limited to moieties containing an oxygen atom, a nitrogen atom, a sulfur atom, a phosphorus atom, a boron atom, a silicon atom, a halogen atom, or a combination thereof. The extent to which functionalization can be accomplished is another variable that can be tailored to the particular end-use application. Functionalization (single or multiple) can be partial or substantially complete (i.e., in which substantially all the unsaturations of the uPAO can be converted into a functional moiety, such as a heteroatom-containing moiety).

The PAOs prepared herein may be functionalized by reacting a hereroatom containing group with the PAO with or without a catalyst. Examples include catalytic hydrosilylation, ozonolysis, hydroformylation, or hydroamination, sulfonation, halogenation, hydrohalogenation, hydroboration, epoxidation, or Diels-Alder reactions with polar dienes, Friedel-Crafts reactions with polar aromatics, maleation with activators such as free radical generators (e.g. peroxides). The functionalized PAO's can be used in oil additives, as antifogging or wetting additives, surfactants for soaps, detergents, fabric softeners, antistatics, adhesion promoters and many other applications. Preferred uses include additives for lubricants and or fuels, preferably where the heteroatom containing group includes one or more of amines, aldehydes, alcohols, acids, anhydrides, sulphonates, particularly succinic acid, maleic acid and maleic anhydride.

In some embodiments the PAO's produced herein are functionalized as described in U.S. Pat. No. 6,022,929;

Toyota, A. et al. (2002) *Polymer Bulletin*, v. 48(3), pp. 213-219; and Kropp, P. J. (1990) *Journal Am. Chem. Soc.*, v. 112, pp. 7433-7434. In some embodiments the functionalized PAO's produced herein are further functionalized (derivatized), such as described in U.S. Pat. No. 6,022,929; Toyota, A. et al. (2002) *Polymer Bulletin*, v. 48(3), pp. 213-219; Kropp, P. J. (1990) *Journal Am. Chem. Soc.*, v. 112, pp. 7433-7434; and WO 2009/155472.

In preferred embodiments, the PAO's of the present invention can be functionalized (e.g. chemically modified with one or more functional groups (also referred to as a heteroatom containing group) typically containing heteroatoms such as P, O, S, N, Br, Cl, F, I and or Br (preferably N, O, Cl and or Br, preferably N and or O). Preferred functional groups are selected from the group consisting of acids, esters, anhydrides, acid-esters, oxycarbonyls, carbonyls, formyls, formylcarbonyls, hydroxyls, and acetyl halides. Particularly preferred functional groups include those represented by the formula: —C(O)—X, where the O is double bonded to the C and the X is hydrogen, nitrogen, hydroxy, oxyhydrocarbyl (e.g. ester), oxygen, the salt moiety —OM wherein M is a metal, e.g. alkali, alkaline earth, transition metal, copper, zinc and the like, oxyhetero, e.g. —O—Z wherein Z represents a heteroatom such as phosphorus boron, sulfur, which heteroatom may be substituted with hydrocarbyl or oxyhydrocarbyl groups, or two acyl groups may be joined through (X).

Preferred heteroatom containing groups include acyl groups derived from monounsaturated mono- or dicarboxylic acids and their derivatives, e.g. esters and salts.

More specifically, PAO's functionalized with mono- or dicarboxylic acid material, i.e., acid, anhydride, salt or acid ester are preferred, including the reaction product of the PAO with a monounsaturated carboxylic reactant comprising at least one member selected from the group consisting of (i) monounsaturated $C_4$ to $C_{10}$ dicarboxylic acid (preferably wherein (a) the carboxyl groups are vicinyl, (i.e. located on adjacent carbon atoms) and (b) at least one, preferably both, of said adjacent carbon atoms are part of said monounsaturation); (ii) derivatives of (i) such as anhydrides or $C_1$ to $C_5$ alcohol derived mono- or diesters of (i); (iii) monounsaturated $C_3$ to $C_{10}$ monocarboxylic acid wherein the carbon-carbon double bond is conjugated to the carboxyl group, i.e., of the structure —C═C—C(O)— (where O is double bonded to C), and (iv) derivatives of (iii) such as $C_1$ to $C_5$ alcohol derived monoesters of (iii). Upon reaction with the PAO, the double bond of the monounsaturated carboxylic reactant becomes saturated. Thus, for example, maleic anhydride reacted with the PAO becomes succinic anhydride, and acrylic acid becomes a propionic acid.

Suitable unsaturated acid materials thereof which are useful functional compounds, include acrylic acid, crotonic acid, methacrylic acid, maleic acid, maleic anhydride, fumaric acid, itaconic acid, itaconic anhydride, citraconic acid, citraconic anhydride, mesaconic acid, glutaconic acid, chloromaleic acid, aconitic acid, crotonic acid, methylcrotonic acid, sorbic acid, 3-hexenoic acid, 10-decenoic acid, 2-pentene-1,3,5-tricarboxylic acid, cinnamic acid, and lower alkyl (e.g. $C_1$ to $C_4$ alkyl) acid esters of the foregoing, e.g. methyl maleate, ethyl fumarate, methyl fumarate, etc. Particularly preferred are the unsaturated dicarboxylic acids and their derivatives, especially maleic acid, fumaric acid and maleic anhydride.

Typically, from about 0.7 to about 4.0 (e.g., 0.8 to 2.6), preferably from about 1.0 to about 2.0, and most preferably from about 1.1 to about 1.7 moles of said monounsaturated carboxylic reactant are charged to the reactor per mole of PAO charged.

Functionalization can be achieved by any suitable method. Useful methods include the reaction of an olefinic bond of the PAO with an unsaturated, preferably a monounsaturated, carboxylic reactant. Alternatively, the oligomer can be halogenated using chlorine or bromine-containing compounds. The halogenated PAO can then be reacted with the monounsaturated carboxylic acid. The PAO and the monounsaturated carboxylic reactant can also be contacted at elevated temperatures to cause a thermal "ene" reaction to take place. Alternatively, the monounsaturated carboxylic acid can be reacted with the PAO by free radical induced grafting. The PAO of the present invention can be functionalized by contact with a hydroxy aromatic compound in the presence of a catalytically effective amount of at least one acidic alkylation catalyst. The alkylated hydroxy aromatic compound can then be further reacted to form a derivative by Mannich Base condensation with an aldehyde and an amine reagent to yield a Mannich Base condensate. In yet another means to functionalize the PAO, the PAO may be contacted with carbon monoxide in the presence of an acid catalyst under Koch reaction conditions to yield the PAO substituted with carboxylic acid groups. In addition to the above methods of functionalization, the PAO of the present invention can be functionalized by methods of air oxidation, ozonolysis, hydroformylation, epoxidation and chloroamination. (For more information please see U.S. Pat. No. 6,022,929 Column 21, line 16 to column 33, line 27.)

The polyalpha-olefins produced herein contain one or more unsaturated double bonds, rich in vinylidene content with some 1,2-disubstituted olefins. These unsaturated polymers are particularly suitable for further functionalization reactions. Examples of such functionalization includes alkylation with aromatics compounds, such as benzene, toluene, xylene, naphthalene, phenol or alkylphenols. The PAO's can also react with maleic anhydride to give PAO—succinic anhydride, which can be further converted with amines or alcohols to corresponding succinimide or succinate esters. These imides and esters are superior dispersants.

The functionalized PAO can in turn be derivatized with a derivatizing compound. (For purposes of this invention and the claims thereto the term functionalized PAO encompasses derivatized PAO.) The derivatizing compound can react with the functional groups of the functionalized PAO by means such as nucleophilic substitution, Mannich Base condensation, and the like. The derivatizing compound can be polar and/or contain reactive derivative groups. Preferred derivatizing compounds are selected from hydroxy containing compounds, amines, metal salts, anhydride containing compounds and acetyl halide containing compounds. The derivatizing compounds can comprise at least one nucleophilic group and preferably at least two nucleophilic groups. A typical derivatized PAO is made by contacting a functionalized PAO, i.e., substituted with a carboxylic acid/anhydride or ester, with a nucleophilic reagent, e.g., amine, alcohol, including polyols, amino alcohols, reactive metal compounds and the like. (For more information please see U.S. Pat. No. 6,022,929 column 33, line 27 to column 74, line 63.) Alternately a derivatized PAO may be made by contacting a functionalized PAO, substituted with a carboxylic acid/anhydride or ester, with a nucleophilic reagent, e.g., amine, to make a quaternary ammonium compound or amine oxide.

The functionalized PAO's and/or derivatized PAO's have uses as lubricating additives which can act as dispersants, viscosity index improvers, or multifunctional viscosity index improvers. Additionally they may be used as disinfectants (functionalized amines) and or wetting agents.

The functionalized PAO prepared herein may be used in oil additivation, lubricants, fuels and many other applications. Preferred uses include additives for lubricants and or fuels.

In particular embodiments herein, the PAO's disclosed herein, or functionalized/derivatized analogs thereof, are useful as additives, preferably in a lubricant.

The functionalized PAO's and/or derivatized PAO's produced herein have uses as lubricating additives which can act as dispersants, viscosity index improvers, or multifunctional viscosity index improvers. Additionally they may be used as disinfectants (functionalized amines) and or wetting agents.

The functionalized PAOs and/or derivatized PAOs described herein are useful for viscosity index improvers for lubricating oil compositions, adhesive additives, antifogging and wetting agents, ink and paint adhesion promoters, coatings, tackifiers and sealants, and the like. In addition, such PAOs may be functionalized and derivatized to make multifunctional viscosity index improvers which also possess dispersant properties. (For more information please see U.S. Pat. No. 6,022,929.)

The functionalized PAOs and/or derivatized PAOs described herein may be combined with other additives (such as viscosity index improvers, corrosion inhibitor, oxidation inhibitor, dispersant, lube oil flow improver, detergents, demulsifiers, rust inhibitors, pour point depressant, anti-foaming agents, antiwear agents, seal swellant, friction modifiers, and the like (described for example in U.S. Pat. No. 6,022,929 at columns 60, line 42-column 78, line 54 and the references cited therein) to form compositions for many applications, including but not limited to lube oil additive packages, lube oils, and the like.

Compositions containing these additives are typically are blended into a base oil in amounts which are effective to provide their normal attendant function. Representative effective amounts of such additives are illustrated as follows:

| Compositions | (Typical) wt %* | (Preferred) wt %* |
| --- | --- | --- |
| V.I. Improver | 1-12 | 1-4 |
| Corrosion Inhibitor | 0.01-3 | 0.01-1.5 |
| Oxidation Inhibitor | 0.01-5 | 0.01-1.5 |
| Dispersant | 0.1-10 | 0.1-5 |
| Lube Oil Flow Improver | 0.01-2 | 0.01-1.5 |
| Detergents and Rust inhibitors | 0.01-6 | 0.01-3 |
| Pour Point Depressant | 0.01-1.5 | 0.01-1.5 |
| Anti-Foaming Agents | 0.001-0.1 | 0.001-0.01 |
| Antiwear Agents | 0.001-5 | 0.001-1.5 |
| Seal Swellant | 0.1-8 | 0.1-4 |
| Friction Modifiers | 0.01-3 | 0.01-1.5 |
| Lubricating Base Oil | Balance | Balance |

*Wt %'s are based on active ingredient content of the additive, and/or upon the total weight of any additive-package, or formulation which will be the sum of the A.I. weight of each additive plus the weight of total oil or diluent.

When other additives are employed, it may be desirable, although not necessary, to prepare additive concentrates comprising concentrated solutions or dispersions of the subject additives of this invention (in concentrate amounts hereinabove described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The subject functionalized or derivatized PAOs of the present invention can be added to small amounts of base oil or other compatible solvents along with other desirable additives to form additive-packages containing active ingredients in collective amounts of typically from about 2.5 to about 90%, and preferably from about 15 to about 75%, and most preferably from about 25 to about 60% by weight additives in the appropriate proportions with the remainder being base oil.

The final formulations may employ typically about 10 wt % of the additive-package with the remainder being base oil.

In another embodiment, the PAO's described herein can be use in any process, blend or product disclosed in WO 2009/0155472 or U.S. Pat. No. 6,022,929, which are incorporated by reference herein.

In a preferred embodiment, this invention relates to a fuel comprising any PAO produced herein. In a preferred embodiment, this invention relates to a lubricant comprising any PAO produced herein.

IV. The Catalyst System

The catalyst system useful herein comprises an unsymmetric metallocene catalyst compound activated by one or more non-aromatic-hydrocarbon soluble activators, and may further include a solvent, a support, one or more scavengers, and/or the like.

The typical activator-to-catalyst ratio, e.g., all NCA activators-to-catalyst ratio is about a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

Solvents useful for combining the catalyst compound and activator and/or for introducing the catalyst system into the reactor, include, but are not limited to, aliphatic solvents, such as butanes, pentanes, hexanes, heptanes, octanes, nonanes, decanes, undecanes, dodecanes, tridecanes, tetradecanes, pentadecanes, hexadecanes, or a combination thereof; preferable solvents can include normal paraffins (such as NORPAR® solvents available from ExxonMobil Chemical Company in Houston, TX), isoparaffin solvents (such as ISOPAR® solvents available from ExxonMobil Chemical Company in Houston, TX), and combinations thereof. These solvents or diluents may typically be pretreated in same manners as the feed olefins.

Preferably the solvent is selected from $C_4$ to $C_{10}$ linear, branched or cyclic alkanes.

Preferably the solvent is essentially free of all aromatic solvents.

Preferably the solvent is essentially free of toluene.

Preferably the solvent is selected from one or more $C_6$ to $C_{32}$ alpha olefins, such as one or more $C_8$ to $C_{16}$ alpha olefins.

Preferably the solvent is essentially free of all non-alpha-olefin solvents.

Useful aliphatic hydrocarbon solvent can be isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In at least one embodiment, aromatics are present in the solvent at less than 1 wt %, such as less than 0.5 wt %, such as at 0 wt % based upon the weight of the solvents.

The activators of the present disclosure can be dissolved in one or more additional solvents provided such solvents are non-aromatic. Additional solvent includes halogenated or partially halogenated hydrocarbons solvents.

In at least one embodiment, the aliphatic solvent is isohexane and/or methylcyclohexane.

In at least one embodiment, the solvent is one or more $C_6$ to $C_{32}$ alpha olefins, such as one or more $C_8$ to $C_{16}$ alpha olefins, and no additional solvents are used.

In at least one embodiment, the solvent is 1-octene, 1-decene, 1-dodecene, or 1-tetradecene, or a combination of any two or more.

IV.1 The Metallocene Compound

Metallocene compounds that are useful herein are unsymmetrical, e.g., having two π-bound cyclopentadienyl moieties that differ by ring type, such as by having one monocyclic arenyl ligand and one polycyclic arenyl ligand.

Unsymmetrical metallocene compounds useful herein included those represented by Formula (I): wherein:

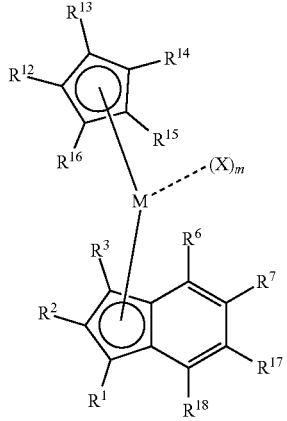

(I)

each $R^1$, $R^2$, and $R^3$ is, independently, hydrogen or a substituted or unsubstituted linear, branched, or cyclic $C_1$-$C_{20}$ hydrocarbyl group, preferably wherein at least one of $R^1$, $R^2$, and $R^3$ not hydrogen and at least one of $R^1$, $R^2$, and $R^3$ is hydrogen;

$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;

$R^{12}$, $R^{13}$, $R^{14}$, and $R^{15}$, are each independently a substituted or unsubstituted linear, branched, or cyclic $C_1$-$C_{20}$ hydrocarbyl group;

$R^{16}$ is a substituted or unsubstituted linear, branched, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;

M is a transition metal, preferably group 3, 4 or 5, having an integer coordination number of v, such as 3, 4, or 5; and m is an integer equal to v-2, such as 1, 2, or 3.

Unsymmetrical metallocene compounds useful herein included those represented by Formula (II):

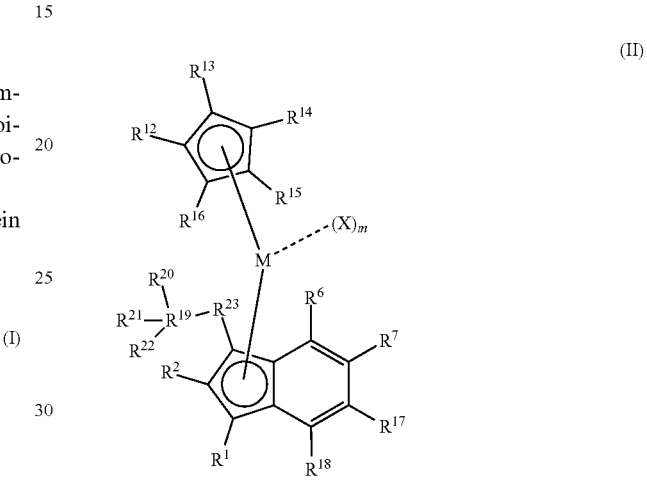

(II)

wherein:
$R^1$ and $R^2$ are hydrogen;
$R^{23}$ and $R^{19}$ comprise group 14 atoms, preferably C, Ge, or Si (preferably $R^{23}$ is C and $R^{19}$ is C or Si);
$R^{20}$, $R^{21}$, and $R^{22}$ are independently hydrogen or a substituted or unsubstituted linear, branched, or cyclic $C_1$-$C_{20}$ hydrocarbyl group and at least two of $R^{20}$, $R^{21}$, and $R^{22}$ are not hydrogen;
$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;
$R^{12}$, $R^{13}$, $R^{14}$, $R^{15}$, and $R^{16}$ are each independently a substituted or unsubstituted linear, branched, or cyclic $C_1$-$C_8$ hydrocarbyl group;
each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or two or more X moieties together form a fused ring or ring system;
M is a group 3, 4, or 5 transition metal having an integer coordination number of v, such as 3, 4 or 5;
and m is an integer equal to v-2, such as 1, 2 or 3.

Unsymmetrical metallocene compounds useful herein included those represented by Formula (III):

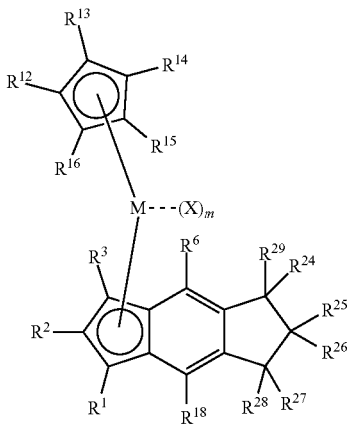

(III)

wherein one of $R^1$ and $R^3$ is a substituted or unsubstituted linear, branched, or cyclic $C_1$-$C_{20}$ hydrocarbyl group;

two of $R^1$, $R^2$, and $R^3$ are each hydrogen;

$R^6$, $R^{18}$, $R^{29}$, $R^{24}$, $R^{25}$, $R^{26}$, $R^{27}$ and $R^{28}$ are each independently hydrogen, a substituted or unsubstituted linear, branched, or cyclic $C_1$-$C_{30}$ hydrocarbyl group, or two of $R^6$, $R^{18}$, $R^{29}$, $R^{24}$, $R^{25}$, $R^{26}$, $R^{27}$ and $R^{28}$ taken together with the carbon atoms in the cyclopentan-indenyl ring to which they are directly connected, collectively form one or more substituted or unsubstituted rings annelated to the cyclopentan-indenyl ring;

$R^{12}$, $R^{13}$, $R^{14}$, $R^{15}$, and $R^{16}$ are each independently a substituted or unsubstituted linear, branched, or cyclic $C_1$-$C_{20}$ hydrocarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;

M is a group 3, 4, or 5 transition metal having an integer coordination number of v, such as 3, 4, or 5;

and m is an integer equal to v-2, such as 1, 2, or 3.

Unsymmetrical metallocene compounds useful herein included those represented by Formula (IV):

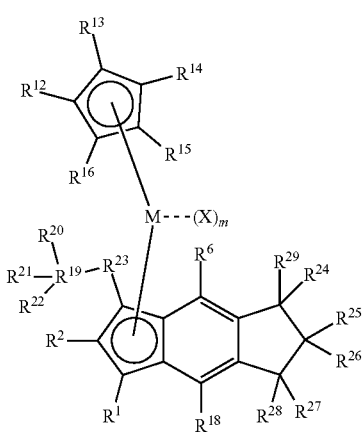

(IV)

wherein:
$R^1$ and $R^2$ are hydrogen;
$R^{23}$ and $R^{19}$ comprise Group 14 atoms, preferably C, Ge, or Si (preferably $R^{23}$ is C and $R^{19}$ is C or Si);
$R^{20}$, $R^{21}$, and $R^{22}$ are independently hydrogen or a substituted or unsubstituted linear, branched, or cyclic $C_1$-$C_{20}$ hydrocarbyl group and at least two of $R^{20}$, $R^{21}$, and $R^{22}$ are not hydrogen;
$R^6$, $R^{18}$, $R^{29}$, $R^{24}$, $R^{25}$, $R^{26}$, $R^{27}$ and $R^{28}$ are each independently hydrogen, a substituted or unsubstituted linear, branched, or cyclic $C_1$-$C_{30}$ hydrocarbyl group, or two of $R^6$, $R^{18}$, $R^{29}$, $R^{24}$, $R^{25}$, $R^{26}$, $R^{27}$ and $R^{28}$ taken together with the carbon atoms in the cyclopentan-indenyl ring to which they are directly connected, collectively form one or more substituted or unsubstituted rings annelated to the cyclopentan-indenyl ring;
$R^{12}$, $R^{13}$, $R^{14}$, $R^{15}$, and $R^{16}$ are each independently a substituted or unsubstituted linear, branched, or cyclic $C_1$-$C_{20}$ hydrocarbyl group;
each X is independently a halogen, a hydride, an amide, an alkoxide, a sulfide, a phosphide, a diene, an amine, a phosphine, an ether, a $C_1$-$C_{20}$ substituted or unsubstituted linear, branched, or cyclic hydrocarbyl group, or two or more X moieties together form a fused ring or ring system;
M is a group 3, 4, or 5 transition metal having an integer coordination number of v, such as 3, 4, or 5;
and m is an integer equal to v-2, such as 1, 2, or 3.

Optionally, in any embodiment of Formula (I) or (III) herein, $R^2$ is hydrogen and one of $R^1$ and $R^3$ is a substituted or unsubstituted linear, branched, or cyclic $C_1$-$C_6$ hydrocarbyl group, and the other one of $R^1$ and $R^3$ is a hydrogen.

Optionally, in any embodiment of Formula (I) or (II) herein, $R^6$ and $R^7$, or $R^7$ and $R^{17}$, or $R^{17}$ and $R^{18}$, taken together with the respective carbon atoms in the indenyl ring to which they are directly connected, form a ring annelated to the indenyl ring.

Optionally, in any embodiment of Formula (I) or (II) herein, $R^6$ and $R^7$, or $R^7$ and $R^{17}$, or $R^{17}$ and $R^{18}$, taken together with the respective carbon atoms in the indenyl ring to which they are directly connected, form a ring annelated to the indenyl ring comprising one or more saturated carbon atoms.

Optionally, in any embodiment of Formula (I), (II), (III) or (IV) herein, M is a group 4 metal, preferably Zr or Hf, preferably Hf.

Optionally, in any embodiment of Formula (I), (II), (III) or (IV) herein, M is a group 4 metal, preferably Zr or Hf, preferably Hf and m is 2.

Optionally, in any embodiment of Formula (II) and (IV) herein, $R^{23}$ is carbon and at least two of $R^{20}$, $R^{21}$, and $R^{22}$ are not hydrogen.

Non limiting examples of polycyclic arene ligands include:
1-methyl-1,5,6,7-tetrahydro-s-indacenyl,
1-ethyl-1,5,6,7-tetrahydro-s-indacenyl,
1-n-propyl-1,5,6,7-tetrahydro-s-indacenyl,
1-isopropyl-1,5,6,7-tetrahydro-s-indacenyl,
1-isopropyl-1,5,6,7-tetrahydro-s-indacenyl,
1-n-butyl-1,5,6,7-tetrahydro-s-indacenyl,
1-isobutyl-1,5,6,7-tetrahydro-s-indacenyl,
1-sec-butyl-1,5,6,7-tetrahydro-s-indacenyl,
1-n-pentyl-1,5,6,7-tetrahydro-s-indacenyl,
1-neopentyl-1,5,6,7-tetrahydro-s-indacenyl,
1-n-hexyl-1,5,6,7-tetrahydro-s-indacenyl,
1-n-heptyl-1,5,6,7-tetrahydro-s-indacenyl,
1-n-octyl-1,5,6,7-tetrahydro-s-indacenyl,
1-benzyl-1,5,6,7-tetrahydro-s-indacenyl,
1-phenethyl-1,5,6,7-tetrahydro-s-indacenyl, 1-(2-phenylpropyl)-1,5,6,7-tetrahydro-s-indacenyl,
1,6,6-trimethyl-1,5,6,7-tetrahydro-s-indacenyl,
1-ethyl-6,6-dimethyl-1,5,6,7-tetrahydro-s-indacenyl,
1-n-propyl-6,6-dimethyl-1,5,6,7-tetrahydro-s-indacenyl,
1-isopropyl-6,6-dimethyl-1,5,6,7-tetrahydro-s-indacenyl,
1-n-butyl-6,6-dimethyl-1,5,6,7-tetrahydro-s-indacenyl,
1-isobutyl-6,6-dimethyl-1,5,6,7-tetrahydro-s-indacenyl,
1-sec-butyl-6,6-dimethyl-1,5,6,7-tetrahydro-s-indacenyl,
1-n-pentyl-6,6-dimethyl-1,5,6,7-tetrahydro-s-indacenyl,
1-neopentyl-6,6-dimethyl-1,5,6,7-tetrahydro-s-indacenyl,
1-n-hexyl-6,6-dimethyl-1,5,6,7-tetrahydro-s-indacenyl,
1-n-heptyl-6,6-dimethyl-1,5,6,7-tetrahydro-s-indacenyl,
1-n-octyl-6,6-dimethyl-1,5,6,7-tetrahydro-s-indacenyl,
1-benzyl-6,6-dimethyl-1,5,6,7-tetrahydro-s-indacenyl,
1-phenethyl-6,6-dimethyl-1,5,6,7-tetrahydro-s-indacenyl,
1-(2-phenylpropyl)-6,6-dimethyl-1,5,6,7-tetrahydro-s-indacenyl,
1-methyl-6,6-diethyl-1,5,6,7-tetrahydro-s-indacenyl,
1,6,6-triethyl-1,5,6,7-tetrahydro-s-indacenyl,
1-n-propyl-6,6-diethyl-1,5,6,7-tetrahydro-s-indacenyl,
1-isopropyl-6,6-diethyl-1,5,6,7-tetrahydro-s-indacenyl,
1-n-butyl-6,6-diethyl-1,5,6,7-tetrahydro-s-indacenyl,
1-isobutyl-6,6-diethyl-1,5,6,7-tetrahydro-s-indacenyl,
1-n-pentyl-6,6-diethyl-1,5,6,7-tetrahydro-s-indacenyl,
1-neopentyl-6,6-diethyl-1,5,6,7-tetrahydro-s-indacenyl,
1-n-hexyl-6,6-diethyl-1,5,6,7-tetrahydro-s-indacenyl,
1-n-heptyl-6,6-diethyl-1,5,6,7-tetrahydro-s-indacenyl,
1-n-octyl-6,6-diethyl-1,5,6,7-tetrahydro-s-indacenyl,
1-benzyl-6,6-diethyl-1,5,6,7-tetrahydro-s-indacenyl,
1-phenethyl-6,6-diethyl-1,5,6,7-tetrahydro-s-indacenyl,
1-(2-phenylpropyl)-6,6-diethyl-1,5,6,7-tetrahydro-s-indacenyl,
1-methylindenyl,
1-ethylindenyl,
1-n-propylindenyl,
1-isopropylindenyl,
1-n-butylindenyl,
1-iso-butylindenyl,
1-sec-butylindenyl,
1-n-pentylindenyl,
1-neopentylindenyl,
1-n-hexylindenyl,
1-n-heptylindenyl,
1-n-octylindenyl,1-benzylindenyl,
1-phenethylindenyl,
1-(2-phenylpropyl)indenyl,
1-methyl-3,6,7,8-tetrahydro-as-indacenyl,
1-ethyl-3,6,7,8-tetrahydro-as-indacenyl,
1-n-propyl-3,6,7,8-tetrahydro-as-indacenyl,
1-isopropyl-3,6,7,8-tetrahydro-as-indacenyl,
1-n-butyl-3,6,7,8-tetrahydro-as-indacenyl,
1-isobutyl-3,6,7,8-tetrahydro-as-indacenyl,
1-n-pentyl-3,6,7,8-tetrahydro-as-indacenyl,
1-neopentyl-3,6,7,8-tetrahydro-as-indacenyl,
1-n-hexyl-3,6,7,8-tetrahydro-as-indacenyl,
1-n-heptyl-3,6,7,8-tetrahydro-as-indacenyl,
1-n-octyl-3,6,7,8-tetrahydro-as-indacenyl,
1-benzyl-3,6,7,8-tetrahydro-as-indacenyl,
1-phenethyl-3,6,7,8-tetrahydro-as-indacenyl,
1-(2-phenylpropyl)-3,6,7,8-tetrahydro-as-indacenyl,
1-methyl-benz[f]indenyl,
1-ethyl-benz[f]indenyl,
1-n-propyl-benz[f]indenyl,
1-isopropyl-benz[f]indenyl,
1-n-butyl-benz[f]indenyl,
1-isobutyl-benz[f]indenyl,
1-sec-butyl-benz[f]indenyl,
1-tert-butyl-benz[f]indenyl
1-n-pentyl-benz[f]indenyl,
1-neopentyl-benz[f]indenyl,
1-n-hexyl-benz[f]indenyl,
1-n-heptyl-benz[f]indenyl,
1-n-octyl-benz[f]indenyl,
1-benzyl-benz[f]indenyl,
1-phenethyl-benz[f]indenyl,
1-(2-phenylpropyl)-benz[f]indenyl,
1-methyl-benz[e]indenyl,
1-ethyl-benz[e]indenyl,
1-n-propyl-benz[e]indenyl,
1-isopropyl-benz[e]indenyl,
1-n-butyl-benz[e]indenyl,
1-isobutyl-benz[e]indenyl,
1-n-pentyl-benz[e]indenyl,
1-neopentyl-benz[e]indenyl,
1-n-hexyl-benz[e]indenyl,
1-n-heptyl-benz[e]indenyl,
1-n-octyl-benz[e]indenyl,
1-benzyl-benz[e]indenyl,
1-phenethyl-benz[e]indenyl,
1-(2-phenylpropyl)-benze[e]indenyl,
1-methyl-5,6,7,8-tetrahydro-1H-cyclopenta[b]naphthalenyl,
1-ethyl-5,6,7,8-tetrahydro-1H-cyclopenta[b]naphthalenyl,
1-n-propyl-5,6,7,8-tetrahydro-1H-cyclopenta[b]naphthalenyl,
1-isopropyl-5,6,7,8-tetrahydro-1H-cyclopenta[b]naphthalenyl,
1-n-butyl-5,6,7,8-tetrahydro-1H-cyclopenta[b]naphthalenyl,
1-isobutyl-5,6,7,8-tetrahydro-1H-cyclopenta[b]naphthalenyl,
1-sec-butyl-5,6,7,8-tetrahydro-1H-cyclopenta[b]naphthalenyl,
1-tert-butyl-5,6,7,8-tetrahydro-1H-cyclopenta[b]naphthalenyl,
1-n-pentyl-5,6,7,8-tetrahydro-1H-cyclopenta[b]naphthalenyl,
1-neopentyl-5,6,7,8-tetrahydro-1H-cyclopenta[b]naphthalenyl,
1-n-hexyl-5,6,7,8-tetrahydro-1H-cyclopenta[b]naphthalenyl,
1-n-heptyl-5,6,7,8-tetrahydro-1H-cyclopenta[b]naphthalenyl,
1-n-octyl-5,6,7,8-tetrahydro-1H-cyclopenta[b]naphthalenyl,
1-benzyl-5,6,7,8-tetrahydro-1H-cyclopenta[b]naphthalenyl,
1-phenethyl-5,6,7,8-tetrahydro-1H-cyclopenta[b]naphthalenyl,
1-(2-phenylpropyl)-5,6,7,8-tetrahydro-1H-cyclopenta[b]naphthalenyl, Catalyst compounds that are particularly useful in this invention include those represented by Formula (I-B), (III-B), (IV-B), (VI), (VIII), (IX), (X), (XI), (XII), (XV), (XVII), (XVIII), (XIX) or (XX):

(I-B)
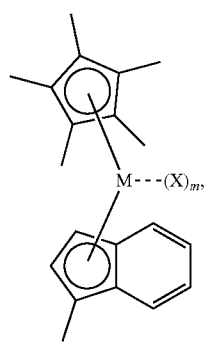
(VIII)
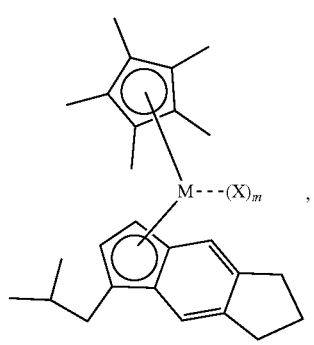
(III-B)
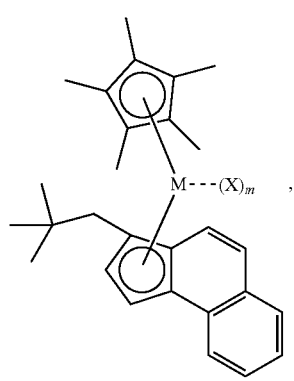
(IX)
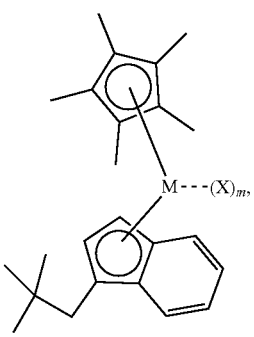
(IV-B)
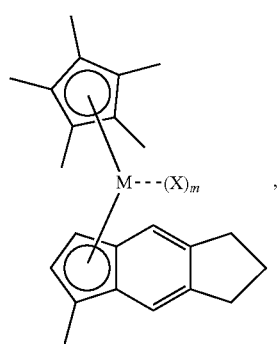
(X)
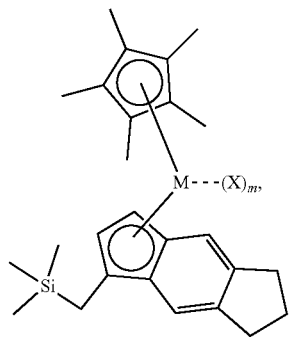
(VI)
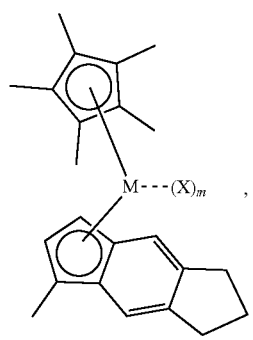
(XI)
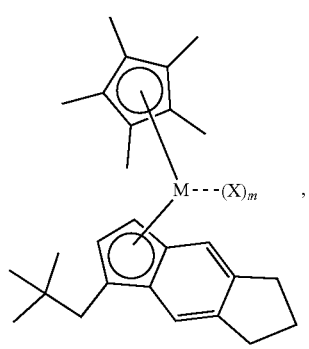

(XII)

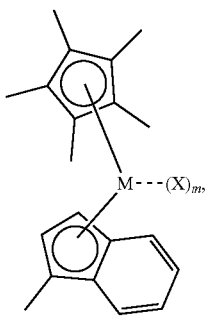

(XV)

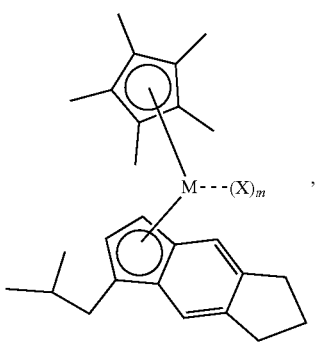

(XVII)

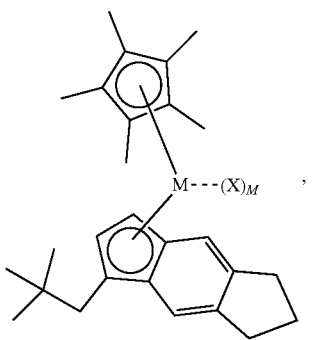

(XVIII)

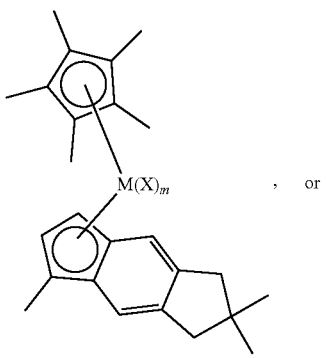, or (XIX)

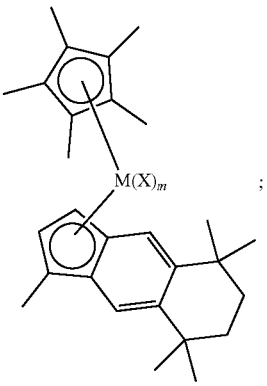;

(XX)

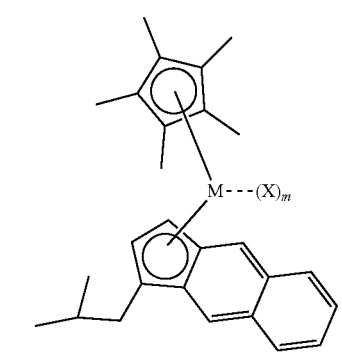.

wherein each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or two or more X moieties may together form a fused ring or ring system; M is Hf or Zr, preferably Hf; and m is 2. Optionally the metallocene is not represented by Formula (I-B).

Catalyst compounds that are useful in this invention include one or more of:
pentamethylcyclopentadienyl(1-methyl-1,5,6,7-tetrahydro-s-indacenyl)hafnium dimethyl,
pentamethylcyclopentadienyl(1-ethyl-1,5,6,7-tetrahydro-s-indacenyl)hafnium dimethyl,
pentamethylcyclopentadienyl(1-n-propyl-1,5,6,7-tetrahydro-s-indacenyl)hafnium dimethyl,
pentamethylcyclopentadienyl(1-isopropyl-1,5,6,7-tetrahydro-s-indacenyl)hafnium dimethyl,
pentamethylcyclopentadienyl(1-n-butyl-1,5,6,7-tetrahydro-s-indacenyl)hafnium dimethyl,
pentamethylcyclopentadienyl(1-isobutyl-1,5,6,7-tetrahydro-s-indacenyl)hafnium dimethyl,
pentamethylcyclopentadienyl(1-sec-butyl-1,5,6,7-tetrahydro-s-indacenyl)hafnium dimethyl,
pentamethylcyclopentadienyl(1-tert-butyl-1,5,6,7-tetrahydro-s-indacenyl)hafnium dimethyl
pentamethylcyclopentadienyl(1-pentyl-1,5,6,7-tetrahydro-s-indacenyl)hafnium dimethyl,
pentamethylcyclopentadienyl(1-neopentyl-1,5,6,7-tetrahydro-s-indacenyl)hafnium dimethyl,
pentamethylcyclopentadienyl(1-n-hexyl-1,5,6,7-tetrahydro-s-indacenyl)hafnium dimethyl,
pentamethylcyclopentadienyl(1-n-heptyl-1,5,6,7-tetrahydro-s-indacenyl)hafnium dimethyl,
pentamethylcyclopentadienyl(1-n-octyl-1,5,6,7-tetrahydro-s-indacenyl)hafnium dimethyl, pentamethylcyclopentadienyl(1-benzyl-1,5,6,7-tetrahydro-s-indacenyl)hafnium dimethyl,
pentamethylcyclopentadienyl(1-phenethyl-1,5,6,7-tetrahydro-s-indacenyl)hafnium dimethyl,
pentamethylcyclopentadienyl(1-(2-phenylpropyl)-1,5,6,7-tetrahydro-s-indacenyl)hafnium dimethyl,
pentamethylcyclopentadienyl(1,6,6-trimethyl-1,5,6,7-tetrahydro-s-indacenyl)hafnium dimethyl,
pentamethylcyclopentadienyl(1-ethyl-6,6-dimethyl-1,5,6,7-tetrahydro-s-indacenyl)hafnium dimethyl,
pentamethylcyclopentadienyl(1-n-propyl-6,6-dimethyl-1,5,6,7-tetrahydro-s-indacenyl)hafnium dimethyl,
pentamethylcyclopentadienyl(1-isopropyl-6,6-dimethyl-1,5,6,7-tetrahydro-s-indacenyl)hafnium dimethyl,
pentamethylcyclopentadienyl(1-n-butyl-6,6-dimethyl-1,5,6,7-tetrahydro-s-indacenyl)hafnium dimethyl,
pentamethylcyclopentadienyl(1-isobutyl-6,6-dimethyl-1,5,6,7-tetrahydro-s-indacenyl)hafnium dimethyl,
pentamethylcyclopentadienyl(1-sec-butyl-6,6-dimethyl-1,5,6,7-tetrahydro-s-indacenyl)hafnium dimethyl,
pentamethylcyclopentadienyl(1-tert-butyl-6,6-dimethyl-1,5,6,7-tetrahydro-s-indacenyl)hafnium dimethyl
pentamethylcyclopentadienyl(1-pentyl-6,6-dimethyl-1,5,6,7-tetrahydro-s-indacenyl)hafnium dimethyl,
pentamethylcyclopentadienyl(1-neopentyl-6,6-dimethyl-1,5,6,7-tetrahydro-s-indacenyl)hafnium dimethyl,
pentamethylcyclopentadienyl(1-n-hexyl-6,6-dimethyl-1,5,6,7-tetrahydro-s-indacenyl)hafnium dimethyl,
pentamethylcyclopentadienyl(1-n-heptyl-6,6-dimethyl-1,5,6,7-tetrahydro-s-indacenyl)hafnium dimethyl,
pentamethylcyclopentadienyl(1-n-octyl-6,6-dimethyl-1,5,6,7-tetrahydro-s-indacenyl)hafnium dimethyl,
pentamethylcyclopentadienyl(1-benzyl-6,6-dimethyl-1,5,6,7-tetrahydro-s-indacenyl)hafnium dimethyl,
pentamethylcyclopentadienyl(1-phenethyl-6,6-dimethyl-1,5,6,7-tetrahydro-s-indacenyl)hafnium dimethyl,
pentamethylcyclopentadienyl(1-(2-phenylpropyl)-6,6-dimethyl-1,5,6,7-tetrahydro-s-indacenyl)hafnium dimethyl,
pentamethylcyclopentadienyl(1-methyl-6,6-diethyl-1,5,6,7-tetrahydro-s-indacenyl)hafnium dimethyl,
pentamethylcyclopentadienyl(1,6,6-triethyl-1,5,6,7-tetrahydro-s-indacenyl)hafnium dimethyl,
pentamethylcyclopentadienyl(1-n-propyl-6,6-diethyl-1,5,6,7-tetrahydro-s-indacenyl)hafnium dimethyl,
pentamethylcyclopentadienyl(1-isopropyl-6,6-diethyl-1,5,6,7-tetrahydro-s-indacenyl)hafnium dimethyl,
pentamethylcyclopentadienyl(1-n-butyl-6,6-diethyl-1,5,6,7-tetrahydro-s-indacenyl)hafnium dimethyl,
pentamethylcyclopentadienyl(1-isobutyl-6,6-diethyl-1,5,6,7-tetrahydro-s-indacenyl)hafnium dimethyl,
pentamethylcyclopentadienyl(1-sec-butyl-6,6-diethyl-1,5,6,7-tetrahydro-s-indacenyl)hafnium dimethyl,
pentamethylcyclopentadienyl(1-tert-butyl-6,6-diethyl-1,5,6,7-tetrahydro-s-indacenyl)hafnium dimethyl
pentamethylcyclopentadienyl(1-pentyl-6,6-diethyl-1,5,6,7-tetrahydro-s-indacenyl)hafnium dimethyl,
pentamethylcyclopentadienyl(1-neopentyl-6,6-diethyl-1,5,6,7-tetrahydro-s-indacenyl)hafnium dimethyl,
pentamethylcyclopentadienyl(1-benzyl-6,6-diethyl-1,5,6,7-tetrahydro-s-indacenyl)hafnium dimethyl,
pentamethylcyclopentadienyl(1-phenethyl-6,6-diethyl-1,5,6,7-tetrahydro-s-indacenyl)hafnium dimethyl,
pentamethylcyclopentadienyl(1-(2-phenylpropyl)-6,6-diethyl-1,5,6,7-tetrahydro-s-indacenyl)hafnium dimethyl,
pentamethylcyclopentadienyl(1-methylindenyl)hafnium dimethyl,
pentamethylcyclopentadienyl(1-ethylindenyl)hafnium dimethyl,
pentamethylcyclopentadienyl(1-n-propylindenyl)hafnium dimethyl,
pentamethylcyclopentadienyl(1-isopropylindenyl)hafnium dimethyl,
pentamethylcyclopentadienyl(1-n-butylindenyl)hafnium dimethyl,
pentamethylcyclopentadienyl(1-isobutylindenyl)hafnium dimethyl,
pentamethylcyclopentadienyl(1-sec-butylindenyl)hafnium dimethyl,
pentamethylcyclopentadienyl(1-tert-butylindenyl)hafnium dimethyl
pentamethylcyclopentadienyl(1-pentylindenyl)hafnium dimethyl,
pentamethylcyclopentadienyl(1-neopentylindenyl)hafnium dimethyl,
pentamethylcyclopentadienyl(1-n-hexylindenyl)hafnium dimethyl,
pentamethylcyclopentadienyl(1-n-heptylindenyl)hafnium dimethyl,
pentamethylcyclopentadienyl(1-n-octylindenyl)hafnium dimethyl,
pentamethylcyclopentadienyl(1-benzylindenyl)hafnium dimethyl,
pentamethylcyclopentadienyl(1-phenethylindenyl)hafnium dimethyl,
pentamethylcyclopentadienyl(1-(2-phenylpropyl)indenyl)hafnium dimethyl,
pentamethylcyclopentadienyl(1-methyl-3,6,7,8-tetrahydro-as-indacenyl)hafnium dimethyl,
pentamethylcyclopentadienyl(1-ethyl-3,6,7,8-tetrahydro-as-indacenyl)hafnium dimethyl,
pentamethylcyclopentadienyl(1-n-propyl-3,6,7,8-tetrahydro-as-indacenyl)hafnium dimethyl,
pentamethylcyclopentadienyl(1-isopropyl-3,6,7,8-tetrahydro-as-indacenyl)hafnium dimethyl,
pentamethylcyclopentadienyl(1-n-butyl-3,6,7,8-tetrahydro-as-indacenyl)hafnium dimethyl,
pentamethylcyclopentadienyl(1-isobutyl-3,6,7,8-tetrahydro-as-indacenyl)hafnium dimethyl,
pentamethylcyclopentadienyl(1-sec-butyl-3,6,7,8-tetrahydro-as-indacenyl)hafnium dimethyl,
pentamethylcyclopentadienyl(1-tert-butyl-3,6,7,8-tetrahydro-as-indacenyl)hafnium dimethyl
pentamethylcyclopentadienyl(1-pentyl-3,6,7,8-tetrahydro-as-indacenyl)hafnium dimethyl,
pentamethylcyclopentadienyl(1-neopentyl-3,6,7,8-tetrahydro-as-indacenyl)hafnium dimethyl,
pentamethylcyclopentadienyl(1-benzyl-3,6,7,8-tetrahydro-as-indacenyl)hafnium dimethyl,
pentamethylcyclopentadienyl(1-phenethyl-3,6,7,8-tetrahydro-as-indacenyl)hafnium dimethyl,
pentamethylcyclopentadienyl(1-(2-phenylpropyl)-3,6,7,8-tetrahydro-as-indacenyl)hafnium dimethyl,
pentamethylcyclopentadienyl(1-methyl-benz[f]indenyl)hafnium dimethyl,
pentamethylcyclopentadienyl(1-ethyl-benz[f]indenyl)hafnium dimethyl,
pentamethylcyclopentadienyl(1-n-propyl-benz[f]indenyl)hafnium dimethyl,
pentamethylcyclopentadienyl(1-isopropyl-benz[f]indenyl)hafnium dimethyl,
pentamethylcyclopentadienyl(1-n-butyl-benz[f]indenyl)hafnium dimethyl, pentamethylcyclopentadienyl(1-isobutyl-benz[f]indenyl) hafnium dimethyl,
pentamethylcyclopentadienyl(1-sec-butyl-benz[f]indenyl) hafnium dimethyl,
pentamethylcyclopentadienyl(1-tert-butyl-benz[f]indenyl) hafnium dimethyl
pentamethylcyclopentadienyl(1-pentyl-benz[f]indenyl)hafnium dimethyl,
pentamethylcyclopentadienyl(1-neopentyl-benz[f]indenyl) hafnium dimethyl,
pentamethylcyclopentadienyl(1-benzyl-benz[f]indenyl)hafnium dimethyl,
pentamethylcyclopentadienyl(1-phenethyl-benz[f]indenyl) hafnium dimethyl,
pentamethylcyclopentadienyl(1-(2-phenylpropyl)-benz[f] indenyl)hafnium dimethyl,
pentamethylcyclopentadienyl(1-methyl-benz[e]indenyl)hafnium dimethyl,
pentamethylcyclopentadienyl(1-ethyl-benz[e]indenyl)hafnium dimethyl,
pentamethylcyclopentadienyl(1-n-propyl-benz[e]indenyl) hafnium dimethyl,
pentamethylcyclopentadienyl(1-isopropyl-benz[e]indenyl) hafnium dimethyl,
pentamethylcyclopentadienyl(1-n-butyl-benz[e]indenyl) hafnium dimethyl,
pentamethylcyclopentadienyl(1-isobutyl-benz[e]indenyl) hafnium dimethyl,
pentamethylcyclopentadienyl(1-sec-butyl-benz[e]indenyl) hafnium dimethyl,
pentamethylcyclopentadienyl(1-tert-butyl-benz[e]indenyl) hafnium dimethyl
pentamethylcyclopentadienyl(1-pentyl-benz[e]indenyl)hafnium dimethyl,
pentamethylcyclopentadienyl(1-neopentyl-benz[e]indenyl) hafnium dimethyl,
pentamethylcyclopentadienyl(1-benzyl-benz[e]indenyl)hafnium dimethyl,
pentamethylcyclopentadienyl(1-phenethyl-benz[e]indenyl) hafnium dimethyl,
pentamethylcyclopentadienyl(1-(2-phenylpropyl)-benzef] indenyl)hafnium dimethyl,
pentamethylcyclopentadienyl(1-methyl-5,6,7,8-tetrahydro-1H-cyclopenta[b]naphthalene)hafnium dimethyl,
pentamethylcyclopentadienyl(1-ethyl-5,6,7,8-tetrahydro-1H-cyclopenta[b]naphthalene)hafnium dimethyl,
pentamethylcyclopentadienyl(1-n-propyl-5,6,7,8-tetrahydro-1H-cyclopenta[b]naphthalene)hafnium dimethyl,
pentamethylcyclopentadienyl(1-isopropyl-5,6,7,8-tetrahydro-1H-cyclopenta[b]naphthalene)hafnium dimethyl,
pentamethylcyclopentadienyl(1-n-butyl-5,6,7,8-tetrahydro-1H-cyclopenta[b]naphthalene)hafnium dimethyl,
pentamethylcyclopentadienyl(1-isobutyl-5,6,7,8-tetrahydro-1H-cyclopenta[b]naphthalene)hafnium dimethyl,
pentamethylcyclopentadienyl(1-sec-butyl-5,6,7,8-tetrahydro-1H-cyclopenta[b]naphthalene)hafnium dimethyl,
pentamethylcyclopentadienyl(1-tert-butyl-5,6,7,8-tetrahydro-1H-cyclopenta[b]naphthalene)hafnium dimethyl
pentamethylcyclopentadienyl(1-pentyl-5,6,7,8-tetrahydro-1H-cyclopenta[b]naphthalene)hafnium dimethyl,
pentamethylcyclopentadienyl(1-neopentyl-5,6,7,8-tetrahydro-1H-cyclopenta[b]naphthalene)hafnium dimethyl,
pentamethylcyclopentadienyl(1-benzyl-5,6,7,8-tetrahydro-1H-cyclopenta[b]naphthalene)hafnium dimethyl,
pentamethylcyclopentadienyl(1-phenethyl-5,6,7,8-tetrahydro-1H-cyclopenta[b]naphthalene)hafnium dimethyl,
pentamethylcyclopentadienyl(1-(2-phenylpropyl)-5,6,7,8-tetrahydro-1H-cyclopenta[b]naphthalene)hafnium dimethyl,
pentamethylcyclopentadienyl(1-methyl-6,7,8,9-tetrahydro-1H-cyclopenta[a]naphthalene)hafnium dimethyl,
pentamethylcyclopentadienyl(1-ethyl-6,7,8,9-tetrahydro-1H-cyclopenta[a]naphthalene)hafnium dimethyl,
pentamethylcyclopentadienyl(1-n-propyl-6,7,8,9-tetrahydro-1H-cyclopenta[a]naphthalene)hafnium dimethyl,
pentamethylcyclopentadienyl(1-isopropyl-6,7,8,9-tetrahydro-1H-cyclopenta[a]naphthalene)hafnium dimethyl,
pentamethylcyclopentadienyl(1-n-butyl-6,7,8,9-tetrahydro-1H-cyclopenta[a]naphthalene)hafnium dimethyl,
pentamethylcyclopentadienyl(1-isobutyl-6,7,8,9-tetrahydro-1H-cyclopenta[a]naphthalene)hafnium dimethyl,
pentamethylcyclopentadienyl(1-sec-butyl-6,7,8,9-tetrahydro-1H-cyclopenta[a]naphthalene)hafnium dimethyl,
pentamethylcyclopentadienyl(1-tert-butyl-6,7,8,9-tetrahydro-1H-cyclopenta[a]naphthalene)hafnium dimethyl
pentamethylcyclopentadienyl(1-pentyl-6,7,8,9-tetrahydro-1H-cyclopenta[a]naphthalene)hafnium dimethyl,
pentamethylcyclopentadienyl(1-neopentyl-6,7,8,9-tetrahydro-1H-cyclopenta[a]naphthalene)hafnium dimethyl,
pentamethylcyclopentadienyl(1-benzyl-6,7,8,9-tetrahydro-1H-cyclopenta[a]naphthalene)hafnium dimethyl,
pentamethylcyclopentadienyl(1-phenethyl-6,7,8,9-tetrahydro-1H-cyclopenta[a]naphthalene)hafnium dimethyl,
pentamethylcyclopentadienyl(1-(2-phenylpropyl)-6,7,8,9-tetrahydro-1H-cyclopenta[a]naphthalene)hafnium dimethyl,
pentamethylcyclopentadienyl(1,5,6-trimethylindenyl)hafnium dimethyl,
pentamethylcyclopentadienyl(1-ethyl-5,6-dimethylindenyl) hafnium dimethyl,
pentamethylcyclopentadienyl(1-n-propyl-5,6-dimethylindenyl)hafnium dimethyl,
pentamethylcyclopentadienyl(1-isopropyl-5,6-dimethylindenyl)hafnium dimethyl,
pentamethylcyclopentadienyl(1-n-buty-5,6-dimethyllindenyl)hafnium dimethyl,
pentamethylcyclopentadienyl(1-isobuty-5,6-dimethyllindenyl)hafnium dimethyl,
pentamethylcyclopentadienyl(1-sec-butyl-5,6-dimethylindenyl)hafnium dimethyl,
pentamethylcyclopentadienyl(1-tert-butyl-5,6-dimethylindenyl)hafnium dimethyl
pentamethylcyclopentadienyl(1-pentyl-5,6-dimethylindenyl)hafnium dimethyl,
pentamethylcyclopentadienyl(1-neopentyl-5,6-dimethylindenyl)hafnium dimethyl,
pentamethylcyclopentadienyl(1-benzyl-5,6-dimethylindenyl)hafnium dimethyl,
pentamethylcyclopentadienyl(1-phenethyl-5,6-dimethylindenyl)hafnium dimethyl,
pentamethylcyclopentadienyl(1-(2-phenylpropyl)-5,6-dimethylindenyl)hafnium dimethyl,
pentamethylcyclopentadienyl(1-methyl-1,5,6,7-tetrahydro-s-indacenyl)zirconium dimethyl,
pentamethylcyclopentadienyl(1-isobutyl-1,5,6,7-tetrahydro-s-indacenyl)zirconium dimethyl,
pentamethylcyclopentadienyl(1,6,6-trimethyl-1,5,6,7-tetrahydro-s-indacenyl)zirconium dimethyl,
tetramethylcyclopentadienyl(1-methyl-1,5,6,7-tetrahydro-s-indacenyl)hafnium dimethyl,
tetramethylcyclopentadienyl(1-isobutyl-1,5,6,7-tetrahydro-s-indacenyl)hafnium dimethyl, tetramethylcyclopentadienyl(1,6,6-trimethyl-1,5,6,7-tetrahydro-s-indacenyl)hafnium dimethyl, pentamethylcyclopentadienyl(1-methyl-1,5,6,7-tetrahydro-s-indacenyl)hafnium dibenzyl, pentamethylcyclopentadienyl(1-isobutyl-1,5,6,7-tetrahydro-s-indacenyl)hafnium dibenzyl, and pentamethylcyclopentadienyl(1,6,6-trimethyl-1,5,6,7-tetrahydro-s-indacenyl)hafnium dibenzyl.

Catalyst compounds that are particularly useful in this invention include one or more of:

pentamethylcyclopentadienyl(1-methyl-1,5,6,7-tetrahydro-s-indacenyl)hafnium dimethyl, pentamethylcyclopentadienyl(1-ethyl-1,5,6,7-tetrahydro-s-indacenyl)hafnium dimethyl, pentamethylcyclopentadienyl(1-n-propyl-1,5,6,7-tetrahydro-s-indacenyl)hafnium dimethyl, pentamethylcyclopentadienyl(1-isopropyl-1,5,6,7-tetrahydro-s-indacenyl)hafnium dimethyl, pentamethylcyclopentadienyl(1-n-butyl-1,5,6,7-tetrahydro-s-indacenyl)hafnium dimethyl, pentamethylcyclopentadienyl(1-isobutyl-1,5,6,7-tetrahydro-s-indacenyl)hafnium dimethyl, pentamethylcyclopentadienyl(1,6,6-trimethyl-1,5,6,7-tetrahydro-s-indacenyl)hafnium dimethyl, pentamethylcyclopentadienyl(1-isobutyl-6,6-dimethyl-1,5,6,7-tetrahydro-s-indacenyl)hafnium dimethyl, pentamethylcyclopentadienyl(1-methyl-6,6-diethyl-1,5,6,7-tetrahydro-s-indacenyl)hafnium dimethyl, pentamethylcyclopentadienyl(1,6,6-triethyl-1,5,6,7-tetrahydro-s-indacenyl)hafnium dimethyl, pentamethylcyclopentadienyl(1-isobutyl-6,6-diethyl-1,5,6,7-tetrahydro-s-indacenyl)hafnium dimethyl, pentamethylcyclopentadienyl(1-methylindenyl)hafnium dimethyl, pentamethylcyclopentadienyl(1-isobutylindenyl)hafnium dimethyl, pentamethylcyclopentadienyl(1-methyl-3,6,7,8-tetrahydro-as-indacenyl)hafnium dimethyl, pentamethylcyclopentadienyl(1-isobutyl-3,6,7,8-tetrahydro-as-indacenyl)hafnium dimethyl, pentamethylcyclopentadienyl(1-methyl-5,6,7,8-tetrahydro-1H-cyclopenta[b]naphthalene)hafnium dimethyl, pentamethylcyclopentadienyl(1-isobutyl-5,6,7,8-tetrahydro-1H-cyclopenta[b]naphthalene)hafnium dimethyl, pentamethylcyclopentadienyl(1-methyl-6,7,8,9-tetrahydro-1H-cyclopenta[la]naphthalene)hafnium dimethyl, pentamethylcyclopentadienyl(1-isobutyl-6,7,8,9-tetrahydro-1H-cyclopenta[la]naphthalene)hafnium dimethyl, pentamethylcyclopentadienyl(1,5,6-trimethylindenyl)hafnium dimethyl, and pentamethylcyclopentadienyl(1-isobuty-5,6-dimethylindenyl)hafnium dimethyl.

Particularly desirable metallocene compounds useful for the process of the present invention include the following compounds and their optical isomers, if applicable (not shown):

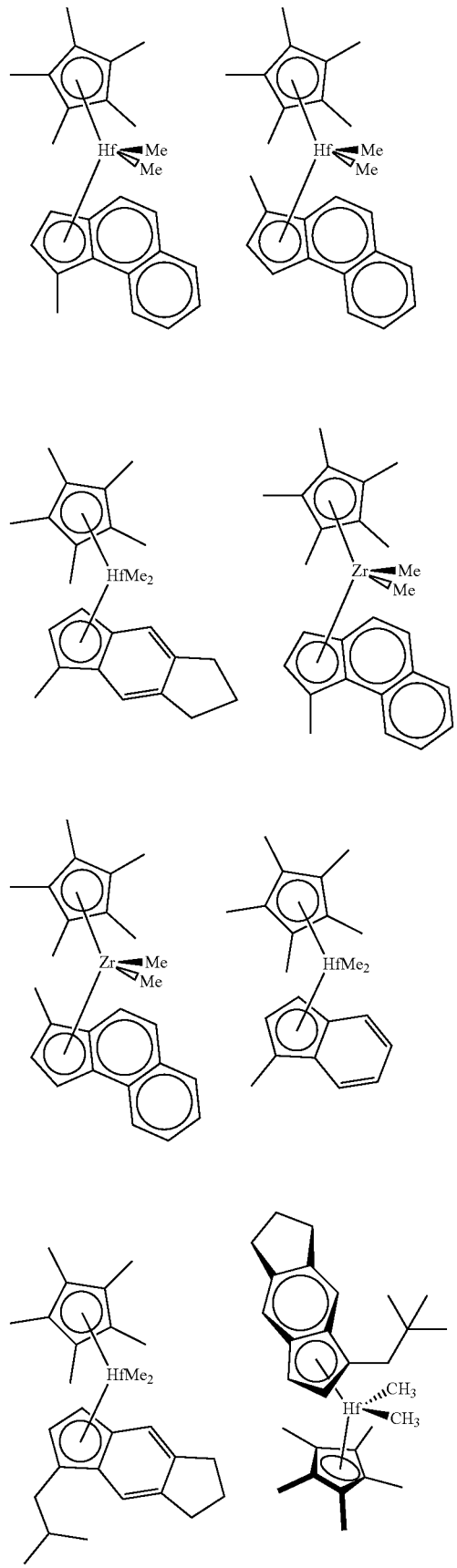

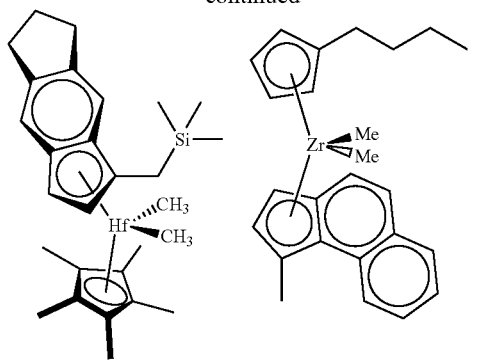
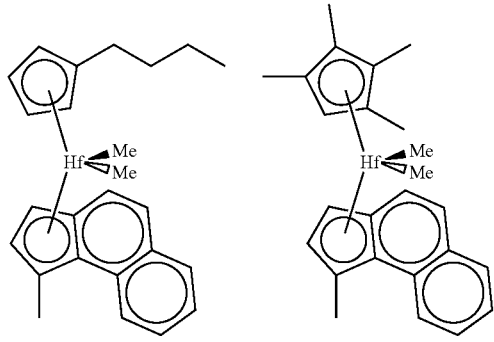
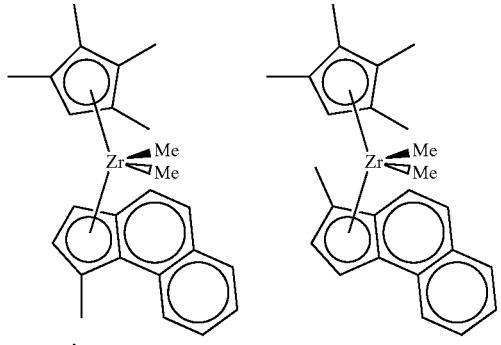
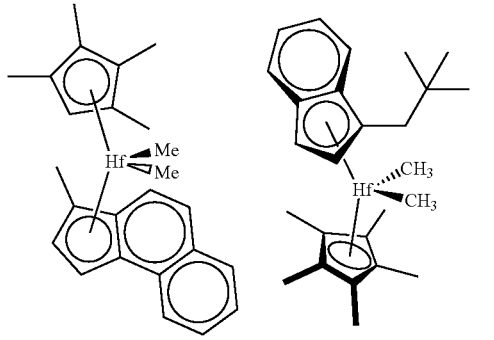
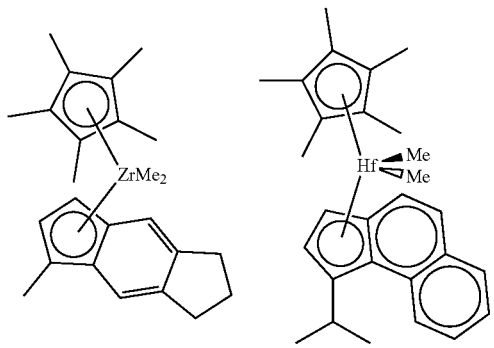
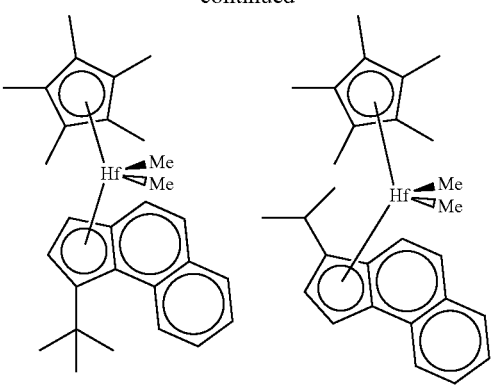
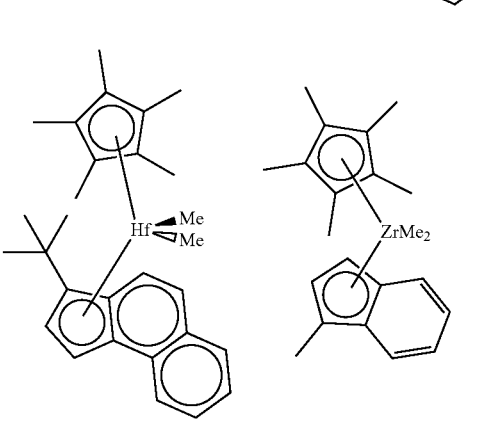
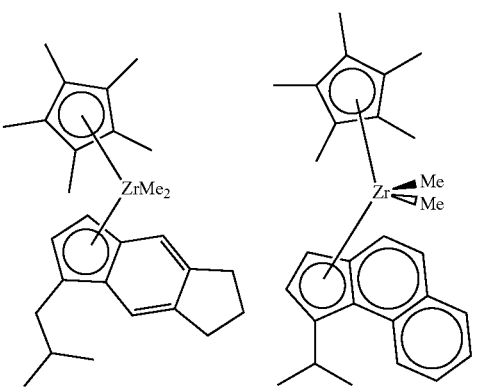
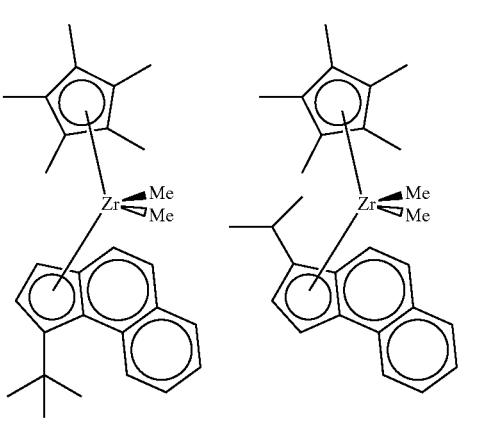

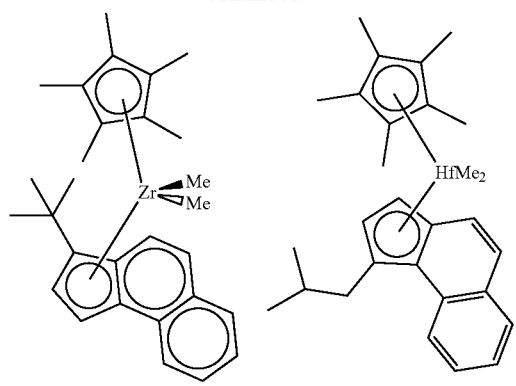
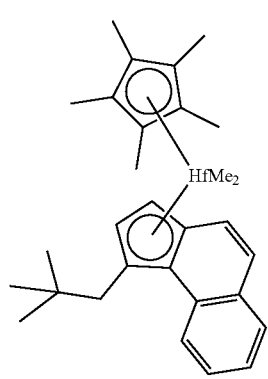
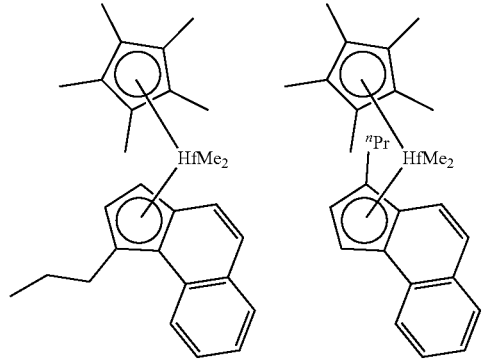
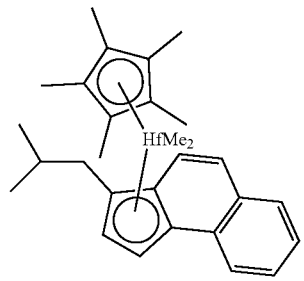
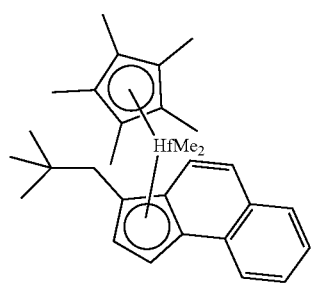

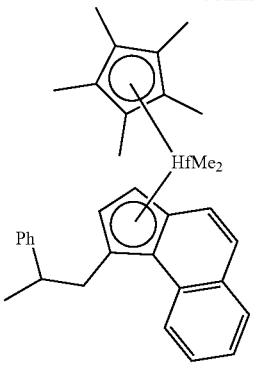
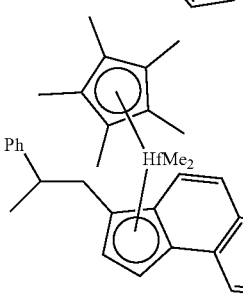
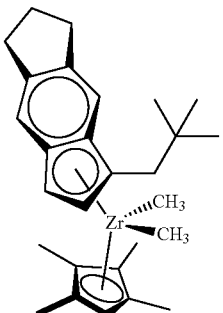
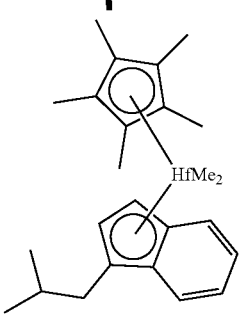

Metallocene compounds generally can be synthesized by using typical chemical reagents (e.g., halides of hafnium, zirconium, titanium) and intermediates (such as ligands containing one or two substituted or unsubstituted Cp rings, substituted or unsubstituted annelated Cp ring such as indenyl rings or benzindenyl rings, and the like) that are commercially available, and following typical reaction schemes exemplified in various synthesis descriptions, see for example U.S. Ser. No. 16/394,197, filed Apr. 25, 2019, and U.S. Ser. No. 16/394,166, filed Apr. 25, 2019, which describe catalyst compounds useful herein and are incorporated by reference herein. See also U.S. Ser. No. 16/270,085, filed Feb. 7, 2019 which claims priority to and the benefit of U.S. Ser. No. 62/629,200, filed Feb. 12, 2018, and U.S. Ser.

No. 62/732,311, filed Sep. 17, 2018, which describe catalyst compounds useful herein and are incorporated by reference herein.

III.2 Activators and Activation of the Metallocene Compound

Non-Coordinating Anion (NCA) Activators

Noncoordinating anion (NCA) means an anion either that does not coordinate to the catalyst metal cation or that does coordinate to the metal cation, but only weakly. The term NCA is also defined to include multicomponent NCA-containing activators, such as N,N-dioctadecylanilinium tetrakis(perfluoronaphthyl)borate, that contain an acidic cationic group and the non-coordinating anion. The term NCA is also defined to include neutral Lewis acids, such as tris(pentafluoronaphthyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the non-coordinating anion. Suitable metals can include aluminum, gold, and platinum. Suitable metalloids can include boron, aluminum, phosphorus, and silicon. The term non-coordinating anion activator includes neutral activators, ionic activators, and Lewis acid activators.

"Compatible" non-coordinating anions can be those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with the present disclosure are those that are compatible, stabilize the transition metal cation in the sense of balancing its ionic charge at +1, and yet retain sufficient lability to permit displacement during polymerization.

The activators of the present invention comprise non-coordinating anions.

Activators

Advantageously, the activators of the present disclosure are soluble in non-aromatic-hydrocarbon solvents, such as aliphatic solvents.

In one or more embodiments, a 20 wt % mixture of the activator compound in n-hexane, isohexane, cyclohexane, methylcyclohexane, or a combination thereof, forms a clear homogeneous solution at 25° C., preferably a 30 wt % mixture of the activator compound in n-hexane, isohexane, cyclohexane, methylcyclohexane, or a combination thereof, forms a clear homogeneous solution at 25° C.

In embodiments of the invention, the activators described herein have a solubility of more than 10 mM (or more than 20 mM, or more than 50 mM) at 25° C. (stirred 2 hours) in methylcyclohexane.

In embodiments of the invention, the activators described herein have a solubility of more than 1 mM (or more than 10 mM, or more than 20 mM) at 25° C. (stirred 2 hours) in isohexane.

In embodiments of the invention, the activators described herein have a solubility of more than 10 mM (or more than 20 mM, or more than 50 mM) at 25° C. (stirred 2 hours) in methylcyclohexane and a solubility of more than 1 mM (or more than 10 mM, or more than 20 mM) at 25° C. (stirred 2 hours) in isohexane.

The present disclosure relates to a catalyst system comprising a metallocene transition metal compound and an activator compound as described herein, to the use of such activator compounds for activating a transition metal compound in a catalyst system for polymerizing olefins, and to processes for polymerizing olefins, the process comprising contacting under polymerization conditions one or more olefins with a catalyst system comprising a metallocene transition metal compound and such activator compounds, where aromatic solvents, such as toluene, are absent (e.g. present at zero mol %, alternately present at less than 1 mol %, preferably the catalyst system, the polymerization reaction and/or the polymer produced are free of "detectable aromatic hydrocarbon solvent," such as toluene. For purposes of the present disclosure, "detectable aromatic hydrocarbon solvent" means 0.1 mg/m$^2$ or more as determined by gas phase chromatography. For purposes of the present disclosure, "detectable toluene" means 0.1 mg/m$^2$ or more as determined by gas phase chromatography.

The polyalpha-olefins produced herein preferably contain 0 ppm (alternately less than 1 ppm) of aromatic hydrocarbon. Preferably, the polyalpha-olefins produced herein contain 0 ppm (alternately less than 1 ppm) of toluene.

The catalyst systems used herein preferably contain 0 ppm (alternately less than 1 ppm) of aromatic hydrocarbon. Preferably, the catalyst systems used herein contain 0 ppm (alternately less than 1 ppm) of toluene.

Non-aromatic-hydrocarbon soluble activator compounds useful herein include those represented by the Formula (V):

$$[R^{1'}R^{2'}R^{3'}EH]_{d+}[Mt^{k+}Q_n]^{d-} \quad (V)$$

wherein:
E is nitrogen or phosphorous;
d is 1, 2 or 3; k is 1, 2, or 3; n is 1, 2, 3, 4, 5, or 6; n−k=d (preferably d is 1, 2 or 3; k is 3; n is 4, 5, or 6);
$R^{1'}$, $R^{2'}$, and $R^{3'}$ are independently $C_1$ to $C_{50}$ hydrocarbyl group optionally substituted with one or more alkoxy groups, silyl groups, a halogen atoms, or halogen containing groups,
wherein $R^{1'}$, $R^{2'}$, and $R^{3'}$ together comprise 15 or more carbon atoms;
Mt is an element selected from group 13 of the Periodic Table of the Elements, such as B or P; and
each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Non-aromatic-hydrocarbon soluble activator compounds useful herein include those represented by the Formula (VI):

$$[R^{1'}R^{2'}R^{3'}EH]^{+}[BR^{4'}R^{5'}R^{6'}R^{7'}]^{-} \quad (VI)$$

wherein:
E is nitrogen or phosphorous;
$R^{1'}$ is a methyl group;
$R^{2'}$ and $R^{3'}$ are independently is $C_4$-$C_{50}$ hydrocarbyl group optionally substituted with one or more alkoxy groups, silyl groups, a halogen atoms, or halogen containing groups wherein $R^{2'}$ and $R^{3'}$ together comprise 14 or more carbon atoms;
B is boron;
and $R^{4'}$, $R^{5'}$, $R^{6'}$, and $R^{7'}$ are independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Non-aromatic-hydrocarbon soluble activator compounds useful herein include those represented by the Formula (VII) or Formula (VIII):

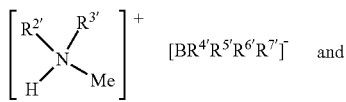 (VII)

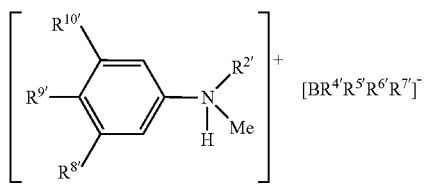 (VIII)

wherein:

N is nitrogen;

$R^{2'}$ and $R^{3'}$ are independently is $C_6$-$C_{40}$ hydrocarbyl group optionally substituted with one or more alkoxy groups, silyl groups, a halogen atoms, or halogen containing groups wherein $R^{2'}$ and $R^{3'}$ (if present) together comprise 14 or more carbon atoms;

$R^{8'}$, $R^{9'}$, and $R^{10'}$ are independently a $C_4$-$C_{30}$ hydrocarbyl or substituted $C_4$-$C_{30}$ hydrocarbyl group;

B is boron;

and $R^{4'}$, $R^{5'}$, $R^{6'}$, and $R^{7'}$ are independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

Optionally, in any of Formulas (V), (VI), (VII), or (VIII) herein, $R^{4'}$, $R^{5'}$, $R^{6'}$, and $R^{7'}$ are pentafluorophenyl.

Optionally, in any of Formulas (V), (VI), (VII), or (VIII) herein, $R^{4'}$, $R^{5'}$, $R^{6'}$, and $R^{7'}$ are pentafluoronaphthyl.

Optionally, in any embodiment of Formula (VIII) herein, $R^{8'}$ and $R^{10'}$ are hydrogen atoms and $R^{9'}$ is a $C_4$-$C_{30}$ hydrocarbyl group which is optionally substituted with one or more alkoxy groups, silyl groups, a halogen atoms, or halogen containing groups.

Optionally, in any embodiment of Formula (VIII) herein, $R^{9'}$ is a $C_8$-$C_{22}$ hydrocarbyl group which is optionally substituted with one or more alkoxy groups, silyl groups, a halogen atoms, or halogen containing groups.

Optionally, in any embodiment of Formula (VII) or (VIII) herein, $R^{2'}$ and $R^{3'}$ are independently a $C_{12}$-$C_{22}$ hydrocarbyl group.

Optionally, $R^{1'}$, $R^{2'}$ and $R^{3'}$ together comprise 15 or more carbon atoms (such as 18 or more carbon atoms, such as 20 or more carbon atoms, such as 22 or more carbon atoms, such as 25 or more carbon atoms, such as 30 or more carbon atoms, such as 35 or more carbon atoms, such as 38 or more carbon atoms, such as 40 or more carbon atoms, such as 15 to 100 carbon atoms, such as 25 to 75 carbon atoms).

Optionally, $R^{2'}$ and $R^{3'}$ together comprise 15 or more carbon atoms (such as 18 or more carbon atoms, such as 20 or more carbon atoms, such as 22 or more carbon atoms, such as 25 or more carbon atoms, such as 30 or more carbon atoms, such as 35 or more carbon atoms, such as 38 or more carbon atoms, such as 40 or more carbon atoms, such as 15 to 100 carbon atoms, such as 25 to 75 carbon atoms).

Optionally, $R^{8'}$, $R^{9'}$, and $R^{10'}$ together comprise 15 or more carbon atoms (such as 18 or more carbon atoms, such as 20 or more carbon atoms, such as 22 or more carbon atoms, such as 25 or more carbon atoms, such as 30 or more carbon atoms, such as 35 or more carbon atoms, such as 38 or more carbon atoms, such as 40 or more carbon atoms, such as 15 to 100 carbon atoms, such as 25 to 75 carbon atoms).

Optionally, when Q is a fluorophenyl group, then $R^{2'}$ is not a $C_1$-$C_{40}$ linear alkyl group (alternately $R^{2'}$ is not an optionally substituted $C_1$-$C_{40}$ linear alkyl group).

Optionally, each of $R^{4'}$, $R^{5'}$, $R^{6'}$, and $R^{7'}$ is an aryl group (such as phenyl or naphthyl), wherein at least one of $R^{4'}$, $R^{5'}$, $R^{6'}$, and $R^{7'}$ is substituted with at least one fluorine atom, preferably each of $R^{4'}$, $R^{5'}$, $R^{6'}$, and $R^{7'}$ is a perfluoroaryl group (such as perfluorophenyl or perfluoronaphthyl).

Optionally, each Q is an aryl group (such as phenyl or naphthyl), wherein at least one Q is substituted with at least one fluorine atom, preferably each Q is a perfluoroaryl group (such as perfluorophenyl or perfluoronaphthyl).

Optionally, $R^{1'}$ is a methyl group; $R^{2'}$ is $C_6$-$C_{50}$ aryl group; and $R^{3'}$ is independently $C_1$-$C_{40}$ linear alkyl or $C_5$-$C_{50}$-aryl group.

Optionally, each of $R^{2'}$ and $R^{3'}$ is independently unsubstituted or substituted with at least one of halide, $C_1$-$C_{35}$ alkyl, $C_5$-$C_{15}$ aryl, $C_6$-$C_{35}$ arylalkyl, $C_6$-$C_{35}$ alkylaryl, wherein $R^2$, and $R^3$ together comprise 20 or more carbon atoms.

Optionally, each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical, provided that when Q is a fluorophenyl group, then $R^{2'}$ is not a $C_1$-$C_{40}$ linear alkyl group, preferably $R^{2'}$ is not an optionally substituted $C_1$-$C_{40}$ linear alkyl group (alternately when Q is a substituted phenyl group, then $R^{2'}$ is not a $C_1$-$C_{40}$ linear alkyl group, preferably $R^{2'}$ is not an optionally substituted $C_1$-$C_{40}$ linear alkyl group). Optionally, when Q is a fluorophenyl group (alternately when Q is a substituted phenyl group), then $R^{2'}$ is a meta- and/or para-substituted phenyl group, where the meta and para substituents are, independently, an optionally substituted $C_1$ to $C_{40}$ hydrocarbyl group (such as a $C_6$ to $C_{40}$ aryl group or linear alkyl group, a $C_{12}$ to $C_{30}$ aryl group or linear alkyl group, or a $C_{10}$ to $C_{20}$ aryl group or linear alkyl group), an optionally substituted alkoxy group, or an optionally substituted silyl group. Optionally, each Q is a fluorinated hydrocarbyl group having 1 to 30 carbon atoms, more preferably each Q is a fluorinated aryl (such as phenyl or naphthyl) group, and most preferably each Q is a perflourinated aryl (such as phenyl or naphthyl) group. Examples of suitable $[Mt^{k+}Q_n]^{d-}$ also include diboron compounds as disclosed in U.S. Pat. No. 5,447,895, which is fully incorporated herein by reference. Optionally, at least one Q is not substituted phenyl. Optionally all Q are not substituted phenyl. Optionally at least one Q is not perfluorophenyl. Optionally all Q are not perfluorophenyl.

In some embodiments of the invention, $R^{1'}$ is not methyl, $R^{2'}$ is not $C_{18}$ alkyl and $R^{3'}$ is not $C_{18}$ alkyl, alternately $R^{1'}$ is not methyl, $R^{2'}$ is not $C_{18}$ alkyl and $R^{3'}$ is not $C_{18}$ alkyl and at least one Q is not substituted phenyl, optionally all Q are not substituted phenyl.

Useful cation components in Formulas (V) to (VIII) include those represented by the formula:

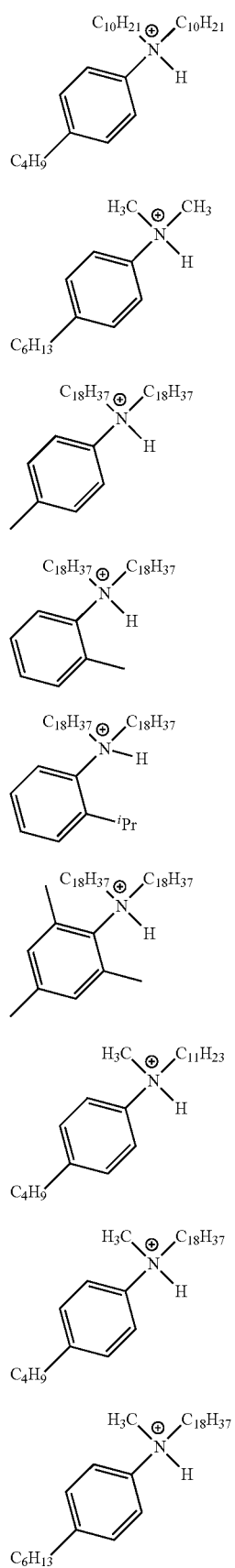
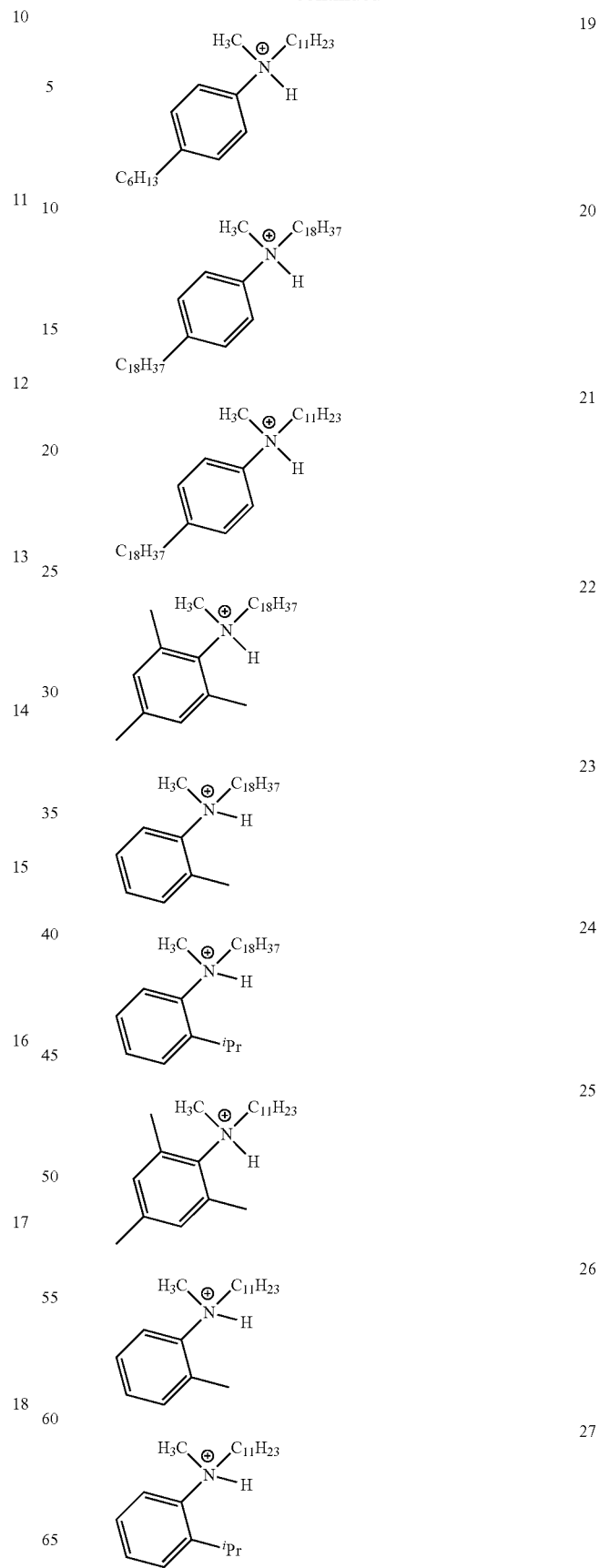

-continued

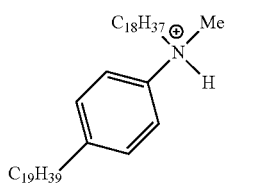

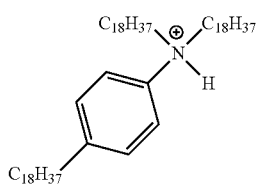

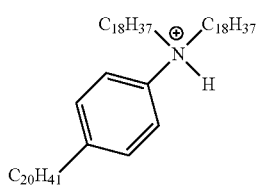

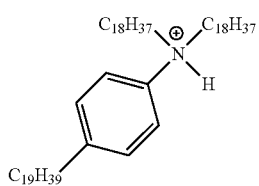

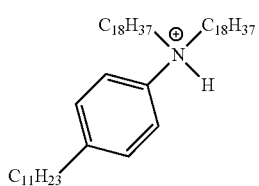

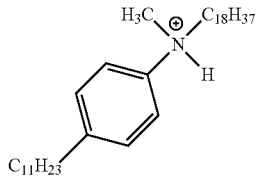

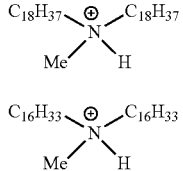

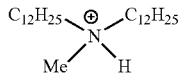

Useful cation components in Formulas (V) to (VIII) include those represented by the formula:

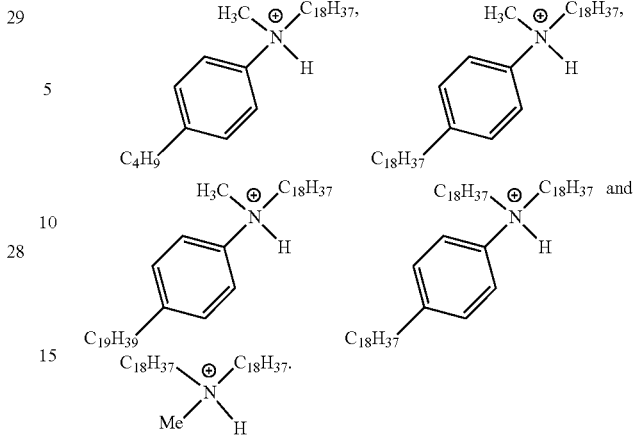

The anion component of the activators described herein includes those represented by the formula $[Mt^{k+}Q_n]^-$ wherein k is 1, 2, or 3; n is 1, 2, 3, 4, 5, or 6 (preferably 1, 2, 3, or 4), (preferably k is 3; n is 4, 5, or 6, preferably when M is B, n is 4); Mt is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group, optionally having 1 to 20 carbon atoms, more preferably each Q is a fluorinated aryl group, and most preferably each Q is a perfluorinated aryl group. Preferably at least one Q is not substituted phenyl, such as perfluorophenyl, preferably all Q are not substituted phenyl, such as perfluorophenyl.

In one embodiment, the borate activator comprises tetrakis(heptafluoronaphth-2-yl)borate.

In one embodiment, the borate activator comprises tetrakis(pentafluorophenyl)borate.

Preferred anions for use in the non-coordinating anion activators described herein include those represented by Formula 7 below:

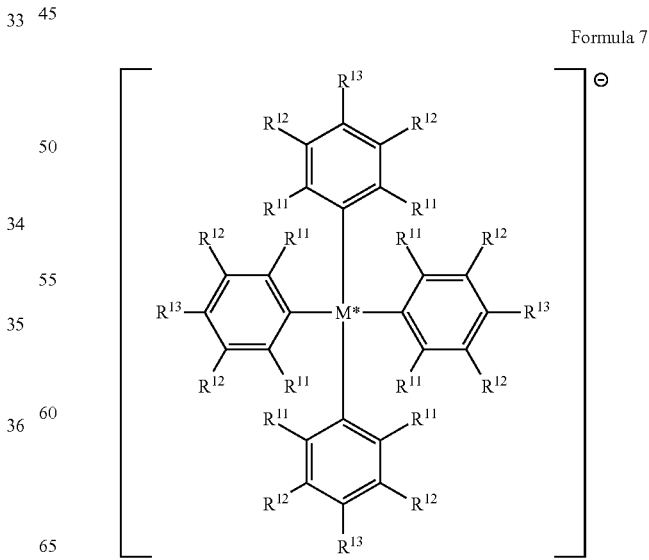

Formula 7 wherein:
  M* is a group 13 atom, preferably B or Al, preferably B;
  each $R^{11}$ is, independently, a halide, preferably a fluoride;
  each $R^{12}$ is, independently, a halide, a $C_6$ to $C_{20}$ substituted aromatic hydrocarbyl group or a siloxy group of the formula —O—Si—$R^a$, where $R^a$ is a $C_1$ to $C_{20}$ hydrocarbyl or hydrocarbylsilyl group, preferably $R^{12}$ is a fluoride or a perfluorinated phenyl group;
  each $R^{13}$ is a halide, a $C_6$ to $C_{20}$ substituted aromatic hydrocarbyl group or a siloxy group of the formula —O—Si—$R^a$, where $R^a$ is a $C_1$ to $C_{20}$ hydrocarbyl or hydrocarbylsilyl group, preferably $R^{13}$ is a fluoride or a $C_6$ perfluorinated aromatic hydrocarbyl group;
  wherein $R^{12}$ and $R^{13}$ can form one or more saturated or unsaturated, substituted or unsubstituted rings, preferably $R^{12}$ and $R^{13}$ form a perfluorinated phenyl ring. Preferably the anion has a molecular weight of greater than 700 g/mol, and, preferably, at least three of the substituents on the M* atom each have a molecular volume of greater than 180 cubic A.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in Girolami, G. S. (1994) "A Simple "Back of the Envelope" Method for Estimating the Densities and Molecular Volumes of Liquids and Solids," *Journal of Chemical Education*, v. 71(11), pp. 962-964. Molecular volume (MV), in units of cubic Å, is calculated using the formula: MV=8.3$V_s$, where $V_s$ is the scaled volume. $V_s$ is the sum of the relative volumes of the constituent atoms, and is calculated from the molecular formula of the substituent using Table A below of relative volumes. For fused rings, the $V_s$ is decreased by 7.5% per fused ring. The Calculated Total MV of the anion is the sum of the MV per substituent, for example, the MV of perfluorophenyl is 183 Å$^3$, and the Calculated Total MV for tetrakis(perfluorophenyl)borate is four times 183 Å$^3$, or 732 Å$^3$.

TABLE A

| Element | Relative Volume |
| --- | --- |
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

Exemplary anions useful herein and their respective scaled volumes and molecular volumes are shown in Table B below. The dashed bonds indicate bonding to boron.

TABLE B

| Ion | Structure of Boron Substituents | Molecular Formula of Each Substituent | $V_S$ | MV Per subst. (Å$^3$) | Calculated Total MV (Å$^3$) |
| --- | --- | --- | --- | --- | --- |
| tetrakis(perfluorophenyl)borate | | $C_6F_5$ | 22 | 183 | 732 |
| tris(perfluorophenyl)-(perfluoronaphthyl)borate | | $C_6F_5$ $C_{10}F_7$ | 22 34 | 183 261 | 810 |
| (perfluorophenyl)tris-(perfluoronaphthyl)borate | | $C_6F_5$ $C_{10}F_7$ | 22 34 | 183 261 | 966 |

TABLE B-continued

| Ion | Structure of Boron Substituents | Molecular Formula of Each Substituent | $V_S$ | MV Per subst. (Å³) | Calculated Total MV (Å³) |
|---|---|---|---|---|---|
| tetrakis(perfluoronaphthyl)borate | | $C_{10}F_7$ | 34 | 261 | 1044 |
| tetrakis(perfluorobiphenyl)borate | | $C_{12}F_9$ | 42 | 349 | 1396 |
| [(C₆F₃(C₆F₅)₂)₄B] | | $C_{18}F_{13}$ | 62 | 515 | 2060 |

The activators may be added to a polymerization in the form of an ion pair using, for example, [M2HTH]+ [NCA]− in which the di(hydrogenated tallow)methylamine ("M2HTH") cation reacts with a basic leaving group on the transition metal complex to form a transition metal complex cation and [NCA]−. Alternatively, the transition metal complex may be reacted with a neutral NCA precursor, such as $B(C_6F5)_3$, which abstracts an anionic group from the complex to form an activated species. Useful activators include di(hydrogenated tallow)methylammonium[tetrakis(pentafluorophenyl)borate](i.e., [M2HTH]B(C₆F5)₄) and di(octadecyl)tolylammonium [tetrakis(pentafluorophenyl)borate] (i.e., [DOdTH]B(C₆F₅)₄).

Activator compounds that are particularly useful in this invention include one or more of: N,N-di(hydrogenated tallow)methylammonium [tetrakis(perfluorophenyl)borate], N-methyl-4-nonadecyl-N-octadecylanilinium [tetrakis(perfluorophenyl)borate], N-methyl-4-hexadecyl-N-octadecylanilinium [tetrakis(perfluorophenyl)borate], N-methyl-4-tetradecyl-N-octadecylanilinium [tetrakis(perfluorophenyl)borate], N-methyl-4-dodecyl-N-octadecylanilinium [tetrakis(perfluorophenyl)borate], N-methyl-4-decyl-N-octadecylanilinium [tetrakis(perfluorophenyl)borate], N-methyl-4-octyl-N-octadecylanilinium [tetrakis(perfluorophenyl)borate], N-methyl-4-hexyl-N-octadecylanilinium [tetrakis(perfluorophenyl)borate], N-methyl-4-butyl-N-octadecylanilinium [tetrakis(perfluorophenyl)borate], N-methyl-4-octadecyl-N-decylanilinium [tetrakis(perfluorophenyl)borate], N-methyl-4-nonadecyl-N-dodecylanilinium [tetrakis(perfluorophenyl)borate], N-methyl-4-nonadecyl-N-tetradecylanilinium [tetrakis(perfluorophenyl)borate], N-methyl-4-nonadecyl-N-hexadecylanilinium [tetrakis(perfluorophenyl)borate], N-ethyl-4-nonadecyl-N-octadecylanilinium [tetrakis(perfluorophenyl)borate], N-methyl-N,N-dioctadecylammonium [tetrakis(perfluorophenyl)borate], N-methyl-N,N-dihexadecylammonium [tetrakis(perfluorophenyl)borate], N-methyl-N,N-ditetradecylammonium [tetrakis(perfluorophenyl)borate], N-methyl-N,N-didodecylammonium [tetrakis(perfluorophenyl)borate], N-methyl-N,N-didecylammonium [tetrakis(perfluorophenyl)borate], N-methyl-N,N-dioctylammonium [tetrakis(perfluorophenyl)borate], N-ethyl-N,N-dioctadecylammonium [tetrakis(perfluorophenyl)borate], N,N-di(octadecyl)tolylammonium [tetrakis(perfluorophenyl)borate], N,N-di(hexadecyl)tolylammonium [tetrakis(perfluorophenyl)borate], N,N-di(tetradecyl)tolylammonium [tetrakis(perfluorophenyl)borate], N,N-di(dodecyl)tolylammonium [tetrakis(perfluorophenyl)borate], N-octadecyl-N-hexadecyl-tolylammonium [tetrakis(perfluorophenyl)borate], N-octadecyl-N-hexadecyl-tolylammonium [tetrakis(perfluorophenyl)borate], N-octadecyl-N-tetradecyl-tolylammonium [tetrakis(perfluorophenyl)borate], N-octadecyl-N-dodecyl-tolylammonium [tetrakis(perfluorophenyl)borate], N-octadecyl-N-decyl-tolylammonium [tetrakis(perfluorophenyl)borate], N-hexadecyl-N-tetradecyl-tolylammonium [tetrakis(perfluorophenyl)borate], N-hexadecyl-N-dodecyl-tolylammonium [tetrakis(perfluorophenyl)borate], N-hexadecyl-N-decyl-tolylammonium [tetrakis(perfluorophenyl)borate], N-tetradecyl-N-dodecyl-tolylammonium [tetrakis(perfluorophenyl)borate], N-tetradecyl-N-decyl-tolylammonium [tetrakis(perfluorophenyl)borate], N-dodecyl-N-decyl-tolylammonium [tetrakis(perfluorophenyl)borate], N-methyl-N-octadecylanilinium [tetrakis(perfluorophenyl)borate], N-methyl-N-hexadecylanilinium [tetrakis(perfluorophenyl)borate], N-methyl-N-tetradecylanilinium [tetrakis(perfluorophenyl)borate], N-methyl-N-dodecylanilinium [tetrakis(perfluorophenyl)borate], N-methyl-N-decylanilinium [tetrakis(perfluorophenyl)borate], and N-methyl-N-octylanilinium [tetrakis(perfluorophenyl)borate].

Additional useful activators and the synthesis thereof, are described in U.S. Ser. No. 16/394,166 filed Apr. 25, 2019, U.S. Ser. No. 16/394,186, filed Apr. 25, 2019, and U.S. Ser. No. 16/394,197, filed Apr. 25, 2019, which are incorporated by reference herein.

In embodiments, the activator is not (and the cation portion of Formula (V), (VI), (VII) and (VII) is not the cation in the formulas below):

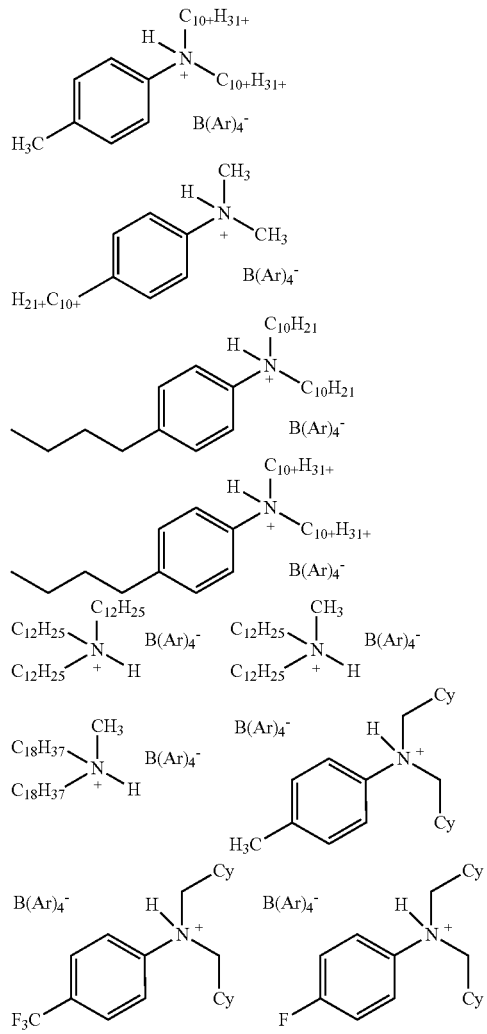

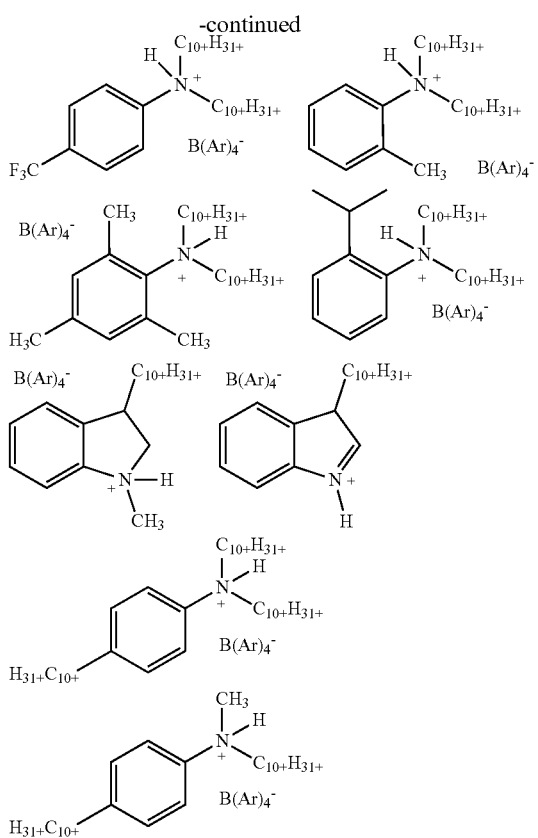

Synthesis

In at least one embodiment, the general synthesis of the activators can be performed using a two-step process. In the first step, an amine or phosphine is dissolved in a solvent (e.g. hexane, cyclohexane, methylcyclohexane, ether, dichloromethane, toluene) and an excess (e.g., 1.2 molar equivalents) of hydrogen chloride is added to form a chloride salt. This salt is typically isolated by filtration from the reaction medium and dried under reduced pressure. The isolated chloride is then heated to reflux with about one molar equivalent of an alkali metal metallate or metalloid (such as a borate or aluminate) in a solvent (e.g. cyclohexane, dichloromethane, methylcyclohexane) to form the desired borate or aluminate along with byproduct alkali metal chloride, the latter of which can typically be removed by filtration.

In at least one embodiment, the general synthesis of the ammonium borate activators can be performed using a two-step process. In the first step, an amine is dissolved in a solvent (e.g. hexane, cyclohexane, methylcyclohexane, ether, dichloromethane, toluene) and an excess (e.g., 1.2 molar equivalents) of hydrogen chloride is added to form an ammonium chloride salt. This salt is typically isolated by filtration from the reaction medium and dried under reduced pressure. The isolated ammonium chloride is then heated to reflux with about one molar equivalent of an alkali metal borate in a solvent (e.g. cyclohexane, dichloromethane, methylcyclohexane) to form the ammonium borate along with byproduct alkali metal chloride, the latter of which can typically be removed by filtration.

A co-activator is a compound capable of alkylating the transition metal complex, such that when used in combination with an activator, an active catalyst is formed. Co-activators can include alumoxanes such as methylalumoxane, modified alumoxanes such as modified methylalumoxane, and aluminum alkyls such trimethylaluminum, tri-isobutylaluminum, triethylaluminum, and tri-isopropylaluminum, tri-n-hexylaluminum, tri-n-octylaluminum, tri-n-decylaluminum or tri-n-dodecylaluminum. Co-activators are typically used in combination with Lewis acid activators and ionic activators when the pre-catalyst is not a dihydrocarbyl or dihydride complex. Sometimes co-activators are also used as scavengers to deactivate impurities in feed or reactors.

III.3 Scavenger

A scavenger can be an additional component of a catalyst system described herein. A scavenger is a compound typically added to facilitate oligomerization or polymerization by scavenging impurities. Some scavengers may also act as activators and may be referred to as co-activators. A co-activator which is not a scavenger may also be used in conjunction with an activator in order to form an active catalyst with a transition metal compound. In some embodiments, a co-activator can be pre-mixed with the transition metal compound to form an alkylated transition metal compound, also referred to as an alkylated catalyst compound or alkylated metallocene. To the extent scavengers facilitate the metallocene compound in performing the intended catalytic function, scavengers, if used, are sometimes considered as a part of the catalyst system.

U.S. Pat. No. 9,409,834 (e.g., at line 37, column 33 to line 61, column 34) provides detailed description of scavengers useful in the process of the present invention for making PAO. The relevant portions in this patent on scavengers, their identities, quantity, and manner of use are incorporated herein in their entirety.

Particularly useful scavengers include tri-n-octylaluminum, triethylaluminum, triisobutylaluminum, tri-n-hexylaluminum, and the like.

IV. Process for Making PAO

The process for making a PAO of the present invention includes a step of contacting a feed comprising a $C_6$-$C_{32}$ alpha-olefin (preferably $C_6$-$C_{30}$, particularly $C_6$-$C_{24}$, $C_6$-$C_{18}$, $C_8$-$C_{18}$, or $C_6$-$C_{12}$) with a catalyst system comprising a metallocene compound described above in a polymerization reactor under polymerization conditions to effect a polymerization reaction to obtain a polymerization reaction mixture comprising vinylidenes, tri-substituted vinylenes, optional di-substituted vinylenes, and optional vinyls; and obtaining an unsaturated PAO product from the polymerization reaction mixture, wherein the unsaturated PAO product comprises vinylidenes, tri-substituted vinylenes, optional di-substituted vinylenes, and optional vinyls.

IV.1 Monomer(s)

The alpha-olefin feed for making the PAO materials of the present invention comprises one or more of $C_6$-$C_{32}$ alpha-olefins (preferably $C_6$-$C_{24}$, particularly $C_6$-$C_{18}$, $C_8$-$C_{18}$, or $C_6$-$C_{12}$). The feed may also comprise ethylene, propylene, $C_4$ alpha-olefins, and $C_5$ alpha-olefins, however each of ethylene, propylene, $C_4$ alpha-olefins (1-butene and 2-methyl-1-propene), and $C_5$ alpha-olefins (1-pentene and various isomers of methyl-1-butene) is independently supplied to the polymerization reactor, at no higher than c1 mol % each, based on the total moles of the alpha-olefins supplied to the polymerization reactor, where c1 can be 25, 20, 10, 5, 4, 3, 2, 1, 0.5, 0.1, or 0.01, for each monomer. Additionally or alternatively, any combination of $C_2$-$C_5$ alpha-olefins (including two or more, three or more, or all four of ethylene, propylene, $C_4$ alpha-olefins, and $C_5$ alpha-olefins) are supplied to the polymerization reactor collectively at no higher than c1 mol %, based on the total moles of the alpha-olefins supplied to the polymerization reactor. Preferably, the alpha-olefin feed is substantially free of ethylene, propylene, $C_4$ alpha-olefins, and $C_5$ alpha-olefins (or completely free of intentionally added $C_2$-$C_5$ alpha-olefins, allowing for impurities present in other feed components). In preferable embodiments, substantially all alpha-olefins in the feed are $C_6$-$C_{30}$ (e.g., $C_6$-$C_{24}$, particularly $C_6$-$C_{18}$, $C_8$-$C_{18}$, or $C_6$-$C_{12}$) alpha-olefins. "Substantially all" means at least 90 mol % (e.g., at least 92 mol %, at least 94 mol %, at least 95 mol %, at least 96 mol %, at least 98 mol %, at least 99%, at least 99.5 mol %, or completely all, allowing for some impurities present in feed components), based on the total moles of the alpha-olefins present in the feed. Preferably, any combination of $C_2$-$C_5$ alpha-olefins are collectively present in the alpha-olefin feed at no higher than c1 mol %, (where c1 can be 25, 20, 10, 5, 4, 3, 2, 1, 0.5, 0.1, or 0.01,) based on the total moles of the alpha-olefins supplied to the polymerization reactor.

In some preferred embodiments, at least a portion (e.g., at least 80 mol %, at least 85 mol %, at least 90 mol %, at least 95 mol %, at least 96 mol %, at least 98 mol %, at least 99%, at least 99.5 mol %, or completely all, allowing for some impurities present in feed components) of the alpha-olefins present in the feed are linear alpha-olefins (LAOs), i.e., those without a branch attached to the carbon backbone thereof. Non-limiting examples of LAOs are 1-hexene, 1-heptene, 1-octene, 1-nonene, 1-decene, 1-dodecene, 1-tetradecene, 1-hexadecene, 1-octadecene, 1-icocene, $C_{22}$, $C_{24}$, $C_{26}$, $C_{28}$, $C_{30}$ and $C_{32}$ LAOs. Without being bound by theory, PAO products made from such LAOs by using the process of the present invention tend to have fewer branches and pendant groups, leading to generally more uniform PAO molecular structures, and hence typically better performance for applications such as lubricant base stocks, lubricant additives, and the like.

Where a single alpha-olefin is fed to the polymerization reactor, the thus obtained PAO is a homopolymer. Homopolymers can have substantially uniform molecular structure, and accordingly desirable physical and rheological properties such as viscosity index. A homopolymer can tend to have pendant groups attached to the carbon backbone with highly uniform length.

In certain situations, a mixture of two, three, or even more alpha-olefins in the feed may be desired to produce a copolymer PAO product. To that end, alpha-olefins with the following combinations can be particularly advantageous: $C_6/C_8$, $C_6/C_{10}$, $C_6/C_{12}$, $C_6/C_{14}$, $C_6/C_{16}$, $C_8/C_{10}$, $C_8/C_{12}$, $C_8/C_{14}$, $C_8/C_{16}$, $C_{10}/C_{12}$, $C_{10}/C_{14}$, $C_{10}/C_{16}$, $C_{10}/C_{18}$, $C_{12}/C_{14}$, $C_{12}/C_{16}$, $C_{12}/C_{18}$, $C_{12}/C_{20}$, $C_6/C_8/C_{10}$, $C_6/C_8/C_{12}$, $C_6/C_8/C_{14}$, $C_6/C_{10}/C_{12}$, $C_6/C_{10}/C_{14}$, $C_8/C_{10}/C_{12}$, $C_8/C_{10}/C_{14}$, $C_8/C_{12}/C_{14}$, $C_{10}/C_{12}/C_{16}$, $C_{10}/C_{12}/C_{18}$, $C_{10}/C_{14}/C_{16}$, $C_{10}/C_{14}/C_{18}$, and the like. Desirably, at least one of the alpha-olefins in the mixture feed can be an LAO. In particular, substantially all of the alpha-olefins in the mixture feed can be LAOs.

Preferred alpha-olefin monomers are mono-olefins containing one C=C bond per monomer molecule, though those olefins containing two or more C=C bonds per monomer molecule can be used as well.

Preferred monomers useful herein include substituted or unsubstituted $C_6$ to $C_{32}$ alpha olefins, or $C_6$ to $C_{20}$ alpha olefins, or $C_6$ to $C_{14}$ alpha olefins, or hexene, heptene, octene, nonene, decene, undecene, dodecene, tetradecene and isomers thereof. Preferably, the polyalphaolefin prepared herein comprises 50 mol % or more (preferably 60 mol % or more, preferably 70 mol % or more, preferably 80 mol % or more, preferably 90 mol % or more, preferably 99 mol % or more) of one or more $C_6$ to $C_{32}$ (preferably $C_6$ to $C_{20}$, preferably $C_8$ to Cis) alpha-olefin monomers.

Useful $C_6$ to $C_{32}$ alpha-olefin monomers include hexene, heptane, octene, nonene, decene, undecene, dodecene, tetradecene, substituted derivatives thereof, and isomers thereof.

Preferably, the monomers comprise $C_6$ to $C_{20}$ alpha-olefins, or $C_6$ to $C_{14}$ alpha-olefins, and/or $C_8$ to $C_{12}$ alpha-olefins.

Preferred olefin monomers include one (alternately two, alternately three) or more of hexene, heptene, octene, nonene, decene, dodecene, and tetradecene.

In an embodiment the PAO is a homopolymer of any $C_8$ to $C_{12}$ alpha-olefin, i.e., the PAO is a homopolymer of 1-hexene, 1-heptene, 1-octene, 1-nonene, 1-decene, 1-undecene, 1-dodecene or 1-tetradecene. Preferably, the PAO is a homopolymer of decene. In another embodiment the PAO is a copolymer comprising decene and one or more of any of the monomers listed above.

In an embodiment, the PAO comprises two or more monomers, or three or more monomers, or four or more monomers, or five or more monomers. For example, a $C_8$, $C_{10}$, $C_{12}$-linear alpha-olefin mixture, or a $C_6$, $C_7$, $C_8$, $C_9$, $C_{10}$, $C_{11}$, $C_{12}$, $C_{13}$, $C_{14}$-linear alpha-olefin mixture, or a $C_6$, $C_8$, $C_{10}$, $C_{12}$, $C_{14}$, $C_{16}$, $C_{18}$-linear alpha-olefin mixture can be used as a feed.

In an alternate embodiment, the PAO comprises less than 50 mol % of $C_2$, $C_3$, and $C_4$ monomers, or less than 40 mol %, or less than 30 mol %, or less than 20 mol %, or less than 10 mol %, or less than 5 mol %, or less than 3 mol %, or 0 mol %. Specifically, in an alternate embodiment, the PAO comprises less than 50 mol % of ethylene, propylene and butene, or less than 40 mol %, or less than 30 mol %, or less than 20 mol %, or less than 10 mol %, or less than 5 mol %, or less than 3 mol %, or 0 mol %. In another embodiment, the PAO comprises less than 40 mol %, or less than 20 mol %, or less than 10 mol %, or less than 5 mol %, or less than 3 mol %, or 0 mol % of ethylene.

In an alternate embodiment, the PAO comprises less than 25 mol % of $C_2$, $C_3$, and $C_4$ monomers, or less than 20 mol %, or less than 15 mol %, or less than 10 mol %, or less than 5 mol %, or less than 1 mol %, or 0 mol %. Specifically, in an alternate embodiment, the PAO comprises less than 25 mol % of ethylene, propylene and butene, or less than 20 mol %, or less than 15 mol %, or less than 10 mol %, or less than 5 mol %, or less than 1 mol %, or 0 mol %. In another embodiment, the PAO comprises less than 25 mol %, or less than 20 mol %, or less than 10 mol %, or less than 5 mol %, or less than 1 mol %, or 0 mol % of ethylene.

In another embodiment, the PAO comprises less than 40 mol % of propylene. In another embodiment, the PAO comprises less than 40 mol % of butene. In another embodiment, the PAO comprises less than 10 mol % of ethylene. In another embodiment, the PAO comprises less than 10 mol % of propylene. In another embodiment, the PAO comprises less than 10 mol % of butene.

In another embodiment, the PAO comprises less than 25 mol % of propylene. In another embodiment, the PAO comprises less than 25 mol % of butene. In another embodiment, the PAO comprises less than 5 mol % of ethylene. In another embodiment, the PAO comprises less than 5 mol % of propylene. In another embodiment, the PAO comprises less than 5 mol % of butene. In another embodiment, the PAO comprises less than 1 mol % of ethylene. In another embodiment, the PAO comprises less than 1 mol % of propylene. In another embodiment, the PAO comprises less than 1 mol % of butene.

The alpha-olefins used herein can be produced directly from ethylene growth process as practiced by several commercial production processes, or they can be produced from Fischer-Tropsch hydrocarbon synthesis from $CO/H_2$ syngas, or from metathesis of internal olefins with ethylene, or from cracking of petroleum or Fischer-Tropsch synthetic wax at high temperature, or any other alpha-olefin synthesis routes. An exemplary feed for this invention can be at least 80 wt % alpha-olefin (preferably linear alpha olefin), preferably at least 90 wt % alpha-olefin (preferably linear alpha olefin), or approximately 100% alpha-olefin (preferably linear alpha olefin). However, alpha-olefin mixtures can also be used as feeds in this invention, especially if the other components are internal-olefins, branched olefins, paraffins, cyclic paraffins, aromatics (such as toluene and or xylenes). These components may have diluent effects and are believed to not have a substantial detrimental effect on the polymerization of alpha-olefins. In other words, the process described herein can selectively convert alpha-olefins in a mixture and leave the other components largely, if not completely, unreacted. This can be particularly useful when ethylene is not present in the mixture. This technology can be used to separate out alpha-olefins from a mixture by selectively reacting them with polymerization or oligomerization catalyst systems, effectively if not completely eliminating the need to separate alpha-olefins from the remainder of the components in a mixed feed stream. This can be economically advantageous, for example, in a process utilizing Fisher-Tropsch synthesis olefin product streams containing alpha-olefins, internal-olefins and branched olefins. Such a mixture can be fed to oligomerization technology as described herein and to selectively react away the alpha-olefin. No separate step to isolate the alpha-olefin may be needed. Another example of the utility of this process involves alpha-olefins produced by the metathesis of internal olefins with ethylene, which may contain some internal olefins. This mixed olefin base stock feed can be reacted as-is in the polymerization/oligomerization process of the present invention, which selectively converts the alpha-olefins into lube products. Thus, one can use the alpha-olefin for the base stock synthesis without having to separate the alpha-olefin from internal olefin. This can bring a significant improvement in process economics. The feed olefins can be the mixture of olefins produced from other linear alpha-olefin process containing $C_4$ to $C_{20}$ alpha-olefins as described in Chapter 3 "Routes to Alpha-Olefins" of the book Alpha Olefins Applications Handbook, Edited by G. R. Lappin and J. D. Sauer, published by Marcel Dekker, Inc. N.Y. 1989.

IV.2 Feed Purification

Olefin feed and or solvents may be treated to remove catalyst poisons, such as peroxides, oxygen, or nitrogen-containing organic compounds or acetylenic compounds before being supplied to the polymerization reactor. For example, the treatment of the linear alpha-olefin with an activated 13 Å molecular sieve and a de-oxygenate catalyst (i.e., a reduced copper catalyst) can increase catalyst productivity (expressed in terms of quantity of PAO produced per micromole of the metallocene compound used) more than 10-fold. Alternatively, the feed olefins and or solvents may be treated with an activated molecular sieve, such as 3 Å, 4 Å, 8 Å, or 13 Å molecular sieve, and/or in combination with an activated alumina or an activated de-oxygenate catalyst. Such treatment can desirably increase catalyst productivity 2- to 10-fold or more.

IV.3 Polymerization Reaction

Many polymerization/oligomerization processes and reactor types used for metallocene-catalyzed polymerization or oligomerization such as solution, slurry, and bulk polymerization or oligomerization processed can be used in this invention. If a solid or supported catalyst is used, a slurry or continuous fixed bed or plug flow process may be suitable. Preferably, the monomers are contacted with the metallocene compound and the activator in the solution phase, bulk phase, or slurry phase, for example in a continuous stirred tank reactor or a continuous tubular reactor. In some embodiments, the temperature in any reactor used herein can be from −10° C. to 250° C., e.g., from 30° C. to 220° C., preferably from 50° C. to 180° C., from 60° C. to 170° C., or from 70° C. to 150° C. In some embodiments, the pressure in any reactor used herein can be from 0.1 to 100 atmospheres, e.g., from 0.5 to 75 atmospheres or from 1 to 50 atmospheres. Alternatively, the pressure is any reactor used herein can be from 1 to 50,000 atmospheres, e.g., from 1 to 25,000 atmospheres. Additionally or alternatively, the monomer(s), metallocene and activator can be contacted for a residence time of 1 second to 100 hours, e.g., 30 seconds to 50 hours, 2 minutes to 6 hours, or 1 minute to 4 hours. Additionally or alternatively, solvent or diluent may be present in the reactor and may include aliphatic solvents, such as butanes, pentanes, hexanes, heptanes, octanes, nonanes, decanes, undecanes, dodecanes, tridecanes, tetradecanes, pentadecanes, hexadecanes, or a combination thereof; preferable solvents can include normal paraffins (such as NORPAR® solvents available from ExxonMobil Chemical Company in Houston, TX), isoparaffin solvents (such as ISOPAR® solvents available from ExxonMobil Chemical Company in Houston, TX), and combinations thereof. These solvents or diluents may typically be pretreated in same manners as the feed olefins.

Suitable non-aromatic diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_4$ to $C_{10}$ alkanes. Suitable solvents also include liquid olefins which may act as monomers or comonomers including $C_3$ to $C_{32}$ alpha-olefins such as propylene, 1-butene, 1-hexene, 1-pentene, 3-methyl-1-pentene, 4-methyl-1-pentene, 1-octene, 1-decene, 1-dodecene, 1-tetradecene, 1-hexadecene, 1-octadecene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In a preferred embodiment the solvents used are $C_6$ to $C_{18}$ alpha-olefins, alternatively $C_8$ to $C_{16}$ alpha-olefins, alternatively $C_8$ to $C_{14}$ alpha-olefins, or mixtures thereof. Mixtures of any of the above listed solvents may be used.

In another embodiment, the solvent is not aromatic, preferably aromatics are present in the solvent at less than 3 wt %, preferably less than 3 wt %, preferably less than 1 wt %, preferably less than 0.5 wt %, preferably less than 0.1 wt % based upon the weight of the solvents. Preferably, the solvent or mixture of solvents is aromatic free.

Preferably the solvent is selected from $C_4$ to $C_{10}$ linear, branched or cyclic alkanes.

Preferably the solvent is essentially free of all aromatic solvents.

Preferably the solvent is selected from one or more $C_6$ to $C_{32}$ alpha olefins, such as one or more $C_8$ to $C_{16}$ alpha olefins.

Preferably the solvent is essentially free of all non-alpha-olefin solvents.

In some embodiments of the invention, where all solvent is the alpha-olefin feed (monomer feed), the pre-catalyst is dissolved in the monomer feed in a first feed tank and the activator is dissolved in the monomer feed in a second feed tank. The pre-catalyst solution is then fed into the reactor separately from the activator solution, and catalyst activation occurs in the reactor. If used, the scavenger can be fed in independently, or with the activator feed, the pre-catalyst feed, or the monomer feed if a separate monomer feed is being used.

In other embodiments of the invention where all solvent is the alpha-olefin feed (monomer feed), the pre-catalyst is dissolved in the monomer feed in a first feed tank and the activator is dissolved in the monomer feed in a second feed tank, and the pre-catalyst solution is premixed with the activator solution in a zone prior to entering the reactor, typically immediately before entering the reactor. Alternately the two solutions are contacted for 1 hour or less, 30 minutes or less, 10 minutes or less, 5 minutes or less, 1 minute or less before entering the reactor.

When $C_4$ to $C_{10}$ linear, branched or cyclic alkanes are used in the process as solvent/diluent, the pre-catalyst and activator can be pre-mixed in a feed tank, and fed into the reactor together.

Regardless of the type of reactor or process, it is typically desirable that the average activity level of the catalyst system be maintained at or above a sufficiently high level, so as to attain a minimum reasonable yield of oligomeric product, relative to monomeric reactant(s). For example, in some embodiments, the catalytic reaction can have an average activity level of at least 800 g/mmol·hr, e.g., at least 900 g/mmol·hr, at least 1,000 g/mmol·hr, at least 1,100 g/mmol·hr, at least 1,200 g/mmol·hr, at least 1,300 g/mmol·hr, at least 1,400 g/mmol·hr, at least 1,500 g/mmol·hr, at least 1,700 g/mmol·hr, at least 1,900 g/mmol·hr, at least 2,100 g/mmol·hr, at least 2,500 g/mmol·hr, or at least 2,800 g/mmol·hr; although average activity levels are not often characterized as being "too high," it is theoretically possible for the average activity level to be so high that control of the reaction product may be difficult to achieve in practice, such that the average catalytic reaction activity level can optionally be less than 1,000 kg/mmol·hr, e.g., less than 500 kg/mmol·hr, in some embodiments. Additionally or alternatively, in some embodiments, the catalytic reaction can provide a minimum reasonable yield (grams of oligomer per grams of monomer feed) of at least 18%, e.g., at least 19%, at least 20%, at least 22%, at least 24%, at least 27%, at least 30%, at least 33%, at least 36%, at least 38%, or at least 40%, based on a reaction time of ~1 hour (~3,600 seconds); although reasonable catalytic yield is not often characterized as being "too high," with a maximum of approximately 100% in a 1—hour reaction time, it is theoretically possible for relatively high yields, particularly high yields in relatively short reaction times, to detrimentally affect the ability to control the reaction product, e.g., such that a maximum reasonable yield may optionally be approximately 100% in a reaction time of ~1 minute or less, e.g., approximately 100% in a reaction time of ~10 minutes or less, approximately 100% in a reaction time of ~30 minutes or less, approximately 100% in a reaction time of ~1 hour or less, approximately 95% in a reaction time of ~1 hour or less, or approximately 90% in a reaction time of ~1 hour or less.

In some embodiments, it can be desirable to attain both relatively low product molecular weight and relatively high product vinylidene content. However, in many metallocene reactions where a vinylidene bond is a significant unsaturation product (at least 30 mol %, relative to the total number of moles of vinyls, vinylidenes, di-substituted vinylenes, and tri-substituted vinylenes), increasing reaction temperature can cause a decrease (or at least no increase) in both molecular weight and vinylidene content. Because reaction temperature can be one of the most ubiquitous ways to control product characterization parameters for a given catalyst system, it can often be a challenge to attain a product having both relatively low molecular weight and relatively high vinylidene content in many conventional systems. Thus, in some preferred embodiments of the invention, the combination of the reaction/polymerization/oligomerization conditions with certain metallocene catalyst systems can advantageously result in both decreasing molecular weight and increasing vinylidene content with increasing reaction temperature, thereby allowing heightened control of desired parameters without having to sacrifice one too much to attain the other. In such preferred embodiments, e.g., by carefully selecting the elements of the metallocene catalyst system, the average activity level of the catalyst system be can be further advantageously maintained at or above a sufficiently high level, so as to attain a minimum reasonable yield of oligomeric product, relative to monomeric reactant(s).

Typically, one or more metallocene compounds, one or more activators, and one or more monomers are contacted to produce polymer or oligomer. These catalysts may be supported and, as such, may be particularly useful in the known slurry, solution, or bulk operating modes conducted in single, series, or parallel reactors. If the catalyst, activator, or co-activator is a soluble compound, the reaction can be carried out in a solution mode. Even if one of the components is not completely soluble in the reaction medium or in the feed solution, either at the beginning of the reaction or during or at later stages of the reaction, a solution or slurry type operation may still be applicable. In any instance, the catalyst system components, dissolved or suspended insolvents, such as toluene or other conveniently available aromatic solvents, or in aliphatic solvent, or in the feed alpha-olefin stream, can be fed into the reactor under inert atmosphere (usually nitrogen or argon blanketed atmosphere) to allow the polymerization or oligomerization to take place.

The polymerization or oligomerization can be run in a batch mode, where all the components are added into a reactor and allowed to react to a pre-designed degree of conversion, either to partial conversion or full conversion. Subsequently, the catalyst can be deactivated by any possible means, such as exposure to air or water, or by addition of alcohols or solvents containing deactivating agents.

The polymerization or oligomerization can additionally or alternatively be carried out in a semi-continuous operation, where feeds and catalyst system components can be continuously and/or simultaneously added to the reactor so as to maintain a constant ratio of catalyst system components to feed olefin(s). When all feeds and catalyst system components are added, the reaction may be allowed to proceed to a pre-determined stage. The reaction can then be discontinued by catalyst deactivation in the same manner as described for batch operation.

The polymerization or oligomerization can additionally or alternatively be carried out in a continuous operation, where feeds and catalyst system components can be continuously and/or simultaneously added to the reactor so to maintain a constant ratio of catalyst system and feed olefins. The reaction product can be continuously withdrawn from the reactor, as in a typical continuous stirred tank reactor (CSTR) operation. Preferably, the process is carried out in a continuous operation, where feeds and catalyst system components are continuously and/or simultaneously added to a reactor so to maintain a constant ratio of catalyst system and feed olefins; and the reaction mixture is continuously withdrawn from the reactor. The residence times of the reactants can be controlled by a pre-determined degree of conversion. The withdrawn product can then typically be quenched in the separate reactor in a similar manner as other operation. In some embodiments, any of the processes to prepare PAOs described herein are continuous processes, which can include the steps of a) continuously introducing a feed stream comprising at least 10 mol % of the one or more $C_6$ to $C_{24}$ alpha-olefins into a reactor, b) continuously introducing the metallocene compound and the activator into the reactor, and c) continuously withdrawing the PAO from the reactor. Preferably the process is carried out in a continuous stirred tank reactor or plug flow reactor. Additionally or alternatively, the continuous process can include the step of maintaining a partial pressure of hydrogen in the reactor of 200 psig (~1.4 MPag) or less, based upon the total pressure of the reactor, e.g., 150 psig (~1.0 MPag) or less, 100 psig (~690 kPag) or less, 50 psig (~350 kPag) or less, 25 psig (~170 kPag) or less, or 10 psig (~69 kPag) or less. Additionally or alternatively the hydrogen, if present in the reactor, in the feed, or in both, at a concentration of 1,000 ppm or less by weight, e.g., 750 wppm or less, 500 wppm or less, 250 wppm or less, 100 wppm or less, 50 wppm or less, 25 wppm or less, 10 wppm or less, or 5 wppm or less.

Preferred reactors can range in size from 2 mL and up. Usually, it is preferable to use reactors larger than one liter in volume for commercial production. The production facility may have one single reactor, or several reactors, arranged in series or in parallel or in both to maximize productivity, product properties, and general process efficiency. The reactors and associated equipment are usually pre-treated to ensure proper reaction rates and catalyst performance. The reaction is usually conducted under inert atmosphere, where the catalyst system and feed components may be out of contact with any catalyst deactivator or poison, e.g., polar oxygen, nitrogen, sulfur, and/or acetylenic compounds.

One or more reactors in series or in parallel may be used in the present invention. The metallocene compound, activator and when required, co-activator, may be delivered as a solution or slurry in a solvent or in the alpha-olefin feed stream, either separately to the reactor, activated in-line just prior to the reactor, or pre-activated and pumped as an activated solution or slurry to the reactor. Polymerizations/oligomerization can be carried out in either single reactor operation, in which monomer, or several monomers, catalyst/activator/co-activator, optional scavenger, and optional modifiers may be added continuously to a single reactor or in series reactor operation, in which the above components can be added to each of two or more reactors connected in series. The catalyst system components can be added to the first reactor in the series. The catalyst system component may alternatively be added to both reactors, with one component being added to first reaction and another component to other reactors. In some embodiments, the metallocene compound can be activated in the reactor in the presence of olefin. Alternatively, the metallocene compound (such as a dichloride form of the metallocene compound) may be pre-treated with an alkylaluminum reagent, especially triisobutylaluminum, tri-n-hexylaluminum, and/or tri-n-octylaluminum, followed by charging into the reactor containing other catalyst system component and the feed olefins, or followed by pre-activation with the other catalyst system component to give the fully activated catalyst, which can then be fed into the reactor containing feed olefins. In another alternative, the pre-catalyst metallocene can be mixed with the activator and/or the co-activator, and this activated catalyst can then be charged into reactor, together with feed olefin stream containing some scavenger or co-activator. In another alternative, the whole or part of the co-activator can be pre-mixed with the feed olefins and charged into the reactor at the same time as the other catalyst solution containing metallocene and activators and/or co-activator.

The catalyst compositions can be used individually or can be mixed with other known polymerization catalysts to prepare polymer or oligomer blends. Monomer and catalyst selection can allow polymer or oligomer blend preparation under conditions analogous to those using individual catalysts. Polymers having increased PDI are available from polymers made with mixed catalyst systems and can thus be achieved. Mixed catalyst can comprise two or more metallocene compounds and or two or more activators.

The PAOs described herein can additionally or alternatively be produced in homogeneous solution processes. Generally, this involves polymerization or oligomerization in a continuous reactor in which the polymer formed and the starting monomer and catalyst materials supplied may be agitated to reduce or avoid concentration or temperature gradients. Temperature control in the reactor can generally be obtained by balancing the heat of polymerization and with reactor cooling by reactor jackets or cooling coils or a cooled side-stream of reactant to cool the contents of the reactor, auto refrigeration, pre-chilled feeds, vaporization of liquid medium (diluent, monomers, or solvent) or combinations of the above. Adiabatic reactors with pre-chilled feeds may additionally or alternatively be used. The reactor temperature may vary with the catalyst used and the product desired. Higher temperatures can tend to give lower molecular weights, and lower temperatures can tend to give higher molecular weights; however, this is not a fixed rule. In general, the reactor temperature preferably can vary between about 0° C. and about 300° C., e.g., from about 10° C. to about 230° C. or from about 25° C. to about 200° C. Usually, it is important to control the reaction temperature as predetermined. In order to produce fluids with narrow polydispersity, such as to promote the highest possible shear stability, it can be useful to control the reaction temperature to obtain minimum of temperature fluctuation in the reactor or over the course of the reaction time. If multiple reactors are used in series or in parallel, it may be useful to keep the temperature constant in a pre-determined value, e.g., to minimize any broadening of molecular weight distribution. In order to produce a product with broader molecular weight distribution, one can adjust the reaction temperature swing or fluctuation, or, as in series operation, the second reactor temperature may be higher than the first reactor temperature. In parallel reactor operation, the temperatures of the two reactors may be independent. Or one can use more than one type of metallocene catalyst.

The pressure in any reactor used herein can vary from about 0.1 atmosphere to about 100 atmospheres (about 1.5 psia to about 1,500 psia), e.g., from about 0.5 atm to about 80 atm (~7 psia to ~1,200 psia) or from about 1.0 atm to about 50 atm (~15 psia to ~750 psia). The reaction can be carried out under an atmosphere of nitrogen or with some hydrogen. Sometimes a small amount of hydrogen may be added to the reactor to improve catalyst performance. When present, the amount of hydrogen can be kept at such a level to improve catalyst productivity, but preferably not induce too much (preferably any significant) hydrogenation of olefins, especially the feed alpha-olefins (the reaction of alpha-olefins into saturated paraffins can be very detrimental to the efficiency of the process). The amount of hydrogen partial pressure is thus preferred to be kept low, e.g., less than 50 psi (350 kPa), less than 25 psi (170 kPa), less than 10 psi (69 kPa), or less than 5 psi (35 kPa); additionally or alternatively, the concentration of hydrogen in the reactant phase, in the reactor and/or feed, can be less than 10,000 ppm (by wt.), e.g., less than 1,000 ppm, less than 500 ppm, less than 100 ppm, less than 50 ppm, less than 25 ppm, or less than 10 ppm.

The reaction time or reactor residence time can depend on the catalyst used, the amount of catalyst used, and the desired alpha-olefin conversion level. Different metallocene compounds typically have different activities. Usually, a higher degree of alkyl substitution on the Cp ring, or bridging can improve catalyst productivity. High amounts of catalyst loading can tend to give higher alpha-olefin conversion at shorter reaction times. However, high amount of catalyst usage can make the production process uneconomical and difficult to manage the reaction heat or to control the reaction temperature. Therefore, it can be useful to choose a catalyst with maximum catalyst productivity to minimize the amount of metallocene and activator needed.

When the catalyst system is a metallocene plus a Lewis Acid or an ionic promoter with NCA component, the metallocene use can be in the range of 0.00001 microgram/gram (mcg/g) to 500 mcg/g of metallocene component relative to alpha-olefin feed, e.g., from 0.0001 mcg/g to 100 mcg/g, and/or the molar ratio of the NCA activator to metallocene can be in the range from 0.001 to 10, e.g., from 0.01 to 5 or from 0.1 to 3. If a co-activator of alkylaluminum compound is used, the molar ratio of the Al to metallocene can be in the range from 1 to 1,000, e.g., from 2 to 500 or from 4 to 400.

Typically, it can be preferable to have the highest possible alpha-olefin conversion (close to 100%) of feed alpha-olefin in shortest possible reaction time. However, in CSTR operation, sometimes it can be beneficial to run the reaction at an optimum alpha-olefin conversion, which can be less than 100% alpha-olefin conversion, but preferably close to 100%. There are also occasions, when partial alpha-olefin conversion can be more desirable, e.g., when a narrow product PDI (Mw/Mn) is desirable, because partial conversion can avoid a PDI broadening effect. If the reaction is conducted to less than 100% conversion of the alpha-olefin, the unreacted starting material after separation from other product and solvents/diluents can be simply removed, or may be recycled to increase the total process efficiency. Conversion, also called alpha-olefin conversion, is determined by dividing the amount (grams) of isolated PAO recovered from the polymerization mixture (after the polymerization has been stopped) by the amount (grams) of alpha-olefin introduced into the reactor. (When reported in %, conversion=(grams isolated PAO/grams alpha-olefin used)×100). Preferably the conversion for the polymerization reactions described herein is 20% or more, alternatively 40% or more, alternatively 60% or more, alternatively 70% or more, alternately 80% or more, alternately 90% or more, alternately 95% or more. Isolated PAO is the PAO product obtained after solvent, unreacted monomer and other volatiles (such as dimer) have been removed (such as by vacuum flash). In some cases, the desired PAO is dimer, and care is taken not to remove the dimeric species along with untreated monomer and/or solvent.

Desirable residence times for any process described herein can be from 1 minute to 20 hours, e.g., from 5 minutes to 10 hours.

Each of these processes may also be employed in single reactor, parallel or series reactor configurations. The process can be carried out in a continuous stirred tank reactor or plug flow reactor, or more than one reactor operated in series or parallel. These reactors may or may not have internal cooling and the monomer feed may or may not be refrigerated. See the general invention of U.S. Pat. No. 5,705,577 for general process conditions.

When a solid supported catalyst is used, a slurry polymerization/oligomerization process generally operates in the similar temperature, pressure, and residence time range as described previously. In a slurry polymerization or oligomerization, a suspension of solid catalyst, promoters, monomer and comonomers are added. The suspension including diluent is intermittently or continuously removed from the reactor. The catalyst is then separated from the product by filtration, centrifuge, or settlement. The fluid is then distilled to remove solvent, any unreacted components and light product. A portion or all of the solvent and unreacted component or light components can be recycled for reuse.

If the catalyst used is un-supported or is a solution catalyst, when the reaction is complete or when the product is withdrawn from the reactor (such as in a CSTR), the product may still contain soluble, suspended, or mixed catalyst system components. These components can preferably be deactivated and/or removed. Any of the usual catalyst deactivation methods or aqueous wash methods can be used to remove the catalyst system component. Typically, the reaction can be deactivated by addition of stoichiometric amount or excess of air, moisture, alcohol, isopropanol, etc. The mixture can then be washed with dilute sodium hydroxide or with water to remove catalyst system components. The residual organic layer may then be subjected to distillation to remove solvent, which can optionally be recycled for reuse. The distillation can further remove any light reaction product, e.g., from $C_{18}$ and less. These light components can be used as diluent for further reaction or can be used as olefinic raw material for other chemical synthesis, as these light olefin by-products may have vinylidene unsaturation, most suitable for further functionalization to convert in high performance fluids. Additionally or alternatively, these light olefin products can be hydrogenated to be used as high quality paraffinic solvents.

Polymerization or oligomerization in absence of hydrogen may be advantageous to provide polymers or oligomers with high degree of unsaturated double bonds. These double bonds can be easily converted into functionalized fluids with multiple performance features. Examples for converting oligomers and/or polymers can be found in preparation of ashless dispersants, e.g., by reacting the polymers with maleic anhydride to give PAO-succinic anhydride which can then reacted with amines, alcohols, and/or polyether alcohols to convert into dispersants, such as disclosed in the book "*Lubricant Additives: Chemistry and Application*," ed. By Leslie R. Rudnick, p. 143-170.

Desirably, in the process of the present invention, due to the structure features of the metallocene compound, the polymerization reaction mixture exiting the polymerization reactor can typically comprise oligomers including vinylidenes, tri-substituted vinylenes, optionally di-substituted vinylenes, and optionally vinyls, optionally residual olefin monomer feed, optionally solvents, and components derived from the catalyst system.

The polymerization reaction mixture can then be quenched, e.g., by the addition of a quenching agent such as water, $CO_2$, methanol, ethanol, mixtures thereof, and the like. Subsequently, the polymerization reaction mixture can be separated to remove the residual monomer, which can be recycled to the polymerization reactor. Monomer removal can be carried out by means such as flashing under vacuum, distillation, or extraction. The resultant mixture can comprise an unsaturated PAO product including vinylidenes, tri-substituted vinylenes, optionally di-substituted vinylenes, and optionally vinyls.

Without being bound by theory, it is believed that, a non-coordinating anion with a small molecular size (e.g. the tetrakis(perfluorophenyl)borate anion) can tend to result in higher selectivity toward vinylidenes and a lower selectivity toward vinyls, as compared to non-coordinating anions with a large molecular size (e.g. the tetrakis(perfluoronaphthyl) borate) anion) when used as the activator for the same metallocene compound of the present invention.

The unsaturated PAO product obtained immediately after monomer removal can contain dimers, trimers, tetramers, pentamers, and even oligomers with a higher degree of polymerization. Extraction or fractionation may be carried out to separate the product into multiple fractions with differing boiling point ranges, corresponding to differing molecular weight range and differing degree of polymerization. For example, dimers can be separated out as a low-viscosity, low boiling point fraction as one grade of product, and the residual material may be used as another unsaturated PAO product grade.

IV.6 Hydrogenation

At least a portion of the unsaturated PAO product can be hydrogenated to obtain an at least partly saturated PAO product. The unsaturated PAO product may be treated to reduce heteroatom-containing compounds to less than 600 ppm by wt. Thereafter, in some embodiments, the treated product can then be contacted with hydrogen and a hydrogenation catalyst to produce an at least partly saturated, hydrogenated PAO product, e.g., at a temperature from 25° C. to 350° C. (e.g., 100° C. to 300° C.), for a time period from 5 minutes to 100 hours (e.g., from 5 minutes to 24 hours), at a hydrogen pressure of from 25 psig to 2,500 psig (~170 kPag to ~17 MPag), such as from 100 psig to 2,000 psig (~690 kPag to ~14 MPag). Further information on hydrogenation of unsaturated PAO products can be found in U.S. Pat. No. 5,573,657 and "Lubricant Base Oil Hydrogen Refining Processes" (page 119 to 152 of Sequeira, Avilino Jr. et al. (1994) *Lubricant Base Oil and Wax Processing*, Marcel Dekker, Inc., NY.

This hydrogenation process can be accomplished, e.g., in a slurry reactor, in a batch operation, or in a continuous stirred tank reactor (CSTR), where the catalyst in 0.001 wt % to 20 wt % of the unsaturated PAO feed (e.g., from 0.01 wt % to 10 wt %), hydrogen, and the uPAOs can be continuously added to the reactor to allow for certain residence time, e.g., 5 minutes to 10 hours, to allow desired (e.g., substantially complete) hydrogenation of the unsaturated olefins. The amount of catalyst added may usually be very small, just to compensate for catalyst deactivation. The catalyst and hydrogenated PAO can be continuously withdrawn from the reactor. The product mixture can be filtered, centrifuged, or settled to remove the solid hydrogenation catalyst. The catalyst can be regenerated and reused, if desired. The hydrogenated PAO can be used as-is or further distilled or fractionated to a desired level. In some cases, when the hydrogenation catalyst show little or no catalyst deactivation over long term operation, the stir tank hydrogenation process can be carried out in a manner where a fixed amount of catalyst is maintained in the reactor, such as from 0.1 wt % to 10% of the total reactant, with mostly (or only) hydrogen and PAO feed continuously added at certain feed rate, and with predominantly (or only) hydrogenated PAO was withdrawn from the reactor.

The hydrogenation process can additionally or alternatively be accomplished by a fixed bed process, in which the solid catalyst can be packed inside a tubular reactor and heated to reactor temperature. Hydrogen and PAO feed can be fed through the reactor simultaneously from the top or bottom or counter-current, e.g., to maximize the contact between hydrogen, PAO, and catalyst and to allow superior heat management. The feed rate of the PAO and hydrogen can be adjusted to give proper residence time, e.g., to allow desired (typically substantially complete) hydrogenation of the unsaturated PAOs in the feed. The hydrogenated PAO fluid can be used as-is or further distilled or fractionated to a desired level. Usually, the hydrogenated PAO product can have a bromine number of 2.0 or less.

IV.7 Functionalization

At least a portion of the unsaturated PAO product can be reacted with a chemical reagent to obtain an at least partly functionalized PAO product. However, due to the individual nature of functionalization reactions, the specificity of potential side products or by-products to be avoided, the breadth of potentially desired functionality, and thus the breadth of potential reaction conditions available or sufficient to attain desired functionality, it can be difficult to specify an appropriately set of conditions, reactors, chemical reagents, and/or catalysts/additives/etc. to encompass them all. Nevertheless, conventional functionalization techniques, as well as their reaction parameters, are known to those skilled in the chemical arts, allowing partially or completely functionalized PAO products sporting any one or more of a variety of functional groups to be readily attainable. In the case of substantially or completely functionalized PAO products, in some embodiments, the bromine number may be 2.0 or less. Unless otherwise indicated, bromine number values in the present invention are determined according to ASTM D 1159.

Kinematic viscosities (KV40 and KV100) are determined according to ASTM D445 (at 40° C. and 100° C.). Viscosity index (VI) is determined according to ASTM D2270. Noack volatility (NV) is determined according to ASTM D5800.

V. Lubricant Base Stock

The unsaturated PAO products and the hydrogenated PAO products of the present invention, advantageously obtainable by using the processes of the present invention, can be used as a base stock for lubricating oil compositions. Preferably the hydrogenated PAO product having a bromine number no greater than 2.0 is used as a lubricating oil base stock. The base stock can be at any viscosity grade useful for any particular lubricating oil composition. The base stocks of the present invention can be blended with each other, other API Group I, II, III, IV, or V base stocks, lubricating additive packages, and/or the like, to form a lubricating oil composition. "Lubricating oil," "lubricating oil composition," and "lubricant" are used herein interchangeably. The lubricants can include internal combustion engine oils, gas turbine oils, automobile drive line fluids, power transfer fluids (e.g., hydraulic oil), processing oils, heat transfer oils (e.g., transformer oils), industrial lubricants, gear box lubricants, and the like, as well as combinations thereof.

VI. Additional Embodiments

Additionally or alternatively, the present invention can include one or more of the following embodiments:

1. A process for producing a poly alpha-olefin, PAO, the process comprising:
   contacting a feed comprising a $C_6$-$C_{32}$ alpha-olefin with a catalyst system comprising an unsymmetrical metallocene compound, a non-aromatic hydrocarbon soluble activator compound, and a non-aromatic hydrocarbon solvent in a polymerization reactor under polymerization conditions to effect a polymerization reaction to obtain a polymerization reaction mixture comprising vinylidenes, tri-substituted vinylenes, optional di-substituted vinylenes, and optional vinyls; and
   obtaining an unsaturated PAO product from the polymerization reaction mixture, wherein the unsaturated PAO product comprises vinylidenes, optional tri-substituted vinylenes, optional di-substituted vinylenes, and optional vinyls.

2. The process of paragraph 1, wherein the metallocene compound is represented by Formula (I) described herein, preferably at least one of $R^1$, $R^2$, and $R^3$ is not hydrogen and at least one of $R^1$, $R^2$, and $R^3$ is hydrogen.

3. The process of paragraph 1, wherein the metallocene compound is represented by Formula (II) described herein.

4. The process of paragraph 1, wherein the metallocene compound is represented by Formula (III) described herein.

5. The process of paragraph 1, wherein the metallocene compound is represented by Formula (IV) described herein.

6. The process of paragraphs 2 or 4, where in Formula (I) or (III) $R^2$ is hydrogen and one of $R^1$ and $R^3$ is a substituted or unsubstituted linear, branched, or cyclic $C_1$-$C_6$ hydrocarbyl group, and the other of $R^1$ and $R^3$ of $R^1$ and $R^3$ is a hydrogen, and or $R^6$ and $R^7$, or $R^7$ and $R^{17}$, or $R^{17}$ and $R^{18}$, taken together with the respective carbon atoms in the indenyl ring to which they are directly connected, form a ring annelated to the indenyl ring, preferably the ring annelated to the indenyl ring comprises one or more saturated carbon atoms.

7. The process of paragraphs 2 to 6, where in any of Formulas (I), (II), (III), or (IV), M is Hf or Zr.

8. The process of paragraphs 1 to 7 wherein the non-aromatic-hydrocarbon soluble activator compound is represented by Formula (V):

$$[R^{1'}R^{2'}R^{3'}EH]_{d+}[Mt^{k+}Q_n]^{d-} \qquad (V)$$

wherein: E is nitrogen or phosphorous; d is 1, 2 or 3; k is 1, 2, or 3; n is 1, 2, 3, 4, 5, or 6; n–k=d; $R^{1'}$, $R^{2'}$, and $R^{3'}$ are independently $C_1$ to $C_{50}$ hydrocarbyl group optionally substituted with one or more alkoxy groups, silyl groups, a halogen atoms, or halogen containing groups wherein $R^{1'}$, $R^{2'}$, and $R^{3'}$ together comprise 15 or more carbon atoms; Mt is an element selected from group 13 of the Periodic Table of the Elements; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

9. The process of paragraphs 1 to 7, wherein the non-aromatic-hydrocarbon soluble activator compound is represented by Formula (VI):

wherein: E is nitrogen or phosphorous; $R^{1'}$ is a methyl group; $R^{2'}$ and $R^{3'}$ are independently is $C_4$-$C_{50}$ hydrocarbyl group optionally substituted with one or more alkoxy groups, silyl groups, a halogen atoms, or halogen containing groups wherein $R^{2'}$ and $R^{3'}$ together comprise 14 or more carbon atoms; is boron; and $R^{4'}$ $R^{5'}$ $R^{6'}$, and $R^{7'}$ are independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

10. The process of paragraphs 1 to 7, wherein the non-aromatic-hydrocarbon soluble activator compound is represented by Formula (VII) or Formula (VIII):

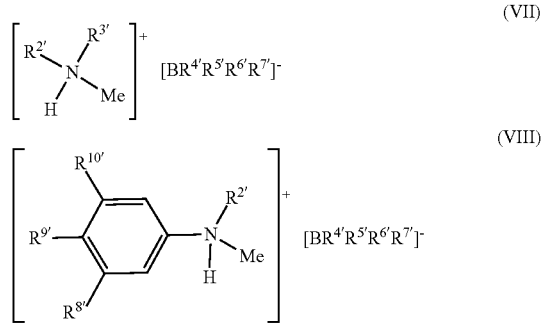

wherein: N is nitrogen; $R^{2'}$ and $R^{3'}$ are independently is $C_6$-$C_{40}$ hydrocarbyl group optionally substituted with one or more alkoxy groups, silyl groups, a halogen atoms, or halogen containing groups wherein $R^2$ and $R^3$ in Formula (VII) together comprise 14 or more carbon atoms and $R^{2'}$ in Formula (VIII) comprises 13 or more carbon atoms; $R^{8'}$, $R^{9'}$, and $R^{10'}$ are independently a $C_4$-$C_{30}$ hydrocarbyl or substituted $C_4$-$C_{30}$ hydrocarbyl group; B is boron; and $R^{4'}$, $R^{5'}$, $R^{6'}$, and $R^{7'}$ are independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

11. The process of paragraph 9 or 10 wherein $R^{4'}$, $R^{5'}$, $R^{6'}$, and $R^{7'}$ are pentafluorophenyl.

12. The process of paragraph 10 wherein $R^{8'}$ and $R^{10'}$ are hydrogen atoms and $R^{9'}$ is a $C_4$-$C_{30}$ hydrocarbyl group which is optionally substituted with one or more alkoxy groups, silyl groups, a halogen atoms, or halogen containing groups.

13. The process of paragraph 11 wherein $R^{9'}$ is a $C_8$-$C_{22}$ hydrocarbyl group which is optionally substituted with one or more alkoxy groups, silyl groups, a halogen atoms, or halogen containing groups.

14. The process of paragraph 10 wherein $R^{2'}$ and $R^{3'}$ are independently a $C_{12}$-$C_{22}$ hydrocarbyl group.

15. The process of any of paragraphs 1 to 14 wherein the solvent is essentially free of all aromatic solvents, such as toluene.

16. The process of any of paragraphs 1 to 15 wherein the solvent is selected from $C_4$ to $C_{10}$ linear, branched or cyclic alkanes.

17. The process of any of paragraphs 1 to 16 wherein the solvent is selected from one or more $C_6$ to $C_{32}$ alpha olefins, such as $C_8$ to $C_{16}$ alpha olefins.

18. The process of any of paragraphs 1 to 15 which is wherein the solvent is essentially free of all non-alpha-olefin solvents.

19. The process of any of paragraphs 1 to 18 wherein: the process comprises obtaining an unsaturated PAO product from the polymerization reaction mixture, wherein the polymerization reaction exhibits a selectivity toward greater than or equal to about 80 mol % vinylidenes, based on total moles of vinyls, vinylidenes, di-substituted vinylenes, and tri-substituted vinylenes in the unsaturated PAO product.

20. The process of any of paragraphs 1 to 19, wherein the conversion is about 10% or more and the polymerization reaction exhibits a selectivity toward greater than or equal to about 80 mol % vinylidenes, based on total moles of vinyls, vinylidenes, di-substituted vinylenes, and tri-substituted vinylenes in the unsaturated PAO product.

21. The process of any of paragraphs 1 to 20, wherein the polymerization reaction exhibits a selectivity toward a combination of greater than or equal to about 90 mol % vinylidenes, from 0.5 mol % to 6 mol % tri-substituted vinylenes, less than or equal to about 2.5 mol % di-substituted vinylenes, and less than or equal to about 1.5 mol % vinyls, based on total moles of vinyls, vinylidenes, di-substituted vinylenes, and tri-substituted vinylenes in the unsaturated PAO product.

22. The process of paragraph 21, wherein the polymerization reaction exhibits a selectivity toward a combination of vinylidenes of equal to or greater than 95 mol %; tri-substituted vinylenes of less than 2.5 mol %; di-substituted vinylenes of 1.0 mol % or less; and vinyls of 1.5 mol % or less, based on total moles of vinyls, vinylidenes, di-substituted vinylenes, and tri-substituted vinylenes in the unsaturated PAO product.

23. The process of paragraph 22, wherein the polymerization reaction exhibits a selectivity towards a combination of vinylidenes and tri-substituted vinylenes of collectively greater than 95.0 mol %, and a combination of di-substituted vinylenes and vinyls of collectively less than 5.0 mol %, based on total moles of vinyls, vinylidenes, di-substituted vinylenes, and tri-substituted vinylenes in the unsaturated PAO product.

24. The process of any of paragraphs 1 to 23, wherein the polymerization reaction results in the unsaturated PAO product having a number average molecular weight (Mn) of 2500 g/mol or less, as measured by $^1$H NMR, preferably 1000 g/mol or less.

25. The process of any of paragraphs 1 to 24, wherein: the polymerization conditions comprise a reaction temperature from 40° C. to 180° C.; an average activity level of at least 1,500 g/mmol·hr; the polymerization reaction mixture exhibits a conversion of at least 10%; or a combination thereof.

26. The process of any of paragraphs 1 to 25, further comprising: a) contacting the unsaturated PAO product with hydrogen to convert at least a portion of the unsaturated PAO product to a hydrogenated PAO product; b) contacting the unsaturated PAO product with a chemical reagent to convert at least a portion of the unsaturated PAO product to a functionalized PAO product; or a combination thereof.

27. The process of any of paragraphs 1 to 26, wherein any combination of $C_2$-$C_5$ alpha-olefins are collectively present in the alpha-olefin feed at no higher than 25 mol %, based on the total moles of the alpha-olefins supplied to the polymerization reactor.

28. The process of any of paragraphs 1 to 27 wherein the unsaturated PAO product comprises dimer.

29. The process of any of paragraphs 1 to 27 wherein the unsaturated PAO product is represented by the following Formula (F-1):

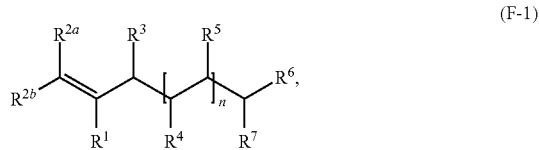

(F-1)

where $R^1$, $R^{2a}$, $R^{2b}$, $R^3$, each of $R^4$ and $R^5$, $R^6$, and $R^7$, the same or different at each occurrence, independently represents a hydrogen or a substituted or unsubstituted hydrocarbyl, and n is a non-negative integer corresponding to the degree of polymerization, preferably $R^1$ is unsubstituted hydrocarbyl, both $R^{2a}$ and $R^{2b}$ are hydrogen, and n is 0.

30. The process of any of paragraphs 1 to 29 wherein the $C_6$-$C_{32}$ alpha-olefin, the metallocene compound and the activator are contacted in the solution phase or bulk phase in a continuous stirred tank reactor or a continuous tubular reactor.

31. The process of any of paragraphs 1 to 30, wherein the process is carried out in a continuous operation, where feeds and catalyst system components are continuously and/or simultaneously added to a reactor so to maintain a constant ratio of catalyst system and feed olefins; and the reaction mixture is continuously withdrawn from the reactor.

32. The process of any of paragraphs 1 to 30, wherein the process is a continuous processes.

33. The process of any of paragraphs 1 to 30, wherein the process is a continuous processes which includes the steps of: a) continuously introducing a feed stream comprising at least 10 mol % of the one or more $C_6$ to $C_{24}$ alpha-olefins into a reactor, b) continuously introducing the metallocene compound and the activator into the reactor, and c) continuously withdrawing the PAO product from the reactor.

34. The process of any of paragraphs 1 to 30, wherein the process is carried out in a continuous stirred tank reactor or plug flow reactor.

35. The process of any of paragraphs 1 to 34, wherein the feed comprises octene, decene, octene and decene, or octene, decene and dodecene.

36. The process of any of paragraphs 1 to 35, wherein the feed comprises a single alpha-olefin monomer or a combination of two or more alpha-olefin monomers.

37. The process of any of paragraphs 1 to 36, wherein the feed comprises a single alpha-olefin monomer selected from the group consisting of: hexene, heptene, octene, nonene, decene, dodecene, tetradecene, and hexadecene.

38. The process of any of paragraphs 1 to 36, wherein the feed comprises two or more alpha-olefin monomers selected from the group consisting of: hexene, heptene, octene, nonene, decene, dodecene, tetradecene, and hexadecene.

39. The process of any of paragraphs 1 to 38, wherein the PAO is a homopolymer of 1-hexene, 1-heptene, 1-octene, 1-nonene, 1-decene, 1-undecene, 1-dodecene, 1-tetradecene, or 1-hexadecene.

40. The process of any of paragraphs 1 to 38, the PAO is a copolymer of decene and one or more of 1-hexene, 1-heptene, 1-octene, 1-nonene, 1-decene, 1-undecene, 1-dodecene, 1-tetradecene, or 1-hexadecene.

41. The process of any of paragraphs 1 to 40, wherein the $C_6$-$C_{32}$ alpha-olefin, the metallocene compound and the activator are contacted in the solution phase, bulk phase, or slurry phase in a continuous stirred tank reactor or a continuous tubular reactor.

42. The process of any of paragraphs 1 to 41, wherein the polymerization temperature is above 100° C., the conversion is 50% or more and the unsaturated PAO product has about 80 mol % or more vinylidenes, based on total moles of vinyls, vinylidenes, di-substituted vinylenes, and tri-substituted vinylenes in the unsaturated PAO product.

43. The process of any of paragraphs 1 to 41, wherein the polymerization temperature is above 110° C., the conversion is 50% or more and the unsaturated PAO product has about 90 mol % or more vinylidenes, based on total moles of vinyls, vinylidenes, di-substituted vinylenes, and tri-substituted vinylenes in the unsaturated PAO product.

44. The process of any of paragraphs 1 to 43 wherein the unsaturated PAO product is represented by formula:

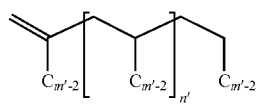

wherein C is a hydrocarbon chain of length m'-2, each m' is independently 4, 5, 6, 7, 8, 9, 10, 11, 12, 13, 14, 15, or 16 and is the carbon number of the monomer(s) used in the polymerization, and n' is 0, 1, 2, 3, 4, 5, 6, 7, 8, 9, or 10.

45. A fuel or lubricant comprising the PAO produced according to the process of any of paragraphs 1 to 44.

46. A functionalized PAO comprising the reaction product of: 1) a heteroatom containing group, and 2) a PAO produced by the process of any of paragraphs 1 to 44, where the heteroatom containing group comprises one or more sulfonates, amines, aldehydes, alcohols, or acids, preferably the heteroatom containing group comprises an epoxide, succinic acid, maleic acid or maleic anhydride, alternately the heteroatom containing group comprises one or more of acids, esters, anhydrides, acid-esters, oxycarbonyls, carbonyls, formyls, formylcarbonyls, hydroxyls, and acetyl halides.

47. The process of any of paragraphs 1 to 44, said process having productivity of at least 4,500 g/mmol/hr, wherein the process comprises: contacting, at a temperature of from 35° C. to 150° C.

48. The process of any of paragraphs 1 to 44, or 47, further comprising hydrogenating at least a portion of said poly alpha-olefin, then formulating a fuel or lubricating composition comprising the product of hydrogenating at least a portion of said polyalpha-olefin.

49. The process of any of paragraphs 1 to 44, or 47, further comprising functionalizing at least a portion of said PAO; then formulating a fuel or lubricating composition comprising the product of functionalizing at least a portion of said PAO.

EXPERIMENTAL

Preparation of Pre-Catalysts

All manipulations with air and moisture sensitive compounds were performed either in an atmosphere of thoroughly purified argon using standard Schlenk techniques or in a controlled atmosphere glove box (Vacuum Atmospheres Co.).

Tetrahydrofuran (THF, Merck=Merck KGaA, Darmstadt, Germany) and diethyl ether (Merck) for synthesis were typically purified by distillation over LiAlH$_4$, and stored over sodium benzophenone ketyl under an inert atmosphere; prior to use, the solvents were distilled from the benzophenone ketyl. Hydrocarbon solvents such as toluene (Merck) and hexanes (Merck) were typically distilled over CaH$_2$, and were stored over Na/K alloy under an inert atmosphere; prior to use, the solvents were distilled from the Na/K alloy. Methylene chloride (and CCl$_2$D$_2$ for NMR measurements) was typically distilled and stored over CaH$_2$ under an inert atmosphere; prior to use, the solvent was distilled from the CaH$_2$. Celite (Aldrich) was dried in a vacuum oven at 180° C. p-Toluenesulfonic acid (TsOH, Aldrich), 2-methylindan-1-one (Aldrich), N-butyl lithium (1.6 M in hexane, Aldrich), hexane (Aldrich anhydrous), 3-chloropropanoyl chloride (Acros), potassium tert-butoxide (Acros), iodomethane (Acros), Na$_2$SO$_4$ (Akzo Nobel), methanol (Merck), ethylene glycol (Merck), sodium lump (Merck), potassium hydroxide (KOH, Merck), AlCl$_3$ (Merck), 1 and 2 M HCl (diluted as needed; Reachim, Moscow, Russia), NaBH$_4$ (Aldrich), anhydrous K$_2$CO$_3$ (Merck), MgSO$_4$ (Merck), MeMgI (3 M in Et$_2$O, Sigma-Aldrich) CH$_3$I (Sigma-Aldrich), isoButyl bromide (Sigma-Aldrich), Me$_5$CpHfCl$_3$ (Strem Chemicals), 1,2,3,5-tetrahydro-s-indacene (GLSyntech), hydrazine hydrate (Merck), silica gel 60 (40-63 um; Merck) and CDCl$_3$ (Deutero GmbH) were used as received.

Analytical and semi-preparative liquid chromatography was performed using a Waters Delta 600 HPLC system including a 996 Photodiode Array Detector, Nova-Pack C$_{18}$ or HR Silica (60A, 6 μm, 3.9 and 19×300 mm) and Symmetry C$_{18}$ (5 m, 4.6×250 mm) columns. MPLC (Medium Pressure Liquid Chromatography, pressure 5-15 bars) was performed using MPLC glass columns and fittings (Ace Glass), a PD5130 pump drive equipped with a J1 gear-well pump head (Heidolph), a 996 Photodiode Array Detector and a Fraction Collector II (Waters Corp.). $^1$H and $^{13}$C spectra were recorded with a Brucker Avance-400 spectrometer. Chemical shifts for $^1$H and $^{13}$C were measured relative to tetramethylsilane (TMS). $^1$H NMR spectral assignments were made on the basis of double resonance and Nuclear Overhauser Effect (NOE) experiments. CHN microanalyses were done using a CHN—O-Rapid analyzer (Heraecus Ltd., Banau, Germany).

Synthesis of Pentamethylcyclopentadienyl(1,6,6-trimethyl-1,5,6,7-tetrahydro-s-indacenyl)hafnium(IV) dimethyl (Cat ID=C)

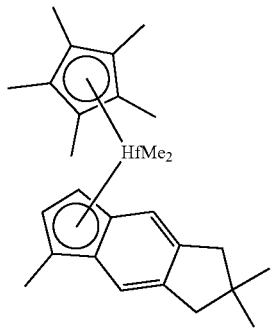

2,2-Dimethylindan-1-one

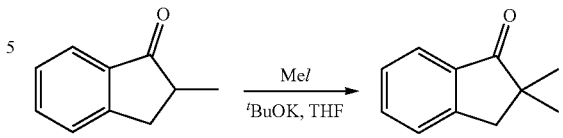

To a solution of 176 g (1.21 mol) of 2-methylindan-1-one and 205 g (1.44 mol, 1.2 equiv.) of methyl iodide in 200 ml of THF cooled to 0° C. a solution of 176 g (1.57 mol, 1.3 eq.) of potassium tert-butoxide in 1,200 ml of THF was added dropwise for 4 hours. The reaction mixture was stirred overnight at room temperature and then poured into 2 liters of water. Crude product was extracted with 300 ml of hexane and then 2×300 ml of dichloromethane. The combined organic extract was dried over K$_2$CO$_3$, passed through a short pad of silica gel 60 (40-63 um), and the elute was evaporated to dryness to give red oil. This oil was then distilled in vacuum to give 185 g (96%) of 2,2-dimethylindan-1-one as yellowish oil which crystallizes at room temperature, b.p. 76-78° C./5 mm Hg.

Anal. calc. for C$_{11}$H$_{12}$O: C, 82.46; H, 7.55. Found: C, 82.24; H, 7.61.

$^1$H NMR (CDCl$_3$): δ 7.76 (d, J=7.6 Hz, $^1$H), 7.59 (dt, J=7.6, 1.2 Hz, $^1$H), 7.44-7.35 (m, $^2$H), 3.00 (s, $^2$H), 1.24 (s, $^6$H). $^{13}$C{$^1$H} NMR (CDCl$_3$): δ 211.38, 152.18, 135.30, 134.77, 127.37, 126.59, 124.40, 45.43, 42.81, 25.22.

2,2-Dimethylindane

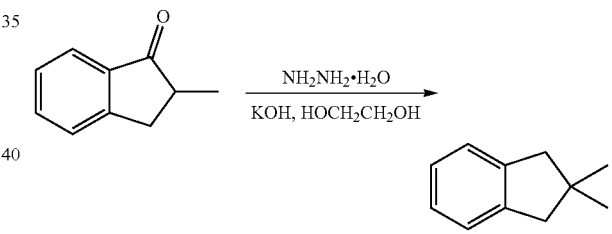

A mixture of 129 g (~2.3 mol) of KOH, 182.5 g (1.14 mol) of 2,2-dimethylindan-1-one and 144 ml of hydrazine hydrate in 850 ml of ethylene glycol was refluxed for 5 hours. Then, the reflux condenser was replaced by a Claisen distillation head with condenser, and a mixture of H$_2$O, NH$_2$NH$_2$, product and ethylene glycol was distilled off until the distillation temperature reached 195° C. The residue was then allowed to cool to room temperature, 300 ml of ethylene glycol, second portion of 2,2-dimethylindan-1-one (182.5 g, 1.139 mol) and hydrazine hydrate (144 ml) was added, and the reduction procedure was repeated as described above. The upper layer of the combined distillate (from two successive reductions) was separated, and the aqueous phase was diluted with 1,000 ml of water. Crude product was extracted with 3×300 ml of dichloromethane. The combined organic extract was washed by 1 M HCl, dried over K$_2$CO$_3$, passed through a short pad of silica gel 60 (40-63 um), and the elute was evaporated to dryness. The residue was distilled in vacuum to give 290 g (87%) of 2,2-dimethylindane as colorless liquid, b.p. 73.5° C./20 mm Hg.

Anal. calc. for C$_{11}$H$_{14}$: C, 90.35; H, 9.65. Found: C, 90.50; H, 9.73.

$^1$H NMR (CDCl$_3$): (7.19-7.08 (m, 4H), 2.72 (s, 4H), 1.15 (s, 6H). $^{13}$C{$^1$H} NMR (CDCl$_3$): δ 143.51, 125.93, 124.70, 47.70, 40.05, 28.77.

6,6-dimethyl-3,5,6,7-tetrahydro-s-indacen-1(2H)-one

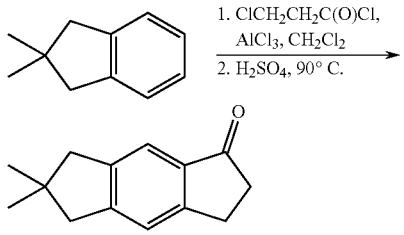

To a stirred suspension of 165 g (1.24 mol) of AlCl$_3$ in 900 ml of dichloromethane a solution of 144.4 g (1.14 mol) of 3-chloropropanoyl chloride and 165.6 g (1.13 mol) of 2,2-dimethylindane in 300 ml of dichloromethane was added dropwise at room temperature over 3 hours. This mixture was stirred additionally for 3 hours at room temperature and then poured on 1,000 g of crushed ice. The organic layer was separated, and the aqueous layer was extracted with 3×200 ml of dichloromethane. The combined organic extract was washed by aqueous K$_2$CO$_3$, dried over K$_2$CO$_3$, passed through a short pad of silica gel 60 (40-63 um), and then evaporated to dryness to give crude 3-chloro-1-(2,2-dimethyl-2,3-dihydro-1H-inden-5-yl)propan-1-one as dark oily liquid. This liquid was added at room temperature to 3,000 ml of 96% sulfuric acid, and the obtained mixture was stirred at room temperature. The resulting dark solution was heated for 40 minutes to 90° C. and stirred additionally for one hour at the same temperature. After cooling to room temperature the reaction mixture was poured on 6,000 g of crushed ice and 4,000 ml of cold water. Then, 2 liter of dichloromethane was added. The organic layer was separated, and the aqueous layer was extracted with dichloromethane (100 ml per 900 ml of the aqueous phase). The combined organic extract was washed by cold water and aqueous K$_2$CO$_3$, dried over K$_2$CO$_3$, and passed through a short pad of silica gel 60 (40-63 um). The elute was evaporated to dryness to give a slightly yellowish solid mass. Recrystallization of the later from 600 ml of n-hexane (hot→r.t.) gave 115.6 g (51%) of 6,6-dimethyl-3,5,6,7-tetrahydro-s-indacen-1(2H)-one as a white crystalline material.

Anal. calc. for C$_{14}$H$_{16}$O: C, 83.96; H, 8.05. Found: C, 84.19; H, 8.22.

$^1$H NMR (CDCl$_3$): (7.52 (s, 1H), 7.23 (s, 1H), 3.09-3.02 (m, 2H), 2.75 (s, 2H), 2.73 (s, 2H), 2.70-2.64 (m, 2H), 1.15 (s, 6H). $^{13}$C{$^1$H} NMR (CDCl$_3$): (206.53, 154.39, 152.31, 143.46, 135.89, 122.55, 119.36, 47.74, 46.74, 40.69, 36.61, 28.42, 25.52.

2,2-Dimethyl-1,2,3,5-tetrahydro-s-indacene

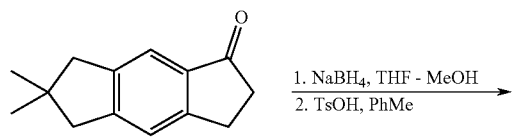

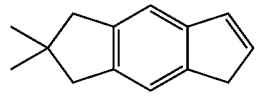

To a solution of 115.6 g (0.577 mol) of 6,6-dimethyl-3,5,6,7-tetrahydro-s-indacen-1(2H)-one in 600 ml of THF cooled to 5° C. 33 g (0.872 mol) of NaBH$_4$ was added. Further on, 300 ml of methanol was added dropwise to this mixture by vigorous stirring for ca. 5 hours at 5° C. This mixture was stirred overnight at room temperature and then evaporated to dryness. To the obtained white mass 1,000 ml of dichloromethane and 1,000 ml of water were added, and the resulting mixture was acidified by 2 M HCl to pH~4. The organic layer was separated, and the aqueous layer was extracted with 2×250 ml of dichloromethane. The combined organic extract was dried over Na$_2$SO$_4$ and then evaporated to dryness to give a white solid mass. To a solution of this mass in 1,500 ml of toluene 0.4 g of TsOH was added, this mixture was rapidly heated to reflux, refluxed with Dean-Stark head for 15 minutes, and then quickly cooled to room temperature using water bath. The resulting solution was washed by 10% aqueous K$_2$CO$_3$. The organic layer was separated, the aqueous layer was extracted with 2×150 ml of dichloromethane. The combined organic extract was dried over K$_2$CO$_3$ and then passed through a short pad of silica gel 60 (40-63 um). The silica gel layer was additionally washed by 250 ml of dichloromethane. The combined organic elute was evaporated to dryness to give a slightly yellowish liquid which was then distilled in vacuum to give 94.1 g (84%) of 2,2-dimethyl-1,2,3,5-tetrahydro-s-indacene (b.p. 105° C./7 mm Hg) as a colorless liquid.

Anal. calc. for C$_{14}$H$_{16}$: C, 91.25; H, 8.75. Found: C, 91.37; H, 8.92.

$^1$H NMR (CDCl$_3$): δ 7.25 (s, 1H), 7.18 (s, 1H), 6.81 (m, 1H), 6.45 (m, 1H), 3.32 (s, 2H), 2.73 (s, 4H), 1.15 (s, 6H). $^{13}$C{$^1$H} NMR (CDCl$_3$): δ 143.34, 142.13, 141.64, 140.27, 133.14, 132.13, 120.35, 117.32, 47.65, 47.61, 40.48, 38.66, 28.95.

Solvents and Celite Drying Methods for Following Procedures:

All syntheses were carried out in an N$_2$ purged dry box using standard air sensitive procedures. Celite (Sigma-Aldrich) and 3 Å molecular sieves (Sigma-Aldrich or Acros) were dried in a vacuum oven at 250° C. for 3 days. Solvents were purged with N2 and dried and stored over 3 Å molecular sieves. NMR solvents were dried and stored over 3 Å molecular sieves. MeMgI (3 M in Et$_2$O, Sigma-Aldrich), CH$_3$I (Sigma-Aldrich), isobutyl bromide (Sigma-Aldrich), 1,2,3,5-tetrahydro-s-indacene (GLSyntech) were used as received. Pentamethylcyclopentadienylhafnium trichloride (Me$_5$CpHfCl$_3$) was either purchased from Stem Chemicals or synthesized in a manner analogous to that described in *Journal of Organometallic Chemistry*, 1988, v. 340, pp. 37-40.

6,6-Dimethyl-1,5,6,7-tetrahydro-s-indacenyl Lithium

About 13.89 ml of 1.6 M solution of n-BuLi in hexane (22.2 mmol) was added drop wise to the solution of 2,2-dimethyl-1,2,3,5-tetrahydro-s-indacene (4.095 g; 22.2 mmol) in 60 ml of Et$_2$O, which was cooled to −35° C. The reaction mixture was allowed to stir at room temperature for two hours. After two hours, colorless solution turned into white slurry. Et$_2$O was removed under vacuum. The Lithium salt was filtered and washed with pentane (4×20 ml). The isolated white precipitate was dried under vacuum to give 4.001 (94.6%) of the product. $^1$H-NMR (ds-THF, ppm): δ 1.04 (s, 6H, CH$_3$), 2.58 (br, s, 4H, CH$_2$), 5.72 (d, J=3.4, 0.5 Hz, 1H, Cp_H), 6.32 (t, J=3.3 Hz, 1H, Cp_H), 7.02 (S, 2H, Ar_H).

1,6,6-Trimethyl-1,5,6,7-tetrahydro-s-indacenyl Lithium

MeI (0.19 g, 1.31 mmol) was added to 6,6-dimethyl-1,5,6,7-tetrahydro-s-indacenyl Lithium (0.21 g, 1.09 mmol) in THF (10 ml) and stirred for 16 hours. THF was then removed by a stream of nitrogen and the crude product was reslurried into pentane for 15 minutes. The solid was removed by filtration on Celite, and was washed with pentane. All solvents were then removed from the filtrate under vacuo and 2,2,5-trimethyl-1,2,3,5-tetrahydro-s-indacene was isolated as a clear oil (0.16 g, 0.8 mmol), which was dissolved into Et$_2$O (15 ml). nBuLi (0.074 ml, 11M) was then slowly added and the reagents were stirred for 30 minutes. Then all Et$_2$O was removed under vacuo and pentane was added and stirred for an additional 10 minutes prior to filtering off the product as a white solid (0.166 g, 100%), which was analyzed by $^1$H NMR (500 MHz, DMSO-d6) δ 6.77 (s, 2H), 6.04 (s, 1H), 5.39 (s, 1H), 2.59 (d, J=12.9 Hz, 4H), 2.29 (s, 3H), 1.09 (s, 6H).

Pentamethylcyclopentadienyl(1,6,6-trimethyl-1,5,6,7-tetrahydro-s-indacenyl)hafnium(IV) dimethyl (Cat ID=C)

Mix 1,6,6-trimethyl-1,5,6,7-tetrahydro-s-indacenyl Lithium (0.166 g, 0.8 mmol) with CpMe$_5$HfCl$_3$ (0.341 g, 0.8 mmol) in Et$_2$O (20 ml) and stir it overnight. All Et$_2$O was then removed by a stream of nitrogen and the crude product was reslurried into pentane for 15 minutes. The product was isolated by filtration as a mixture of LiCl and was used for the next step with no further purification. The crude Hafnium dichloride (0.36 g, 0.6 mmol) was slurried into toluene (15 ml) and MeMgI (0.38 ml, 3 M in Et2O) was then added and the reaction was stirred at 70° C. for 16 hours. The reaction was cooled to room temperature and 1, 4 dioxane was added. The mixture was stirred for 15 minutes and solids were removed by filtration on celite and was washed by Et$_2$O. All volatiles were then removed under vacuo. Final product (C$_{27}$H$_{38}$Hf) was isolated as a solid (0.29 g, 67%), which was analyzed by $^1$H NMR (CD$_2$C$_{12}$, 400 MHz): δ 7.32 (s, 1H), 6.93 (d, J=1.1 Hz, 1H), 5.25 (d, J=2.8 Hz, 2H), 2.76 (d, J=1.5 Hz, 2H), 2.72 (dd, J=4.7, 1.5 Hz, 2H), 2.18 (s, 3H), 1.87 (s, 15H), 1.15 (s, 3H), 1.13 (s, 3H), −1.07 (s, 3H), −2.05 (s Hz, 3H).

Synthesis of pentamethylcyclopentadienyl(1-methyl-1,5,6,7-tetrahydro-s-indacenyl)hafnium(IV) dimethyl (Cat ID=A)

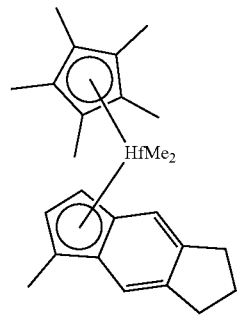

1-Methyl-1,5,6,7-tetrahydro-s-indacenyl Lithium 1,5,6,7-tetrahydro-s-indacenyl lithium was synthesized in a manner analogous to that described in U.S. Ser. No. 16/192,493, filed Nov. 15, 2018 (published as US 2019/0161560).

MeI (6.74 g, 47.5 mmol) was slowly added to 1,5,6,7-tetrahydro-s-indacenyl Lithium (7.0 g, 43.2 mmol) in Et$_2$O (100 ml) and THF (20 ml) and stirred for 4 hours. All solvents were then removed by a stream of nitrogen and the crude product was reslurried into pentane for 15 minutes. The solid was removed by filtration on Celite, and was washed with pentane. All solvents were then removed from the filtrate under vacuo and 1-methyl-1,5,6,7-tetrahydro-s-indacene was isolated as a clear oil (6.95 g, 41.0 mmol), which was then dissolved into Et$_2$O (100 ml). nBuLi (3.7 ml, 11M) was then slowly added and stirred for 1 hour. Then all Et$_2$O was removed under vacuo and pentane added and allowed to stir for additional 10 minutes, followed by filtration to collect the product as a white solid (6.97 g, 97%), which was analyzed by $^1$H NMR (500 MHz, DMSO-d6) δ 6.80 (d, J=1.0 Hz, 2H), 6.04 (d, J=3.2 Hz, 1H), 5.37 (d, J=3.9 Hz, 1H), 2.74 (dt, J=10.5, 7.0 Hz, 4H), 2.27 (s, 3H), 1.86 (p, J=7.1 Hz, 2H).

Pentamethylcyclopentadienyl(1-methyl-1,5,6,7-tetrahydro-s-indacenyl)hafnium(IV) dimethyl Mix 1-methyl (1,5,6,7-tetrahydro-s-indacenyl) Lithium (6.97 g, 40 mmol) with CpMe$_5$HfCl$_3$ (16.1 g, 40 mmol) in Et$_2$O (150 ml) and stir it for 3 hours. LiCl was removed by filtration. And all Et$_2$O was then removed by a stream of nitrogen and the crude product was reslurried into pentane for 15 minutes and was cooled under −35° C. The product was isolated by filtration as an off-white solid (15.47 g, 26 mmol), which was slurried into toluene (50 ml) and MeMgI (17.3 ml, 3 M in Et20) was then added and the reaction was stirred at 70° C. for 16 hours. The reaction was cooled to room temperature and 1, 4 dioxane was added. The mixture was stirred for 15 minutes and solids were removed by filtration on Celite and was washed by Et$_2$O. All volatiles were then removed under vacuo. Final product (C$_{25}$H$_{34}$Hf) was isolated as a solid (12.3 g, 60%), which was analyzed by $^1$H NMR (CD$_2$C$_{12}$, 400 MHz): δ 7.45-7.33 (m, 1H), 7.02-6.92 (m, 1H), 5.32 (dd, J=2.9, 0.9 Hz, 1H), 5.27 (dd, J=2.8, 0.6 Hz, 1H), 2.99-2.86 (m, 4H), 2.19 (s, 3H), 2.11-1.99 (m, 2H), 1.88 (s, 15H), −1.08 (s, 3H), −2.12 (s, 3H).

Synthesis of pentamethylcyclopentadienyl (1-isobutyl-1,5,6,7-tetrahydro-s-indacenyl) hafnium (IV) dimethyl (Cat ID=B)

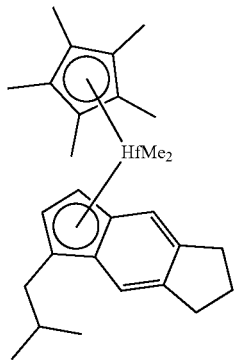

1-isoButyl-1,5,6,7-tetrahydro-s-indacenyl Lithium isoButyl bromide (1.69 g, 12 mmol) was added to 1,5,6,7-tetrahydro-s-indacenyl Lithium (2.0 g, 12 mmol) in THF (100 ml) and stirred for 16 hours. THF then removed by a stream of nitrogen and the crude product was reslurried into pentane for 15 minutes. The solid was removed by filtration on celite. And it is washed by pentane. All solvents were then removed from the filtrate under vacuo and 1-isobutyl-1,5,6,7-tetrahydro-s-indacene was isolated as a clear oil (2.54 g, 12 mmol), which is dissolved into $Et_2O$ (50 ml). nBuLi (1.1 ml, 11M) was then slowly added and stirred for 1 hour. Then all $Et_2O$ was removed under vacuo and pentane was added and stirred for an additional 10 minutes then filtered to collect the product as a white solid (2.5 g, 96%), which was analyzed by $^1H$ NMR (500 MHz, DMSO-d6) δ 6.82 (d, J=9.7 Hz, 2H), 6.06 (s, 1H), 5.39 (d, J=3.2 Hz, 1H), 2.73 (q, J=6.9 Hz, 4H), 2.50 (d, J=6.7 Hz, 2H), 1.86 (p, J=7.0 Hz, 2H), 1.70 (dt, J=13.2, 6.6 Hz, 1H), 0.83 (d, J=6.6 Hz, 6H).

Pentamethylcyclopentadienyl (1-isobutyl-1,5,6,7-tetrahydro-s-indacenyl) hafnium(IV) dimethyl 1-isoButyl-1,5,6,7-tetrahydro-s-indacenyl lithium (0.27 g, 1.2 mmol) was mixed with $CpMe_5HfCl_3$ (0.52 g, 1.2 mmol) in $Et_2O$ (20 ml) and stirred overnight. $Et_2O$ was then removed by a stream of nitrogen and the crude product was reslurried into pentane for 15 minutes. The mixture was cooled at −35° C. for 1 hour. The product was isolated by filtration as a mixture of LiCl and was used for the next step with no further purification. The crude hafnium dichloride (0.68 g, 1.1 mmol) was slurried into toluene (20 ml) and MeMgI (0.71 ml, 3 M in $Et_2O$) was then added and the reaction was stirred at 70° C. for 16 hours. The reaction was cooled to room temperature and 1,4-dioxane (0.38 ml) was added. The mixture was stirred for 15 minutes and solids were removed by filtration on Celite and washed by $Et_2O$. Volatiles were then removed from the filtrate under vacuo. The product slowly became a solid, to which was added 0.5 ml of pentane. This was swirled and cooled at −35° C. for 3 hours, and pentane was pipetted away. Final product ($C_{28}H_{40}Hf$) was isolated as a solid (0.4 g, 60%), which was analyzed by $^1H$ NMR ($CD_2C_{12}$, 400 MHz): δ 7.38 (s, 1H), 6.97 (d, J=1.4 Hz, 1H), 5.34 (dd, J=2.9, 0.8 Hz, 1H), 5.27 (d, J=2.9 Hz, 1H), 2.99-2.88 (m, 4H), 2.80 (dd, J=13.5, 5.8 Hz, 1H), 2.04 (p, J=7.3 Hz, 2H), 1.93-1.79 (m, 17H), 0.93 (d, J=6.5 Hz, 3H), 0.85 (d, J=6.4 Hz, 3H), −1.08 (s, 3H), −2.14 (s, 3H).

Polymerization Examples

Pre-catalysts used in the examples can be prepared as described above. Activator A-1 can be purchased from Boulder Chemical Company as 10 wt % solution in methylcyclohexane. Activator A-2 can be prepared as described in U.S. Ser. No. 16/394,166, filed Apr. 25, 2019. Activator A-3 can be purchased from W.R. Grace & Company or from Boulder Chemical Company.

| Pre-Catalyst | 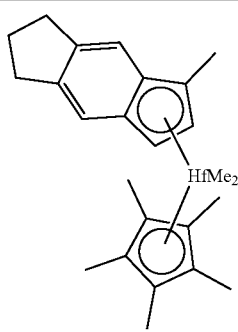 | 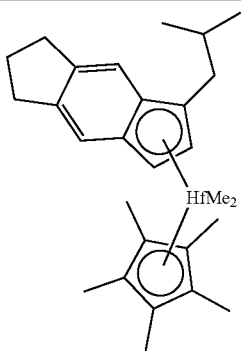 | 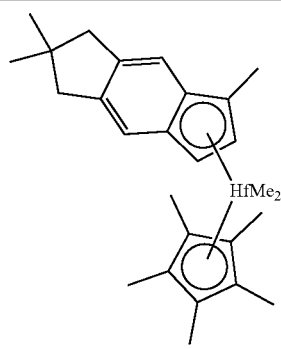 |
|---|---|---|---|
| Cat ID | A | B | C |
| Activator | 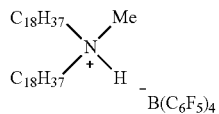 | 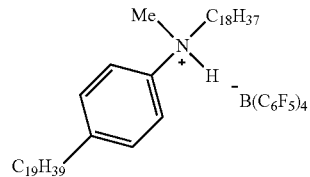 | 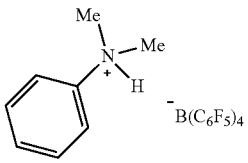 |
| Act ID | A-1 | A-2 | A-3 |

Solvents, polymerization grade toluene and/or isohexanes were supplied by ExxonMobil Chemical Company and were purified by passing through a series of columns: two 500 cc Oxyclear cylinders in series from Labclear (Oakland, Calif.), followed by two 500 cc columns in series packed with dried 3 Å molecular sieves (8-12 mesh; Aldrich Chemical Company), and two 500 cc columns in series packed with dried 5 Å molecular sieves (8-12 mesh; Aldrich Chemical Company).

1-decene monomer can be purchased from Sigma Aldrich and is purified by passing through a basic alumina column and dried over 3 Å molecular sieves before use. All complexes and the activators were added to the reactor as dilute solutions in the indicated solvent. The concentrations of the solutions of activator, scavenger, and complexes that were added to the reactor were chosen so that between 40-200 microliters of the solution were added to the reactor to ensure accurate delivery.

Reactor Description and Preparation. Polymerizations were conducted in an inert atmosphere ($N_2$) drybox using autoclaves equipped with an external heater for temperature control, glass inserts (internal volume of reactor=23.5 mL), septum inlets, regulated supply of nitrogen, and equipped with disposable polyether ether ketone mechanical stirrers (800 RPM). The autoclaves were prepared by purging with dry nitrogen at 110° C. or 115° C. for 5 hours and then at 25° C. for 5 hours.

Typical decene polymerizations: The reactor was prepared as described above. Solvent if used and 1-decene were added via syringe at room temperature and atmospheric pressure. The reactor was then brought to process temperature (60° C., 85° C., or 110° C.). Next, the stirrers where set to 800 RPM and the cells were pressurized to 80 psi with nitrogen. Scavenger solution (e.g., tri-n-octylaluminum, TNOA) was then added via syringe to the reactor at process conditions. Activator solution was added via syringe to the reactor at process conditions, followed by the pre-catalyst solution via syringe to the reactor at process conditions. Reactor temperature was monitored and typically maintained within +/−1° C. Polymerizations were halted by addition of approximately 50 psi $O_2$/Ar (5 mole % $O_2$) gas mixture to the autoclaves for approximately 30 seconds. The polymerizations were quenched after 60 minutes polymerization time. The reactors were cooled and vented. The final PAO was isolated after the solvent, unreacted monomers, and other volatiles were removed in-vacuo. Yields reported include total weight of the non-volatile PAO and residual catalyst. Catalyst activity is reported as grams of PAO per mmol transition metal compound per hour of reaction time (g/hr·mmol) and is based on the weight of the isolated PAO. This is a minimum catalyst activity as some dimeric PAO molecules can be lost in the drying process.

Characterization of isolated PAO

The unsaturated PAO product was analyzed (as follows) to determine the distributions of vinylidenes ("Vd"), di-substituted vinylenes ("Di"), tri-substituted vinylenes ("Tri-sub"), and vinyls ("Vi"), the catalyst activity level, and physical properties such as number average molecular weight. Conversion percentages of the reactions were calculated from the isolated yield of products and the amount of alpha-olefin used in the reaction. Specifically, conversion=grams isolated PAO/grams alpha-olefin used (when reported in %, conversion=(grams isolated PAO/grams alpha-olefin used)×100).

Proton NMR ($^1$H-NMR) was used to determine the number average molecular weight of the unsaturated PAO and the quantitative breakdown of the olefinic structure types (e.g., vinyl, vinylene, di-substituted vinylene, tri-substituted vinylene, and vinylidene).

Specifically, an NMR instrument of 400 or 500 MHz is run under the following conditions: a ~30° flip angle RF pulse, 128 scans, with a relaxation delay of ~5 seconds between pulses; sample (60-100 mg) dissolved in $CDCl_3$ (deuterated chloroform) in a 5 mm NMR tube; and signal collection temperature at ~25° C. The following approach is taken in determining the concentrations of the various olefins among all of the olefins from an NMR spectrum. First, peaks corresponding to different types of hydrogen atoms in vinyls (T1), vinylidenes (T2), di-substituted vinylenes (T3), and tri-substituted vinylenes (T4) are identified at the peak regions in TABLE C below. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations ($C_1$, $C_2$, $C_3$, and $C_4$, respectively, in mol %) of each type of olefin, on the basis of the total molar quantity of all of the olefins, is then calculated (in each case, Ci=100*Qi/Qt).

TABLE C

| Hydrogen Atoms | | Peak | | Number of | Quantity | Concentration |
|---|---|---|---|---|---|---|
| Type No. | Olefin Structure | Region (ppm) | Peak Area | Hydrogen Atoms | of Olefin (mol) | of Olefin (mol %) |
| T1 | $CH_2=CH-R^1$ | 4.95-5.10 | A1 | 2 | Q1 = A1/2 | C1 |
| T2 | $CH_2=CR^1R^2$ | 4.65-4.84 | A2 | 2 | Q2 = A2/2 | C2 |
| T3 | $CHR^1=CHR^2$ | 5.31-5.55 | A3 | 2 | Q3 = A3/2 | C3 |
| T4 | $CR^1R^2=CH\,R^3$ | 5.11-5.30 | A4 | 1 | Q4 = A4 | C4 |

The number average molecular weight was determined by:

Mn = {[Saturated + (vinylene + vinylidene + vinyl + trisubstituted × 2)]/(vinylene + vinylidene + vinyl + trisubstituted × 2)} × 14 ("Saturated", "vinylene", "vinyl", "trisubstituted" in this equation refer to peak area integration)

TABLE 1 below shows inventive Examples and Comparative Examples (*) listing reaction conditions including identity of the metallocene compound (Cat ID) and the activator (Act ID), the polymerization temperature, the yield of isolated PAO, the catalyst activity, together with Mn, as measured by $^1$H NMR, and the distributions of the olefins in terms of mole percentages of each type, on the basis of the total moles of the four categories of olefins as determined by $^1$H NMR. All inventive examples use non-aromatic hydrocarbon solvents, while the comparative examples require the use of toluene to solubilize the activator, A-3.

Standard reaction conditions using the PPR: 0.08 umol pre-catalyst, 0.088 umol activator, 0.60 umol TnOAl scavenger (10 mmol/L in isohexane), 2 ml decene (neat, 1.48 g), total of 3 ml solvent (isohexane (iHex) alone or isohexane with methylcyclohexane (MeCy), or isohexane with toluene (Tol)) used, 800 rpm stir rate, 60 minute reaction time. All pre-catalysts were dissolved in isohexane at 0.8 mmol/L. Activator A-2 was dissolved in isohexane at 0.8 mmol/L. Activator A-1 was supplied as a 10% solution in methylcyclohexane (72.4 mM) and was further diluted in isohexane to make a 0.8 mmol/L solution using isohexane. Activator A-3 is sparingly soluble in alkane solvents and was dissolved in toluene at 0.8 mmol/L as the control. Actual amounts of solvents used, reaction temperature, PAO yield, catalyst activity and PAO characterization are reported in Table 1, below.

distributions of the olefins in terms of mole percentages of each type, on the basis of the total moles of the four categories of olefins as determined by $^1$H NMR. Activator A-1 which is supplied as a 10% solution in methylcyclohexane was isolated as an oil by pulling off the solvent under vacuum. Residual solvent was not detectable by $^1$H NMR. The resulting oil was diluted in 1-decene to a concentration of 0.8 mmol/L. All examples further described in Table 2 are free of aromatic solvents, and are essentially free of non-alpha-olefin hydrocarbon solvents.

Standard reaction conditions using the PPR: 0.12 umol pre-catalyst (0.8 mmol/L in 1-decene), 0.158 umol activator (0.8 mmol/L in 1-decene), 0.60 umol TnOAl scavenger (10 mmol/L in 1-decene), 3 ml decene total added to the reactors

TABLE 1

| EX# | Cat ID | Act ID | iHex (uL) | Tol (uL) | MeCy (uL) | T (C.) | yield (g) | Activity (gP/mmol cat · hr) | % vinylene | % trisub | % vinyl | % vinylidene | Mn g/mol |
|---|---|---|---|---|---|---|---|---|---|---|---|---|---|
| 1 | A | A-1 | 2878 | 0 | 122 | 60 | 0.266 | 3,325 | 0.4 | 0.9 | 1.0 | 97.7 | 577 |
| 2 | A | A-1 | 2878 | 0 | 122 | 60 | 0.296 | 3,700 | 0.4 | 1.0 | 0.9 | 97.7 | 566 |
| 3 | A | A-1 | 2878 | 0 | 122 | 85 | 0.679 | 8,488 | 0.2 | 1.1 | 0.6 | 98.1 | 361 |
| 4 | A | A-1 | 2878 | 0 | 122 | 85 | 0.756 | 9,447 | 0.2 | 1.2 | 0.6 | 98.0 | 357 |
| 5 | A | A-1 | 2878 | 0 | 122 | 110 | 1.109 | 13,859 | 0.2 | 1.8 | 0.4 | 97.6 | 305 |
| 6 | A | A-1 | 2878 | 0 | 122 | 110 | 1.120 | 13,996 | 0.2 | 1.9 | 0.4 | 97.6 | 305 |
| 7 | A | A-2 | 3000 | 0 | 0 | 60 | 0.249 | 3,112 | 0.4 | 0.9 | 0.9 | 97.8 | 566 |
| 8 | A | A-2 | 3000 | 0 | 0 | 60 | 0.245 | 3,062 | 0.4 | 1.0 | 1.1 | 97.5 | 572 |
| 9 | A | A-2 | 3000 | 0 | 0 | 85 | 0.616 | 7,698 | 0.3 | 1.2 | 0.7 | 97.9 | 363 |
| 10 | A | A-2 | 3000 | 0 | 0 | 85 | 0.665 | 8,313 | 0.2 | 1.2 | 0.7 | 97.9 | 357 |
| 11 | A | A-2 | 3000 | 0 | 0 | 110 | 1.077 | 13,459 | 0.2 | 1.5 | 0.3 | 98.0 | 304 |
| 12 | A | A-2 | 3000 | 0 | 0 | 110 | 1.094 | 13,675 | 0.2 | 1.7 | 0.4 | 97.7 | 303 |
| 13* | A | A-3 | 2890 | 110 | 0 | 60 | 0.171 | 2,138 | 0.3 | 0.7 | 0.9 | 98.0 | 561 |
| 14* | A | A-3 | 2890 | 110 | 0 | 85 | 0.795 | 9,935 | 0.2 | 1.4 | 0.3 | 98.1 | 299 |
| 15* | A | A-3 | 2890 | 110 | 0 | 110 | 0.882 | 11,025 | 0.2 | 1.2 | 0.6 | 98.0 | 352 |
| 16 | B | A-1 | 2878 | 0 | 122 | 60 | 0.183 | 2,286 | 0.3 | 0.8 | 1.0 | 97.9 | 541 |
| 17 | B | A-1 | 2878 | 0 | 122 | 60 | 0.197 | 2,462 | 0.4 | 1.0 | 1.1 | 97.5 | 540 |
| 18 | B | A-1 | 2878 | 0 | 122 | 85 | 0.510 | 6,375 | 0.2 | 1.3 | 0.8 | 97.7 | 349 |
| 19 | B | A-1 | 2878 | 0 | 122 | 85 | 0.566 | 7,075 | 0.2 | 1.1 | 0.7 | 98.0 | 350 |
| 20 | B | A-1 | 2878 | 0 | 122 | 110 | 1.039 | 12,988 | 0.2 | 1.4 | 0.4 | 98.0 | 302 |
| 21 | B | A-1 | 2878 | 0 | 122 | 110 | 1.034 | 12,921 | 0.2 | 1.5 | 0.4 | 97.9 | 300 |
| 22 | B | A-2 | 3000 | 0 | 0 | 60 | 0.147 | 1,837 | 0.3 | 0.8 | 1.0 | 97.8 | 541 |
| 23 | B | A-2 | 3000 | 0 | 0 | 60 | 0.137 | 1,713 | 0.4 | 0.8 | 1.1 | 97.7 | 562 |
| 24 | B | A-2 | 3000 | 0 | 0 | 85 | 0.417 | 5,211 | 0.2 | 1.0 | 0.8 | 98.0 | 360 |
| 25 | B | A-2 | 3000 | 0 | 0 | 85 | 0.427 | 5,336 | 0.2 | 1.0 | 0.7 | 98.1 | 353 |
| 26 | B | A-2 | 3000 | 0 | 0 | 110 | 0.894 | 11,172 | 0.2 | 1.6 | 0.5 | 97.8 | 303 |
| 27 | B | A-2 | 3000 | 0 | 0 | 110 | 0.934 | 11,672 | 0.1 | 1.4 | 0.4 | 98.0 | 303 |
| 28* | B | A-3 | 2890 | 110 | 0 | 60 | 0.214 | 2,674 | 0.3 | 0.8 | 1.1 | 97.8 | 529 |
| 29* | B | A-3 | 2890 | 110 | 0 | 85 | 0.557 | 6,963 | 0.2 | 1.6 | 0.3 | 97.9 | 301 |
| 30* | B | A-3 | 2890 | 110 | 0 | 110 | 1.027 | 12,834 | 0.2 | 1.2 | 0.7 | 97.9 | 346 |
| 31 | C | A-1 | 2878 | 0 | 122 | 60 | 0.296 | 3,653 | 0.3 | 0.7 | 0.8 | 98.3 | 508 |
| 32 | C | A-1 | 2878 | 0 | 122 | 60 | 0.318 | 3,925 | 0.3 | 0.7 | 0.8 | 98.3 | 503 |
| 33 | C | A-1 | 2878 | 0 | 122 | 85 | 0.810 | 9,997 | 0.2 | 1.1 | 0.5 | 98.1 | 338 |
| 34 | C | A-1 | 2878 | 0 | 122 | 85 | 0.828 | 10,222 | 0.2 | 1.2 | 0.5 | 98.1 | 339 |
| 35 | C | A-1 | 2878 | 0 | 122 | 110 | 1.117 | 13,782 | 0.2 | 1.6 | 0.3 | 98.0 | 301 |
| 36 | C | A-1 | 2878 | 0 | 122 | 110 | 1.175 | 14,502 | 0.2 | 1.8 | 0.4 | 97.6 | 300 |
| 37 | C | A-2 | 3000 | 0 | 0 | 60 | 0.260 | 3,210 | 0.3 | 0.6 | 0.8 | 98.3 | 499 |
| 38 | C | A-2 | 3000 | 0 | 0 | 60 | 0.274 | 3,383 | 0.3 | 0.9 | 0.8 | 97.9 | 499 |
| 39 | C | A-2 | 3000 | 0 | 0 | 85 | 0.508 | 6,270 | 0.2 | 1.0 | 0.5 | 98.3 | 344 |
| 40 | C | A-2 | 3000 | 0 | 0 | 85 | 0.741 | 9,146 | 0.2 | 1.1 | 0.5 | 98.2 | 342 |
| 41 | C | A-2 | 3000 | 0 | 0 | 110 | 1.105 | 13,642 | 0.1 | 1.3 | 0.2 | 98.3 | 302 |
| 42 | C | A-2 | 3000 | 0 | 0 | 110 | 1.110 | 13,700 | 0.2 | 1.5 | 0.3 | 98.0 | 299 |
| 43* | C | A-3 | 2890 | 110 | 0 | 60 | 0.307 | 3,789 | 0.3 | 0.7 | 0.8 | 98.2 | 494 |
| 44* | C | A-3 | 2890 | 110 | 0 | 60 | 0.320 | 3,951 | 0.3 | 0.9 | 0.8 | 98.0 | 492 |
| 45* | C | A-3 | 2890 | 110 | 0 | 85 | 0.830 | 10,241 | 0.2 | 1.1 | 0.5 | 98.2 | 336 |
| 46* | C | A-3 | 2890 | 110 | 0 | 85 | 0.817 | 10,084 | 0.2 | 1.1 | 0.5 | 98.2 | 338 |
| 47* | C | A-3 | 2890 | 110 | 0 | 110 | 0.905 | 11,173 | 0.1 | 1.4 | 0.2 | 98.2 | 298 |
| 48* | C | A-3 | 2890 | 110 | 0 | 110 | 1.087 | 13,412 | 0.2 | 1.4 | 0.3 | 98.1 | 300 |

*Comparative examples using the standard activator, A-3, and toluene as the activator diluent.

TABLE 2 below shows inventive Examples listing reaction conditions including identity of the metallocene compound (Cat ID) and the activator (Act ID), the polymerization temperature, the yield of isolated PAO, the catalyst activity, together with Mn, as measured by $^1$H NMR, and the including amounts used for diluting catalyst, activator and scavenger (2.22 g total), 800 rpm stir rate, 60 minute reaction time. Reaction temperature, PAO yield, catalyst activity and PAO characterization are reported in Table 2, below.

TABLE 2

| EX# | Cat ID | Act ID | T (C.) | yield (g) | Activity (gP/ mmol cat · hr) | % vinylene | % trisub | % vinyl | % vinylidene | Mn g/mol |
|---|---|---|---|---|---|---|---|---|---|---|
| 49 | A | A-1 | 60 | 0.507 | 4,220 | | | | | |
| 50 | A | A-1 | 60 | 0.572 | 4,759 | 0.8 | 0.9 | 1.0 | 97.3 | 932 |
| 51 | A | A-1 | 60 | 0.554 | 4,616 | | | | | |
| 52 | A | A-1 | 85 | 1.203 | 10,025 | | | | | |
| 53 | A | A-1 | 85 | 1.268 | 10,565 | 0.4 | 1.2 | 0.9 | 97.5 | 470 |
| 54 | A | A-1 | 85 | 1.329 | 11,067 | | | | | |
| 55 | A | A-1 | 110 | 1.882 | 15,669 | | | | | |
| 56 | A | A-1 | 110 | 1.907 | 15,892 | 0.4 | 2.1 | 0.3 | 97.1 | 349 |
| 57 | A | A-1 | 110 | 1.850 | 15,414 | | | | | |
| 58 | A | A-2 | 60 | 0.389 | 3,237 | | | | | |
| 59 | A | A-2 | 60 | 0.435 | 3,621 | 0.7 | 0.8 | 1.0 | 97.4 | 919 |
| 60 | A | A-2 | 60 | 0.416 | 3,466 | | | | | |
| 61 | A | A-2 | 85 | 1.064 | 8,862 | | | | | |
| 62 | A | A-2 | 85 | 1.093 | 9,107 | 0.4 | 1.1 | 1.0 | 97.5 | 479 |
| 63 | A | A-2 | 85 | 1.071 | 8,923 | | | | | |
| 64 | A | A-2 | 110 | 1.809 | 15,073 | | | | | |
| 65 | A | A-2 | 110 | 1.802 | 15,016 | 0.3 | 1.7 | 0.4 | 97.7 | 337 |
| 66 | A | A-2 | 110 | 1.817 | 15,141 | | | | | |
| 67 | B | A-1 | 60 | 0.666 | 5,548 | | | | | |
| 68 | B | A-1 | 60 | 0.654 | 5,448 | 0.7 | 0.8 | 0.8 | 97.7 | 815 |
| 69 | B | A-1 | 60 | 0.671 | 5,586 | | | | | |
| 70 | B | A-1 | 85 | 1.531 | 12,753 | | | | | |
| 71 | B | A-1 | 85 | 1.498 | 12,478 | 0.4 | 1.1 | 0.6 | 97.8 | 451 |
| 72 | B | A-1 | 85 | 1.547 | 12,888 | | | | | |
| 73 | B | A-1 | 110 | 1.883 | 15,687 | | | | | |
| 74 | B | A-1 | 110 | 1.906 | 15,881 | 0.4 | 2.3 | 0.2 | 97.1 | 335 |
| 75 | B | A-1 | 110 | 1.913 | 15,941 | | | | | |
| 76 | B | A-2 | 60 | 0.440 | 3,667 | | | | | |
| 77 | B | A-2 | 60 | 0.485 | 4,039 | 0.7 | 0.8 | 0.9 | 97.7 | 849 |
| 78 | B | A-2 | 60 | 0.481 | 4,003 | | | | | |
| 79 | B | A-2 | 85 | 1.278 | 10,643 | | | | | |
| 80 | B | A-2 | 85 | 1.318 | 10,973 | 0.4 | 1.0 | 0.7 | 97.9 | 454 |
| 81 | B | A-2 | 85 | 1.271 | 10,585 | | | | | |
| 82 | B | A-2 | 110 | 1.599 | 13,328 | | | | | |
| 83 | B | A-2 | 110 | 1.823 | 15,186 | 0.4 | 1.9 | 0.4 | 97.3 | 339 |
| 84 | B | A-2 | 110 | 1.735 | 14,452 | | | | | |
| 85 | C | A-1 | 60 | 0.693 | 5,777 | | | | | |
| 86 | C | A-1 | 60 | 0.779 | 6,490 | 0.8 | 0.9 | 1.1 | 97.2 | 986 |
| 87 | C | A-1 | 85 | 1.609 | 13,401 | | | | | |
| 88 | C | A-1 | 85 | 1.576 | 13,133 | 0.4 | 1.2 | 0.7 | 97.6 | 475 |
| 89 | C | A-1 | 110 | 1.881 | 15,677 | | | | | |
| 90 | C | A-1 | 110 | 1.923 | 16,023 | 0.4 | 2.5 | 0.2 | 96.8 | 345 |
| 91 | C | A-2 | 60 | 0.469 | 3,909 | | | | | |
| 92 | C | A-2 | 60 | 0.620 | 5,168 | 1.0 | 1.1 | 1.2 | 96.7 | 1013 |
| 93 | C | A-2 | 85 | 1.378 | 11,479 | | | | | |
| 94 | C | A-2 | 85 | 1.408 | 11,728 | 0.5 | 1.1 | 0.8 | 97.6 | 486 |
| 95 | C | A-2 | 110 | 1.723 | 14,354 | | | | | |
| 96 | C | A-2 | 110 | 1.833 | 15,271 | 0.4 | 1.8 | 0.3 | 97.5 | 344 |

Polymerization example 97. Batch polymerization reactions were conducted in a 1 L autoclave reactor equipped with paddle stirrer, an external water jacket for temperature control, a regulated supply of dry nitrogen, ethylene, propylene, and isohexane and an inlet for the introduction of other solvents, comonomers, pre-catalysts and activators. The reactor was dried by heating the reactor at 110-120° C. under a flow of dry nitrogen for about 1 hour prior to use. 200 ml of dried 1-decene and 100 uL of tri-n-octyl aluminum under nitrogen was cannulated into the reactor. Stirring was started (400 rpm) and the reactor was then heated to 110° C. Activator A-1 (67.3 mg) was dissolved in 10 ml of 1-decene in an activator addition tube which was attached to the reactor. A second addition tube containing 10 ml of 1-decene was attached to the activator addition tube (chaser), and high pressure nitrogen was attached to the end. High pressure nitrogen was then used to push the activator and chaser into the reactor. Catalyst A (25.8 mg) was dissolved in 10 ml of 1-decene in a catalyst addition tube which was attached to the reactor. A second addition tube containing 10 ml of 1-decene was attached to the catalyst addition tube (chaser), and high pressure nitrogen was attached to the end. High pressure nitrogen was then used to push the catalyst and chaser into the reactor. Timing started at the addition of Catalyst A to the reactor and was allowed to proceed for 1 hour. After this time period, heating and stirring were ceased, pressure was vented from the reactor and the reactor was opened and lowered exposing the contents to air. A total of 171 g of oligomer was isolated after blowing nitrogen over the liquid overnight to remove any unreacted 1-decene. Additional information can be found in Table 3, below.

TABLE 3

| EX# | Cat ID | Act ID | T (C.) | yield (g) | % conversion | Activity (gP/ mmol cat · hr) | % vinylene | % trisub | % vinyl | % vinylidene | Mn g/mol |
|---|---|---|---|---|---|---|---|---|---|---|---|
| 97 | A | A-1 | 110 | 171 | 96 | 3,400 | 0.6 | 4.4 | 0.2 | 94.8 | 312 |

All documents described herein are incorporated by reference herein for purposes of all jurisdictions where such practice is allowed, including any priority documents, related applications, and/or testing procedures to the extent they are not inconsistent with this text, provided however that any priority document not named in the initially filed application or filing documents is not incorporated by reference herein. As should be apparent from the foregoing general description and the specific embodiments, while forms of the invention have been illustrated and described, various modifications can be made without departing from the spirit and scope of the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention. Accordingly, it is not intended that the invention be limited thereby. Likewise, the term "comprising" is considered synonymous with the terms "including" and "containing." Also, whenever a composition, an element, or a group of elements is preceded with the transitional phrase "comprising," it should be understood that the same composition or group of elements is contemplated with transitional phrases "consisting essentially of," "consisting of," "selected from the group of consisting of," or "is" preceding the recitation of the composition, element, or elements, and vice versa.

What is claimed is the following:

1. A process for producing a poly alpha-olefin, PAO, the process comprising:

contacting a feed comprising a $C_6$-$C_{32}$ alpha-olefin with a catalyst system comprising an unsymmetrical metallocene compound, a non-aromatic hydrocarbon soluble activator compound, and a non-aromatic hydrocarbon solvent in a polymerization reactor under polymerization conditions to effect a polymerization reaction to obtain a polymerization reaction mixture comprising vinylidenes, tri-substituted vinylenes, optional di-substituted vinylenes, and optional vinyls; and obtaining an unsaturated PAO product from the polymerization reaction mixture, wherein the unsaturated PAO product comprises vinylidenes, optional tri-substituted vinylenes, optional di-substituted vinylenes, and optional vinyls.

2. The process of claim 1, wherein the metallocene compound is represented by Formula (I):

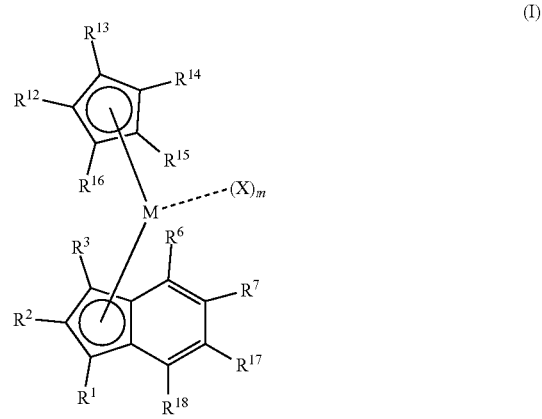

(I)

wherein:

$R^2$ is hydrogen and one of $R^1$ and $R^3$ is a substituted or unsubstituted linear, branched, or cyclic $C_1$-$C_6$ hydrocarbyl group, and the other of $R^1$ and $R^3$ is a hydrogen;

$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annulated to the indenyl ring;

$R^{12}$, $R^{13}$, $R^{14}$, and $R^{15}$, are each independently a substituted or unsubstituted linear, branched, or cyclic $C_1$-$C_{20}$ hydrocarbyl group;

$R^{16}$ is a substituted or unsubstituted linear, branched, or cyclic $C_1$-$C_{20}$ hydrocarbyl group or silylcarbyl group;

each X is independently a halide, a hydride, an amide, an alkoxide, a sulfide, a $C_1$-$C_{20}$ substituted or unsubstituted linear, branched, or cyclic hydrocarbyl group, or two or more X moieties together form a fused ring or ring system;

M is a transition metal, having an integer coordination number of v; and m is an integer equal to v-2, such as 1, 2, or 3.

3. The process of claim 1, wherein the metallocene compound is represented by Formula (II):

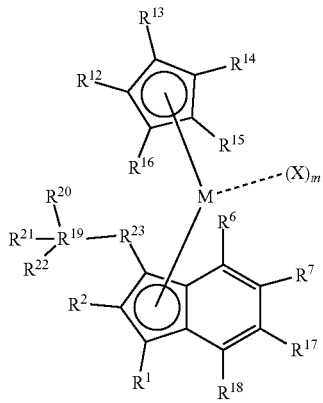

wherein:
$R^1$ and $R^2$ are hydrogen;
$R^{23}$ and $R^{19}$ comprise Group 14 atoms;
$R^{20}$, $R^{21}$, and $R^{22}$—are independently hydrogen or a substituted or unsubstituted linear, branched, or cyclic $C_1$-$C_{20}$ hydrocarbyl group and at least two of $R^{20}$, $R^{21}$, and $R^{22}$ are not hydrogen;
$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annulated to the indenyl ring;
$R^{12}$, $R^{13}$, $R^{14}$, $R^{15}$, and $R^{16}$ are each independently a substituted or unsubstituted linear, branched, or cyclic $C_1$-$C_8$ hydrocarbyl group;
each X is independently a halide, a hydride, an amide, an alkoxide, a sulfide, or a $C_1$-$C_{20}$ substituted or unsubstituted linear, branched, or cyclic hydrocarbyl group, or two or more X moieties together form a fused ring or ring system;
M is a group 3, 4, or 5 transition metal having an integer coordination number of v;
and m is an integer equal to v-2.

4. The process of claim 1, wherein the metallocene compound is represented by Formula (III):

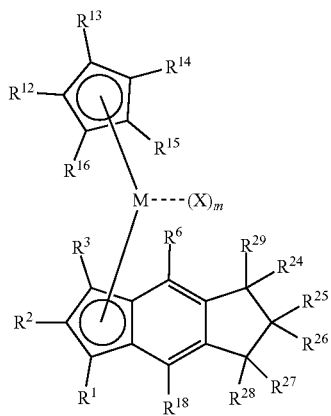

wherein $R^2$ is hydrogen and one of $R^1$ and $R^3$ is a substituted or unsubstituted linear, branched, or cyclic $C_1$-$C_6$ hydrocarbyl group, and the other of $R^1$ and $R^3$ of $R^1$ and $R^3$ is a hydrogen;
$R^6$, $R^{18}$, $R^{29}$, $R^{24}$, $R^{25}$, $R^{26}$, $R^{27}$ and $R^{28}$ are each independently hydrogen, a substituted or unsubstituted linear, branched, or cyclic $C_1$-$C_{30}$ hydrocarbyl group, or two of $R^6$, $R^{18}$, $R^{29}$, $R^{24}$, $R^{25}$, $R^{26}$, $R^{27}$ and $R^{28}$ taken together with the carbon atoms in the cyclopentan-indenyl ring to which they are directly connected, collectively form one or more substituted or unsubstituted rings annulated to the cyclopentan-indenyl ring;
$R^{12}$, $R^{13}$, $R^{14}$, $R^{15}$, and $R^{16}$ are each independently a substituted or unsubstituted linear, branched, or cyclic $C_1$-$C_{20}$ hydrocarbyl group;
each X is independently a halide, a hydride, an amide, an alkoxide, a sulfide, a $C_1$-$C_{20}$ substituted or unsubstituted linear, branched, or cyclic hydrocarbyl group, or two or more X moieties together form a fused ring or ring system;
M is a group 3, 4, or 5 transition metal having an integer coordination number of v;
and m is an integer equal to v-2.

5. The process of claim 1, wherein the metallocene compound is represented by Formula (IV):

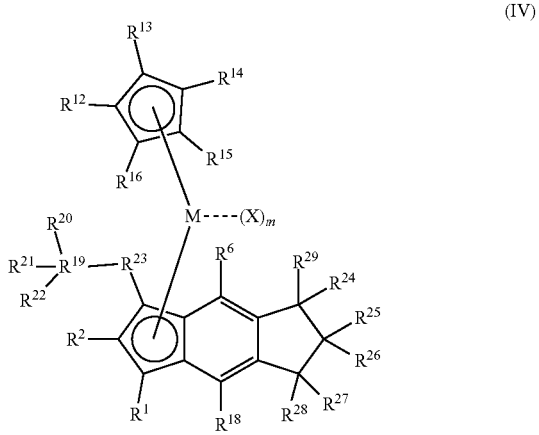

wherein:
$R^1$ and $R^2$ are hydrogen;
$R^{23}$ and $R^{19}$ comprise Group 14 atoms;
$R^{20}$, $R^{21}$, and $R^{22}$ are independently hydrogen or a substituted or unsubstituted linear, branched, or cyclic $C_1$-$C_{20}$ hydrocarbyl group and at least two of $R^{20}$, $R^{21}$, and $R^{22}$ are not hydrogen;
$R^6$, $R^{18}$, $R^{29}$, $R^{24}$, $R^{25}$, $R^{26}$, $R^{27}$ and $R^{28}$ are each independently hydrogen, a substituted or unsubstituted linear, branched, or cyclic $C_1$-$C_{30}$ hydrocarbyl group, or two of $R^6$, $R^{18}$, $R^{29}$, $R^{24}$, $R^{25}$, $R^{26}$, $R^{27}$ and $R^{28}$ taken together with the carbon atoms in the cyclopentan-indenyl ring to which they are directly connected, collectively form one or more substituted or unsubstituted rings annulated to the cyclopentan-indenyl ring;
$R^{12}$, $R^{13}$, $R^{14}$, $R^{15}$, and $R^{16}$ are each independently a substituted or unsubstituted linear, branched, or cyclic $C_1$-$C_{20}$ hydrocarbyl group;
each X is independently a halide, a hydride, an amide, an alkoxide, a sulfide, a $C_1$-$C_{20}$ substituted or unsubstituted linear, branched, or cyclic hydrocarbyl group, or two or more X moieties together form a fused ring or ring system;

M is a group 3, 4, or 5 transition metal having an integer coordination number of v;

and m is an integer equal to v-2.

6. The process of claim 1 wherein the metallocene is selected from pentamethylcyclopentadienyl (1-methyl-1,5,6,7-tetrahydro-s-indacenyl) hafnium dimethyl, pentamethylcyclopentadienyl (1-ethyl-1,5,6,7-tetrahydro-s-indacenyl) hafnium dimethyl, pentamethylcyclopentadienyl (1-n-propyl-1,5,6,7-tetrahydro-s-indacenyl) hafnium dimethyl, pentamethylcyclopentadienyl (1-isopropyl-1,5,6,7-tetrahydro-s-indacenyl) hafnium dimethyl, pentamethylcyclopentadienyl (1-n-butyl-1,5,6,7-tetrahydro-s-indacenyl) hafnium dimethyl, pentamethylcyclopentadienyl (1-isobutyl-1,5,6,7-tetrahydro-s-indacenyl) hafnium dimethyl, pentamethylcyclopentadienyl (1-sec-butyl-1,5,6,7-tetrahydro-s-indacenyl) hafnium dimethyl, pentamethylcyclopentadienyl (1-tert-butyl-1,5,6,7-tetrahydro-s-indacenyl) hafnium dimethyl pentamethylcyclopentadienyl (1-pentyl-1,5,6,7-tetrahydro-s-indacenyl) hafnium dimethyl, pentamethylcyclopentadienyl (1-neopentyl-1,5,6,7-tetrahydro-s-indacenyl) hafnium dimethyl, pentamethylcyclopentadienyl (1-n-hexyl-1,5,6,7-tetrahydro-s-indacenyl) hafnium dimethyl, pentamethylcyclopentadienyl (1-n-heptyl-1,5,6,7-tetrahydro-s-indacenyl) hafnium dimethyl, pentamethylcyclopentadienyl (1-n-octyl-1,5,6,7-tetrahydro-s-indacenyl) hafnium dimethyl, pentamethylcyclopentadienyl (1-benzyl-1,5,6,7-tetrahydro-s-indacenyl) hafnium dimethyl, pentamethylcyclopentadienyl (1-phenethyl-1,5,6,7-tetrahydro-s-indacenyl) hafnium dimethyl, pentamethylcyclopentadienyl (1-(2-phenylpropyl)-1,5,6,7-tetrahydro-s-indacenyl) hafnium dimethyl, pentamethylcyclopentadienyl (1,6,6-trimethyl-1,5,6,7-tetrahydro-s-indacenyl) hafnium dimethyl, pentamethylcyclopentadienyl (1-ethyl-6,6-dimethyl-1,5,6,7-tetrahydro-s-indacenyl) hafnium dimethyl, pentamethylcyclopentadienyl (1-n-propyl-6,6-dimethyl-1,5,6,7-tetrahydro-s-indacenyl) hafnium dimethyl, pentamethylcyclopentadienyl (1-isopropyl-6,6-dimethyl-1,5,6,7-tetrahydro-s-indacenyl) hafnium dimethyl, pentamethylcyclopentadienyl (1-n-butyl-6,6-dimethyl-1,5,6,7-tetrahydro-s-indacenyl) hafnium dimethyl, pentamethylcyclopentadienyl (1-isobutyl-6,6-dimethyl-1,5,6,7-tetrahydro-s-indacenyl) hafnium dimethyl, pentamethylcyclopentadienyl (1-sec-butyl-6,6-dimethyl-1,5,6,7-tetrahydro-s-indacenyl) hafnium dimethyl, pentamethylcyclopentadienyl (1-tert-butyl-6,6-dimethyl-1,5,6,7-tetrahydro-s-indacenyl) hafnium dimethyl pentamethylcyclopentadienyl (1-pentyl-6,6-dimethyl-1,5,6,7-tetrahydro-s-indacenyl) hafnium dimethyl, pentamethylcyclopentadienyl (1-neopentyl-6,6-dimethyl-1,5,6,7-tetrahydro-s-indacenyl) hafnium dimethyl, pentamethylcyclopentadienyl (1-n-hexyl-6,6-dimethyl-1,5,6,7-tetrahydro-s-indacenyl) hafnium dimethyl, pentamethylcyclopentadienyl (1-n-heptyl-6,6-dimethyl-1,5,6,7-tetrahydro-s-indacenyl) hafnium dimethyl, pentamethylcyclopentadienyl (1-n-octyl-6,6-dimethyl-1,5,6,7-tetrahydro-s-indacenyl) hafnium dimethyl, pentamethylcyclopentadienyl (1-benzyl-6,6-dimethyl-1,5,6,7-tetrahydro-s-indacenyl) hafnium dimethyl, pentamethylcyclopentadienyl (1-phenethyl-6,6-dimethyl-1,5,6,7-tetrahydro-s-indacenyl) hafnium dimethyl, pentamethylcyclopentadienyl (1-(2-phenylpropyl)-6,6-dimethyl-1,5,6,7-tetrahydro-s-indacenyl) hafnium dimethyl, pentamethylcyclopentadienyl (1-methyl-6,6-diethyl-1,5,6,7-tetrahydro-s-indacenyl) hafnium dimethyl, pentamethylcyclopentadienyl (1,6,6-triethyl-1,5,6,7-tetrahydro-s-indacenyl) hafnium dimethyl, pentamethylcyclopentadienyl (1-n-propyl-6,6-diethyl-1,5,6,7-tetrahydro-s-indacenyl) hafnium dimethyl, pentamethylcyclopentadienyl (1-isopropyl-6,6-diethyl-1,5,6,7-tetrahydro-s-indacenyl) hafnium dimethyl, pentamethylcyclopentadienyl (1-n-butyl-6,6-diethyl-1,5,6,7-tetrahydro-s-indacenyl) hafnium dimethyl, pentamethylcyclopentadienyl (1-isobutyl-6,6-diethyl-1,5,6,7-tetrahydro-s-indacenyl) hafnium dimethyl, pentamethylcyclopentadienyl (1-sec-butyl-6,6-diethyl-1,5,6,7-tetrahydro-s-indacenyl) hafnium dimethyl, pentamethylcyclopentadienyl (1-tert-butyl-6,6-diethyl-1,5,6,7-tetrahydro-s-indacenyl) hafnium dimethyl pentamethylcyclopentadienyl (1-pentyl-6,6-diethyl-1,5,6,7-tetrahydro-s-indacenyl) hafnium dimethyl, pentamethylcyclopentadienyl (1-neopentyl-6,6-diethyl-1,5,6,7-tetrahydro-s-indacenyl) hafnium dimethyl, pentamethylcyclopentadienyl (1-benzyl-6,6-diethyl-1,5,6,7-tetrahydro-s-indacenyl) hafnium dimethyl, pentamethylcyclopentadienyl (1-phenethyl-6,6-diethyl-1,5,6,7-tetrahydro-s-indacenyl) hafnium dimethyl, pentamethylcyclopentadienyl (1-(2-phenylpropyl)-6,6-diethyl-1,5,6,7-tetrahydro-s-indacenyl) hafnium dimethyl, pentamethylcyclopentadienyl (1-methylindenyl) hafnium dimethyl, pentamethylcyclopentadienyl (1-ethylindenyl) hafnium dimethyl, pentamethylcyclopentadienyl (1-n-propylindenyl) hafnium dimethyl, pentamethylcyclopentadienyl (1-isopropylindenyl) hafnium dimethyl, pentamethylcyclopentadienyl (1-n-butylindenyl) hafnium dimethyl, pentamethylcyclopentadienyl (1-isobutylindenyl) hafnium dimethyl, pentamethylcyclopentadienyl (1-sec-butylindenyl) hafnium dimethyl, pentamethylcyclopentadienyl (1-tert-butylindenyl) hafnium dimethyl pentamethylcyclopentadienyl (1-pentylindenyl) hafnium dimethyl, pentamethylcyclopentadienyl (1-neopentylindenyl) hafnium dimethyl, pentamethylcyclopentadienyl (1-n-hexylindenyl) hafnium dimethyl, pentamethylcyclopentadienyl (1-n-heptylindenyl) hafnium dimethyl, pentamethylcyclopentadienyl (1-n-octylindenyl) hafnium dimethyl, pentamethylcyclopentadienyl (1-benzylindenyl) hafnium dimethyl, pentamethylcyclopentadienyl (1-phenethylindenyl) hafnium dimethyl, pentamethylcyclopentadienyl (1-(2-phenylpropyl) indenyl) hafnium dimethyl, pentamethylcyclopentadienyl (1-methyl-3,6,7,8-tetrahydro-as-indacenyl) hafnium dimethyl, pentamethylcyclopentadienyl (1-ethyl-3,6,7,8-tetrahydro-as-indacenyl) hafnium dimethyl, pentamethylcyclopentadienyl (1-n-propyl-3,6,7,8-tetrahydro-as-indacenyl) hafnium dimethyl, pentamethylcyclopentadienyl (1-isopropyl-3,6,7,8-tetrahydro-as-indacenyl) hafnium dimethyl, pentamethylcyclopentadienyl (1-n-butyl-3,6,7,8-tetrahydro-as-indacenyl) hafnium dimethyl, pentamethylcyclopentadienyl (1-isobutyl-3,6,7,8-tetrahydro-as-indacenyl) hafnium dimethyl, pentamethylcyclopentadienyl (1-sec-butyl-3,6,7,8-tetrahydro-as-indacenyl) hafnium dimethyl, pentamethylcyclopentadienyl (1-tert-butyl-3,6,7,8-tetrahydro-as-indacenyl) hafnium dimethyl pentamethylcyclopentadienyl (1-pentyl-3,6,7,8-tetrahydro-as-indacenyl) hafnium dimethyl, pentamethylcyclopentadienyl (1-neopentyl-3,6,7,8-tetrahydro-as-indacenyl) hafnium dimethyl, pentamethylcyclopentadienyl (1-benzyl-3,6,7,8-tetrahydro-as-indacenyl) hafnium dimethyl, pentamethylcyclopentadienyl (1-phenethyl-3,6,7,8-tetrahydro-as-indacenyl) hafnium dimethyl, pentamethylcyclopentadienyl (1-(2-phenylpropyl)-3,6,7,8-tetrahydro-as-indacenyl) hafnium dimethyl, pentamethylcyclopentadienyl (1-methyl-benz [f]indenyl) hafnium dimethyl, pentamethylcyclopentadienyl (1-ethyl-benz [f]indenyl) hafnium dimethyl, pentamethylcyclopentadienyl (1-n-propyl-benz [f]indenyl) hafnium dimethyl, pentamethylcyclopentadienyl (1-isopropyl-benz [f]indenyl) hafnium dimethyl, pentamethylcyclopentadienyl (1-n-butyl-benz [f]indenyl) hafnium dimethyl, pentamethylcyclopentadienyl (1-isobutyl-benz [f]indenyl) hafnium dimethyl, pentamethylcyclopentadienyl (1-sec-butyl-benz [f]indenyl) hafnium dimethyl, pentamethylcyclopentadienyl (1-tert-butyl-benz [f]indenyl) hafnium dimethyl pentamethylcyclopentadienyl (1-pentyl-benz [f]indenyl) hafnium dimethyl, pentamethylcyclopentadienyl (1-neopentyl-benz [f]indenyl) hafnium dimethyl, pentamethylcyclopentadienyl (1-benzyl-benz [f]indenyl) hafnium dimethyl, pentamethylcyclopentadienyl (1-phenethyl-benz [f]indenyl) hafnium dimethyl, pentamethylcyclopentadienyl (1-(2-phenylpropyl)-benz [f]indenyl) hafnium dimethyl, pentamethylcyclopentadienyl (1-methyl-benz [e]indenyl) hafnium dimethyl, pentamethylcyclopentadienyl (1-ethyl-benz [e]indenyl) hafnium dimethyl, pentamethylcyclopentadienyl (1-n-propyl-benz [e]indenyl) hafnium dimethyl, pentamethylcyclopentadienyl (1-isopropyl-benz [e]indenyl) hafnium dimethyl, pentamethylcyclopentadienyl (1-n-butyl-benz [e]indenyl) hafnium dimethyl, pentamethylcyclopentadienyl (1-isobutyl-benz [e]indenyl) hafnium dimethyl, pentamethylcyclopentadienyl (1-sec-butyl-benz [e]indenyl) hafnium dimethyl, pentamethylcyclopentadienyl (1-tert-butyl-benz [e]indenyl) hafnium dimethyl pentamethylcyclopentadienyl (1-pentyl-benz [e]indenyl) hafnium dimethyl, pentamethylcyclopentadienyl (1-neopentyl-benz [e]indenyl) hafnium dimethyl, pentamethylcyclopentadienyl (1-benzyl-benz [e]indenyl) hafnium dimethyl, pentamethylcyclopentadienyl (1-phenethyl-benz [e]indenyl) hafnium dimethyl, pentamethylcyclopentadienyl (1-(2-phenylpropyl)-benzef]indenyl) hafnium dimethyl, pentamethylcyclopentadienyl (1-methyl-5,6,7,8-tetrahydro-1H-cyclopenta[b]naphthalene) hafnium dimethyl, pentamethylcyclopentadienyl (1-ethyl-5,6,7,8-tetrahydro-1H-cyclopenta[b]naphthalene) hafnium dimethyl, pentamethylcyclopentadienyl (1-n-propyl-5,6,7,8-tetrahydro-1H-cyclopenta[b]naphthalene) hafnium dimethyl, pentamethylcyclopentadienyl (1-isopropyl-5,6,7,8-tetrahydro-1H-cyclopenta[b]naphthalene) hafnium dimethyl, pentamethylcyclopentadienyl (1-n-butyl-5,6,7,8-tetrahydro-1H-cyclopenta[b]naphthalene) hafnium dimethyl, pentamethylcyclopentadienyl (1-isobutyl-5,6,7,8-tetrahydro-1H-cyclopenta[b]naphthalene) hafnium dimethyl, pentamethylcyclopentadienyl (1-sec-butyl-5,6,7,8-tetrahydro-1H-cyclopenta[b]naphthalene) hafnium dimethyl, pentamethylcyclopentadienyl (1-tert-butyl-5,6,7,8-tetrahydro-1H-cyclopenta[b]naphthalene) hafnium dimethyl pentamethylcyclopentadienyl (1-pentyl-5,6,7,8-tetrahydro-1H-cyclopenta[b]naphthalene) hafnium dimethyl, pentamethylcyclopentadienyl (1-neopentyl-5,6,7,8-tetrahydro-1H-cyclopenta[b]naphthalene) hafnium dimethyl, pentamethylcyclopentadienyl (1-benzyl-5,6,7,8-tetrahydro-1H-cyclopenta[b]naphthalene) hafnium dimethyl, pentamethylcyclopentadienyl (1-phenethyl-5,6,7,8-tetrahydro-1H-cyclopenta[b]naphthalene) hafnium dimethyl, pentamethylcyclopentadienyl (1-(2-phenylpropyl)-5,6,7,8-tetrahydro-1H-cyclopenta[b]naphthalene) hafnium dimethyl, pentamethylcyclopentadienyl (1-methyl-6,7,8,9-tetrahydro-1H-cyclopenta[a]naphthalene) hafnium dimethyl, pentamethylcyclopentadienyl (1-ethyl-6,7,8,9-tetrahydro-1H-cyclopenta[a]naphthalene) hafnium dimethyl, pentamethylcyclopentadienyl (1-n-propyl-6,7,8,9-tetrahydro-1H-cyclopenta[a]naphthalene) hafnium dimethyl, pentamethylcyclopentadienyl (1-isopropyl-6,7,8,9-tetrahydro-1H-cyclopenta[a]naphthalene) hafnium dimethyl, pentamethylcyclopentadienyl (1-n-butyl-6,7,8,9-tetrahydro-1H-cyclopenta[a]naphthalene) hafnium dimethyl, pentamethylcyclopentadienyl (1-isobutyl-6,7,8,9-tetrahydro-1H-cyclopenta[a]naphthalene) hafnium dimethyl, pentamethylcyclopentadienyl (1-sec-butyl-6,7,8,9-tetrahydro-1H-cyclopenta[a]naphthalene) hafnium dimethyl, pentamethylcyclopentadienyl (1-tert-butyl-6,7,8,9-tetrahydro-1H-cyclopenta[a]naphthalene) hafnium dimethyl pentamethylcyclopentadienyl (1-pentyl-6,7,8,9-tetrahydro-1H-cyclopenta[a]naphthalene) hafnium dimethyl, pentamethylcyclopentadienyl (1-neopentyl-6,7,8,9-tetrahydro-1H-cyclopenta[a]naphthalene) hafnium dimethyl, pentamethylcyclopentadienyl (1-benzyl-6,7,8,9-tetrahydro-1H-cyclopenta[a]naphthalene) hafnium dimethyl, pentamethylcyclopentadienyl (1-phenethyl-6,7,8,9-tetrahydro-1H-cyclopenta[a]naphthalene) hafnium dimethyl, pentamethylcyclopentadienyl (1-(2-phenylpropyl)-6,7,8,9-tetrahydro-1H-cyclopenta[a]naphthalene) hafnium dimethyl, pentamethylcyclopentadienyl (1,5,6-trimethylindenyl) hafnium dimethyl, pentamethylcyclopentadienyl (1-ethyl-5,6-dimethylindenyl) hafnium dimethyl, pentamethylcyclopentadienyl (1-n-propyl-5,6-dimethylindenyl) hafnium dimethyl, pentamethylcyclopentadienyl (1-isopropyl-5,6-dimethylindenyl) hafnium dimethyl, pentamethylcyclopentadienyl (1-n-buty-5,6-dimethyllindenyl) hafnium dimethyl, pentamethylcyclopentadienyl (1-isobuty-5,6-dimethyllindenyl) hafnium dimethyl, pentamethylcyclopentadienyl (1-sec-butyl-5,6-dimethylindenyl) hafnium dimethyl, pentamethylcyclopentadienyl (1-tert-butyl-5,6-dimethylindenyl) hafnium dimethyl pentamethylcyclopentadienyl (1-pentyl-5,6-dimethylindenyl) hafnium dimethyl, pentamethylcyclopentadienyl (1-neopentyl-5,6-dimethylindenyl) hafnium dimethyl, pentamethylcyclopentadienyl (1-benzyl-5,6-dimethylindenyl) hafnium dimethyl, pentamethylcyclopentadienyl (1-phenethyl-5,6-dimethylindenyl) hafnium dimethyl, pentamethylcyclopentadienyl (1-(2-phenylpropyl)-5,6-dimethylindenyl) hafnium dimethyl, pentamethylcyclopentadienyl (1-methyl-1,5,6,7-tetrahydro-s-indacenyl) zirconium dimethyl, pentamethylcyclopentadienyl (1-isobutyl-1,5,6,7-tetrahydro-s-indacenyl) zirconium dimethyl, pentamethylcyclopentadienyl (1,6,6-trimethyl-1,5,6,7-tetrahydro-s-indacenyl) zirconium dimethyl, tetramethylcyclopentadienyl (1-methyl-1,5,6,7-tetrahydro-s-indacenyl) hafnium dimethyl, tetramethylcyclopentadienyl (1-isobutyl-1,5,6,7-tetrahydro-s-indacenyl) hafnium dimethyl, tetramethylcyclopentadienyl (1,6,6-trimethyl-1,5,6,7-tetrahydro-s-indacenyl) hafnium dimethyl, pentamethylcyclopentadienyl (1-methyl-1,5,6,7-tetrahydro-s-indacenyl) hafnium dibenzyl, pentamethylcyclopentadienyl (1-isobutyl-1,5,6,7-tetrahydro-s-indacenyl) hafnium dibenzyl, and pentamethylcyclopentadienyl (1,6,6-trimethyl-1,5,6,7-tetrahydro-s-indacenyl) hafnium dibenzyl.

7. The process of claim 1 wherein the non-aromatic-hydrocarbon soluble activator compound is represented by Formula (V):

$$[R^{1'}R^{2'}R^{3'}EH]_{d+}[Mt^{k+}Q_n]^{d-} \qquad (V)$$

wherein:
E is nitrogen or phosphorous;
d is 1, 2 or 3; k is 1, 2, or 3; n is 1, 2, 3, 4, 5, or 6; n−k=d;
$R^{1'}$, $R^{2'}$, and $R^{3'}$ are independently $C_1$ to $C_{50}$ hydrocarbyl group optionally substituted with one or more alkoxy groups, silyl groups, a halogen atoms, or halogen containing groups
wherein $R^{1'}$, $R^{2'}$, and $R^{3'}$ together comprise 15 or more carbon atoms;
Mt is an element selected from group 13 of the Periodic Table of the Elements; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

8. The process of claim 1 wherein the non-aromatic-hydrocarbon soluble activator compound is represented by Formula (VI):

[R$^{1'}$R$^{2'}$R$^{3'}$EH]$^+$[BR$^{4'}$R$^{5'}$R$^{6'}$R$^{7'}$]$^-$ (VI)

wherein:
E is nitrogen or phosphorous;
R$^{1'}$ is a methyl group;
R$^{2'}$ and R$^{3'}$ are independently is C$_4$-C$_{50}$ hydrocarbyl group optionally substituted with one or more alkoxy groups, silyl groups, a halogen atoms, or halogen containing groups wherein R$^{2'}$ and R$^{3'}$ together comprise 14 or more carbon atoms;
B is boron; and
R$^{4'}$, R$^{5'}$, R$^{6'}$, and R$^{7'}$ are independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

9. The process of claim 1 wherein the non-aromatic-hydrocarbon soluble activator compound is represented by Formula (VII) or Formula (VIII):

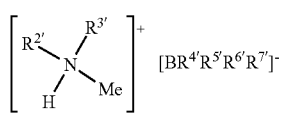  [BR$^{4'}$R$^{5'}$R$^{6'}$R$^{7'}$]$^-$   (VII)

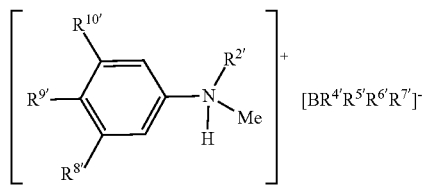  [BR$^{4'}$R$^{5'}$R$^{6'}$R$^{7'}$]$^-$   (VIII)

wherein:
N is nitrogen;
R$^{2'}$ and R$^{3'}$ are independently is C$_6$-C$_{40}$ hydrocarbyl group optionally substituted with one or more alkoxy groups, silyl groups, a halogen atoms, or halogen containing groups wherein R$^2$ and R$^3$ in Formula (VII) together comprise 14 or more carbon atoms and R$^{2'}$ in Formula (VIII) comprises 13 or more carbon atoms;
R$^{8'}$, R$^{9'}$, and R$^{10'}$ are independently a C$_4$-C$_{30}$ hydrocarbyl or substituted C$_4$-C$_{30}$ hydrocarbyl group;
B is boron;
and R$^{4'}$, R$^{5'}$, R$^{6'}$, and R$^7$ are independently hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

10. The process of claim 9, wherein R$^{4'}$, R$^{5'}$, R$^{6'}$, and R$^7$ are pentafluorophenyl.

11. The process of claim 9 wherein R$^{8'}$ and R$^{10'}$ are hydrogen atoms and R$^{9'}$ is a C$_4$-C$_{30}$ hydrocarbyl group which is optionally substituted with one or more alkoxy groups, silyl groups, a halogen atoms, or halogen containing groups.

12. The process of claim 9 wherein R$^{9'}$ is a C$_8$-C$_{22}$ hydrocarbyl group which is optionally substituted with one or more alkoxy groups, silyl groups, a halogen atoms, or halogen containing groups.

13. The process of claim 9 wherein R$^{2'}$ and R$^{3'}$ are independently a C$_{12}$-C$_{22}$ hydrocarbyl group.

14. The process of claim 9 wherein the activator is selected from:
N,N-di(hydrogenated tallow) methylammonium [tetrakis (perfluorophenyl)borate],
N-methyl-4-nonadecyl-N-octadecylanilinium [tetrakis (perfluorophenyl)borate],
N-methyl-4-hexadecyl-N-octadecylanilinium [tetrakis (perfluorophenyl)borate],
N-methyl-4-tetradecyl-N-octadecylanilinium [tetrakis (perfluorophenyl)borate],
N-methyl-4-dodecyl-N-octadecylanilinium [tetrakis(perfluorophenyl)borate],
N-methyl-4-decyl-N-octadecylanilinium [tetrakis(perfluorophenyl)borate],
N-methyl-4-octyl-N-octadecylanilinium [tetrakis(perfluorophenyl)borate],
N-methyl-4-hexyl-N-octadecylanilinium [tetrakis(perfluorophenyl)borate],
N-methyl-4-butyl-N-octadecylanilinium [tetrakis(perfluorophenyl)borate],
N-methyl-4-octadecyl-N-decylanilinium [tetrakis(perfluorophenyl)borate],
N-methyl-4-nonadecyl-N-dodecylanilinium [tetrakis(perfluorophenyl)borate],
N-methyl-4-nonadecyl-N-tetradecylanilinium [tetrakis (perfluorophenyl)borate],
N-methyl-4-nonadecyl-N-hexadecylanilinium [tetrakis (perfluorophenyl)borate], N-ethyl-4-nonadecyl-N-octadecylanilinium [tetrakis(perfluorophenyl)borate],
N-methyl-N,N-dioctadecylammonium [tetrakis(perfluorophenyl)borate],
N-methyl-N,N-dihexadecylammonium [tetrakis(perfluorophenyl)borate],
N-methyl-N,N-ditetradecylammonium [tetrakis(perfluorophenyl)borate],
N-methyl-N,N-didodecylammonium [tetrakis(perfluorophenyl)borate],
N-methyl-N,N-didecylammonium [tetrakis(perfluorophenyl)borate],
N-methyl-N,N-dioctylammonium [tetrakis(perfluorophenyl)borate],
N-ethyl-N,N-dioctadecylammonium [tetrakis(perfluorophenyl)borate],
N,N-di(octadecyl) tolylammonium [tetrakis(perfluorophenyl)borate],
N,N-di(hexadecyl) tolylammonium [tetrakis(perfluorophenyl)borate],
N,N-di(tetradecyl) tolylammonium [tetrakis(perfluorophenyl)borate],
N,N-di(dodecyl) tolylammonium [tetrakis(perfluorophenyl)borate],
N-octadecyl-N-hexadecyl-tolylammonium [tetrakis(perfluorophenyl)borate],
N-octadecyl-N-hexadecyl-tolylammonium [tetrakis(perfluorophenyl)borate],
N-octadecyl-N-tetradecyl-tolylammonium [tetrakis(perfluorophenyl)borate],
N-octadecyl-N-dodecyl-tolylammonium [tetrakis(perfluorophenyl)borate],
N-octadecyl-N-decyl-tolylammonium [tetrakis(perfluorophenyl)borate], N-hexadecyl-N-tetradecyl-tolylammonium [tetrakis(perfluorophenyl)borate],
N-hexadecyl-N-dodecyl-tolylammonium [tetrakis(perfluorophenyl)borate],
N-hexadecyl-N-decyl-tolylammonium [tetrakis(perfluorophenyl)borate],
N-tetradecyl-N-dodecyl-tolylammonium [tetrakis(perfluorophenyl)borate],
N-tetradecyl-N-decyl-tolylammonium [tetrakis(perfluorophenyl)borate],
N-dodecyl-N-decyl-tolylammonium [tetrakis(perfluorophenyl)borate],
N-methyl-N-octadecylanilinium [tetrakis(perfluorophenyl)borate],
N-methyl-N-hexadecylanilinium [tetrakis(perfluorophenyl)borate],
N-methyl-N-tetradecylanilinium [tetrakis(perfluorophenyl)borate],
N-methyl-N-dodecylanilinium [tetrakis(perfluorophenyl)borate],
N-methyl-N-decylanilinium [tetrakis(perfluorophenyl)borate], and
N-methyl-N-octylanilinium [tetrakis(perfluorophenyl)borate].

15. The process of claim 1 wherein the solvent is selected from $C_4$ to $C_{10}$ linear, branched or cyclic alkanes.

16. The process of claim 1 wherein the solvent is essentially free of all aromatic solvents.

17. The process of claim 1, wherein solvent is selected from one or more Co to $C_{32}$ alpha olefins.

18. The process of claim 1 which is wherein the solvent is essentially free of all non-alpha-olefin solvents.

19. The process of claim 1 wherein: the process comprises obtaining an unsaturated PAO product from the polymerization reaction mixture, wherein the polymerization reaction exhibits a selectivity towards greater than or equal to about 80 mol % vinylidenes, based on total moles of vinyls, vinylidenes, di-substituted vinylenes, and tri-substituted vinylenes in the unsaturated PAO product and wherein the unsaturated PAO product has a number average molecular weight (Mn) of 2,500 g/mol or less, as measured by 1H NMR.

20. The process of claim 1, further comprising:
a) contacting the unsaturated PAO product with hydrogen to convert at least a portion of the unsaturated PAO product to a hydrogenated PAO product;
b) contacting the unsaturated PAO product with a chemical reagent to convert at least a portion of the unsaturated PAO product to a functionalized PAO product; or a combination thereof.

21. The process of claim 1 wherein the unsaturated PAO product comprises dimer.

22. The process of claim 1 wherein the $C_6$-$C_{32}$ alpha-olefin, the metallocene compound and the activator are contacted in the solution phase or bulk phase in a continuous stirred tank reactor or a continuous tubular reactor.

23. The process of claim 1 wherein the process is a continuous process which includes the steps of: a) continuously introducing a feed stream comprising at least 10 mol % of the one or more $C_6$ to $C_{24}$ alpha-olefins into a reactor, b) continuously introducing the metallocene compound and the activator into the reactor, and c) continuously withdrawing the PAO product from the reactor.

24. The process of claim 1, wherein the feed comprises a single alpha-olefin monomer or a combination of two or more alpha-olefin monomers.

25. The process of claim 1 wherein the $C_6$-$C_{32}$ alpha-olefin, the metallocene compound and the activator are contacted in the solution phase, bulk phase, or slurry phase in a continuous stirred tank reactor or a continuous tubular reactor.

26. The process of claim 1 wherein the polymerization temperature is above 100° C., the conversion is 50% or more and the unsaturated PAO product has about 80 mol % or more vinylidenes, based on total moles of vinyls, vinylidenes, di-substituted vinylenes, and tri-substituted vinylenes in the unsaturated PAO product.

27. The process of claim 1 wherein the unsaturated PAO product is represented by formula:

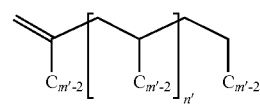

wherein C is a hydrocarbon chain of length m'-2, each m' is independently 4, 5, 6, 7, 8, 9, 10, 11, 12, 13, 14, 15, or 16 and is the carbon number of the monomer(s) used in the polymerization, and n' is 0, 1, 2, 3, 4, 5, 6, 7, 8, 9, or 10.

28. The process of claim 1, said process having productivity of at least 4,500 g/mmol/hr, wherein the process comprises: contacting, at a temperature of from 35° C. to 150° C.

29. The process of claim 1, further comprising hydrogenating at least a portion of said poly alpha-olefin, then formulating a fuel or lubricating composition comprising the product of hydrogenating at least a portion of said polyalpha-olefin.

* * * * *